(12) United States Patent
Cremer et al.

(10) Patent No.: US 7,298,461 B2
(45) Date of Patent: Nov. 20, 2007

(54) FAR FIELD LIGHT MICROSCOPICAL METHOD, SYSTEM AND COMPUTER PROGRAM PRODUCT FOR ANALYSING AT LEAST ONE OBJECT HAVING A SUBWAVELENGTH SIZE

(75) Inventors: Christoph Cremer, Heidelberg (DE); Antonio Virgilio Failla, Rome (IT); Benno Albrecht, Heidelberg (DE)

(73) Assignee: Ruprecht-Karls-Universitat, Heidelberg (DE)

( * ) Notice: Subject to any disclaimer, the term of this patent is extended or adjusted under 35 U.S.C. 154(b) by 404 days.

(21) Appl. No.: 10/492,266

(22) PCT Filed: Oct. 9, 2002

(86) PCT No.: PCT/EP02/11343

§ 371 (c)(1),
(2), (4) Date: May 17, 2004

(87) PCT Pub. No.: WO03/031951

PCT Pub. Date: Apr. 17, 2003

(65) Prior Publication Data

US 2005/0059681 A1 Mar. 17, 2005

Related U.S. Application Data

(60) Provisional application No. 60/328,021, filed on Oct. 9, 2001.

(51) Int. Cl.
*G01N 21/00* (2006.01)
(52) U.S. Cl. .................................................. 356/73
(58) Field of Classification Search ............... None
See application file for complete search history.

(56) References Cited

U.S. PATENT DOCUMENTS 6,017,434 A * 1/2000 Simpson et al. ............. 204/612
6,104,945 A * 8/2000 Modell et al. ............... 600/473
6,259,104 B1 * 7/2001 Baer ........................ 250/492.2

FOREIGN PATENT DOCUMENTS

DE 198 30 596 A1 1/1999
EP 0 732 584 A2 9/1996
EP 0 1008 845 A1 6/2000

OTHER PUBLICATIONS

Fai-field fluorescence microscopy beyond the diffraction limit—XP-001146247—A.M. van Oijen, J. Kohler, and J. Schmidt—vol. 16, No. 4, Apr. 1999—pp. 909-915.

* cited by examiner

*Primary Examiner*—Michael P. Stafira
(74) *Attorney, Agent, or Firm*—Gerald E. Hespos; Anthony J. Casella

(57) ABSTRACT

The present invention relates to a far field light microscopical method, respectively a system and a computer program product for analysing at least one object having a subwavelength size in at least one spatial direction to obtain spatial information of the object, in particular size and topology thereof, comprising the steps of:—labelling the object(s) with one or more suitable optical markers;—providing suitably structured illumination light to at least partially illuminate the object(s);—subjecting the object(s) to the structured illumination light;—detecting an optical response of the object(s);—obtaining the spatial information of the object(s) by comparing the obtained response with simulation data of an optical response of object(s) having known spatial information.

21 Claims, 31 Drawing Sheets

S(0) labelled by specs 1

S(1) labelled by specs 2

1) D = 0 nm
2) D = 20 nm
3) D = 40 nm
4) D = 60 nm
5) D = 80 nm

FAR FIELD LIGHT MICROSCOPICAL METHOD, SYSTEM AND COMPUTER PROGRAM PRODUCT FOR ANALYSING AT LEAST ONE OBJECT HAVING A SUBWAVELENGTH SIZE

BACKGROUND OF THE INVENTION

1. Field of the Invention

The present invention relates to a far field light microscopical method, system and computer program product for analysing at least one object having a subwavelength size. In particular, it relates to a method to analyse the size and topology of subwavelength sized objects, such objects being in particular polymeric structures and supramolecular complexes composed of several to many units fluorescence labelled with an appropriate number of one or more spectral signatures, or any other fluorescent structures, having a subwavelength size at least in one spatial direction, by using spatially modulated illumination microscopy or other methods providing suitable structured illumination in the object plane, or object volume in combination with special calibration procedures obtained by "virtual microscopy" based specially designed information technology tools.

2. Description of the Related Art

Since the work of Abbe and Rayleigh at the end of the 19th century wave theory appeared to impose an absolute limit on the potential of light microscopy as a tool to study the nanostructure of thick transparent specimens such as cells and cell nuclei. In an advanced conventional epifluorescence light microscope or using Confocal Laser Scanning fluorescence Microscopy (CLSM), the optical resolution is limited laterally to about 200 nanometers and to about 1 µm (CLSM: about 600 nm) in the direction of the optical axis of the microscope system, assuming biologically relevant conditions. The above mentioned conventional optical resolution is the smallest detectable distance between two point like objects with the same optical characteristics (for example of same spectral signature) and is also often characterised by the Full-Width-at-Half-Maximum (FWHM) of the microscopic point spread function. In other words, the Point Spread Function (PSF) is the normalised spatial fluorescence intensity distribution in the image plane obtained of a "point like" fluorescent object and the width of this distribution at half the maximum intensity (Full-Width-at-Half-Maximum) is a measure for the optical resolution.

The conventional optical resolution, often in combination with advanced three-dimensional (3D)-deconvolution techniques, is already sufficient to study many important topics, such as of cell biology in general, including e.g. human genome structure on a scale down to 0.2 µm. For example, using a conventional epifluorescence light microscope, or Confocal Laser Scanning fluorescence Microscopy, it became possible to perform genome wide cytogenetic analysis of all mitotic chromosomes and to identify chromosome band regions down to several Megabase pairs (Mbp) in nucleic acids (DNA) as disclosed in M. R. Speicher, G. S. Ballard, D. C. Ward, Karyotyping human chromosomes by combinatorial multi-fluor FISH: Nature Genet. 12: 368-375 (1996); to visualise in human cell nuclei appropriately labelled chromosome territories, chromosome arm territories and still smaller chromatin domains down to the level of about 1 Mbp of DNA; to identify individual genes, using Fluorescence In Situ Hybridisation (FISH) techniques, and to estimate their spatial distribution by using in situ hybridisation methods, especially Fluorescence In Situ Hybridisation; to localise in living cells individual DNA sequences, using e.g. lac operator/repressor recognition; to visualise protein and protein/Ribo Nuclein Acids (RNA) complexes related to genome function; to measure the local mobility of individual protein and RNA molecules or other structures, in the nucleus of living cells using Fluorescence Recovery After Photobleaching (FRAP) or Fluorescence Correlation Spectroscopy (FCS) techniques.

Compared with the typical size of nucleosomes (about 11 nm diameter), of the chromatin loops of individual genes (e.g. 100 kilobase pair (kbp) corresponding to a linear extension of about 100 nm), or supramolecular complexes composed of two or more macromolecules) required for replication, transcription, splicing, repair of DNA (typical size diameter estimates up to several hundreds of nm), for macromolecular transport, protein synthesis, protein degradation, ion transport etc., the light microscopical resolution, revealed in the state of the art, is by far not sufficient to answer many pressing questions of present biological, e.g. human genome structure research. Such problems comprise e.g. the extent of an interchromatin domain space; the relative positioning of specific genes with respect to chromatin domains; the spatial structure and temporal dynamics of specific gene regions; the spatial requirements for accessibility of specific proteins to transcription factor binding sites located in the DNA-sequence; the assembly and disassembly of genome function related supramolecular complexes; the analysis of small changes in the compactness of a specific gene region as a prerequisite or as a consequence of transcription as disclosed in T. Cremer & C. Cremer, Chromosome Territories, Nuclear Architecture and Gene Regulation in Mammalian Cells, Nature Reviews Genetics Volume 2, 292-301 (2001); the assembly and disassembly of other complexes important for cellular metabolism. The solution of such problems is not only of scientific but also of practical interest. For example, an improved knowledge of spatial human genome complexes and other supramolecular complexes will be of importance not-only in diagnostic but also in drug design for therapeutic treatments of pathological states such as cancer, or aging related diseases.

In the following, the subwavelength sized biological objects (using visible light as a reference) mentioned above are denoted as "BioMolecular Machines" or BioMolecular Modules (BMM). Here, a BMM is defined as any subwavelength sized collection of interacting biological macromolecules of whatever type (e.g. proteins, nucleic acids, sugars, fatty acids, etc.). In spherical objects, the word size means the diameter. In non-spherical objects it means the diameter of the minimum enveloping ellipsoid (sphere), or the extension of the object in a defined spatial direction, given for example by twice the half axes of a minimum enveloping ellipsoid. If the extension of the object is determined in the direction of the optical axis of the microscope system, "size" or "axial size" means this extension. A more exact meaning of the word "size" is obtained by Virtual Microscopy (VIM) calculations as described in more detail in the following, referring the word "size" to a specific measurement situation.

In addition to BioMolecular Machines or BioMolecular Modules, the light microscopical analysis of other macromolecules or interacting collections of macromolecules has important applications, e.g. in polymer analysis. In the following, the word MacroMolecular Complexes (MMC) is used to denote BioMolecular Machines or BioMolecular Modules as well as other macromolecules or collection of macromolecules. A colocalization volume or the diameter of the minimum enveloping spherical volume, or the half axis of a minimum enveloping ellipsoid, of a collection of fluorescent but not interacting macromolecules, as well as interacting macromolecules can be determined. For brevity, all procedures described for MacroMolecular Complexes or BioMolecular Machines or BioMolecular Modules are applicable also to determine the size of the colocalization volume. For the analysis of such MacroMolecular Complexes, it is highly desirable to increase further the resolution of Far Field Light Microscopy (FFLM). For example, far field light microscopical analysis with increased resolution would allow to study such MacroMolecular Complexes in their physiological or natural environment, such as in the interior of thick transparent specimens as cells and cell nuclei. Due to the relatively low photon energy of light, even analysis in living systems is possible. In polymer research it would allow to study e.g. structures of polymers without any major photonic interaction such as ionising radiation in the case of X-ray, electron beam analysis, or mechanical interaction such as Atomic Force Microscopy (AFM).

For many decades, however, a further resolution improvement in Far Field Light Microscopy appeared to be impossible. Consequently, alternative ways were developed. In particular, X-ray crystallography and electron microscopy allowed further enormous progress in the elucidation of such MacroMolecular Complexes, e.g. of three-dimensional (3D) genome structures and related protein/DNA complexes. In addition, surface related techniques like Atomic Force Microscopy or Near Field Scanning Optical Microscopy (NSOM) allowed studies of isolated genome structures at a resolution considerably below 100 nm, i.e. about 4-7 times smaller than the wavelength of visible light usually used in light microscopic studies. These techniques contributed widely to cell biology and medical research in general including genome structure research. Nonetheless, only Far Field Light Microscopy methods would allow the non-destructive study of MacroMolecular Complexes in the interior of thick transparent specimens, in particular BioMolecular Machines or BioMolecular Modules in the interior of cells, such as the 3D-architecture of the human genome and its temporal dynamics in the nuclei of morphologically conserved and even living cells. In addition, Far Field Light Microscopy methods of appropriate resolution are useful also where Atomic Force Microscopy and Near Field Scanning Optical Microscopy techniques can be applied: since these latest techniques are mechanically interacting due to the "tip scanning", and since they are rather slow in image formation.

In the past there have been from time to time speculations on how to break the "Abbe limit" of resolution in Far Field Light Microscopy, or in other words light microscopic methods where the distance between the object to be analysed and the first light collecting element of the registration system is typically in the order of $10^2$ wavelengths and more; until recently they were not realised to such an extent that they were really useful in biology or other MMC-analysis. To describe the state of the art, in the following, we shall indicate the relevant recent major developments in Far Field Light Microscopy (FFLM) using fluorescence labelled objects.

Improvements of Optical Resolution

Since the beginning of the 1990's, Far Field Light Microscopical devices were designed and then realised having a highly improved and practically usable optical-resolution. This goal was achieved by using different ways of narrowing the microscopic Point Spread Function. The starting point was the thoroughly calculated theoretical design of a 4Pi microscope where the spatial angle of the incident focusing wave was substantially enlarged, and with the experimental realisation of such a microscope, which is described in detail in S. W. Hell & J. Wichmann, in "Breaking the diffraction resolution limit by stimulated emission: STED fluorescence microscopy", Optics Left. 19, 780-782 (1994).

In another approach, a further resolution increasing modulation of the point spread function, called "point spread function engineering", or in other words methods to narrow or modulate the Point Spread Function in a way to increase the optical resolution beyond conventional high resolution confocal microscopy, was achieved by a sophisticated use of Stimulated Emission Depletion (STED) in the object (Stimulated Emission Depletion microscopy). By such methods, a true optical resolution in the order of ⅛ of the exciting wavelength (less than 100 nm) has now already been achieved (T. A. Klar, S. Jakobs, M. Dyba, A. Egner & S. W. Hell, Fluorescence microscopy with diffraction resolution barrier broken by stimulated emission, Proc. Natl. Acad. Sci. USA 97, 8206-8210 (2000)). Theoretical considerations have been revealed describing the design of a Far Field Light Stimulated Emission Depletion STED-microscope having an optical resolution in the order of 1/40-1/20 (about 20-40 nm) of the exciting wavelength [S. W. Hell & J. Wichmann, Breaking the diffraction resolution limit by stimulated emission: STED fluorescence microscopy, Optics Lett. 19, 780-782 (1994).].

Improvements of Topological Resolution

For light microscopical studies of MacroMolecular Complexes and in particular of BioMolecular Machines or BioMolecular Modules, it is important to measure positions and mutual distances ("topology") between smaller, fluorescent labelled, parts ("elements") of such complexes (e.g. protein subunits, or nucleic acid sequences or part of them subunits, or positions of other special nucleic acid sequences) with high precision even if they are situated in thick transparent specimens. This allows for example to examine human genome topology in three-dimensionally (3D) intact cell nuclei as described in T. Cremer & C. Cremer, Chromosome Territories, Nuclear Architecture and Gene Regulation in Mammalian Cells, Nature Reviews Genetics Volume 2, 292-301 (2001), especially when the elements are labelled with fluorescent markers having different spectral signatures as described in WO 98/28592; DE 19654824.1,. As a consequence, this allows to identify the objects due to their fluorescence life times or excitation/emission spectra. The elements positions and their mutual distances are then determined from their coordinates in the image data file, e.g. with respect to a given cover slip position using the known magnification parameters of the microscopical set up. Using confocal microscopy, a topological distance resolution in the order of about 35 nm laterally (in the object plane) and about 50 nm axially (perpendicular to the object plane) has been achieved in topological studies of human nuclear genome regions described in A. Esa, P. Edelmann, L. Trakhtenbrot, N. Amariglio, G. Rechavi, M. Hausmann, C. Cremer, Three-dimensional spectral precision distance microscopy of chromatin nanostructures after triple-colour DNA labelling: a study of the BCR region on chromosome 22 and the Philadelphia chromosome, J. Microsc. 199, 96-105 (2000)]. Here, "Topological Resolution" (sometime also called "Resolution Equivalent" RE) is defined as the smallest distance which can be detected between two appropriately fluorescence labelled elements where these elements have a distance equal or larger than the optical resolution from other elements having a fluorescence label of the same spectral signature (see FIG. 1). Such distance requirements may be realised in different ways e.g. by labelling specific sites in a cell as disclosed in A. Esa, P. Edelmann, L. Trakhtenbrot, N. Amariglio, G. Rechavi, M. Hausmann, C. Cremer, Three-dimensional spectral precision distance microscopy of chromatin nanostructures after triple-colour DNA labelling: a study of the BCR region on chromosome 22 and the Philadelphia chromosome, J. Microsc. 199, 96-105 (2000), or by using nanolithographically produced arrangements as disclosed in DE 100 52 823. Although many biological systems display a considerable flexibility in the topology of their elements, it remains important to further increase the topological resolution since:

It is well known that in small BioMolecular Machines or BioMolecular Modules (BMM), such as complexes formed of a few proteins as subunits or "elements" only, the distances between the subunits can vary to a very limited extent only, due to the short range interaction of the hydrogen bond and van-der-Waals forces important in keeping the BMM together as a functional unit. Such forces are in the subnanometer interaction range; hence, changes in the nm-range may severely alter the biological integrity or function of such a BMM. For example, a Biomolecular Machine or Module of 30 nm diameter with a ring like arrangement of 20 different elements, such as proteins, would allow $20!=2.4\times10^{18}$ different topological arrangements with respect to given point and it is highly unlikely that all $2.4\times10^{18}$ arrangements which differ in topology only by a few nm up to a maximum of 30 nm would all have the same biological function.

It is to be expected that also larger BioMolecular Machines or BioMolecular Modules such as proteasomes involved in the degradation of proteins, require a topological precision on the nanometer or subnanometer scale, at least for some of their elements.

Large BioMolecular Machines or BioMolecular Modules, such as Mbp-chromatin domains containing about 1 Mbp of DNA [T. Cremer & C. Cremer, Chromosome Territories, Nuclear Architecture and Gene Regulation in Mammalian Cells, Nature Reviews Genetics Volume 2, 292-301 (2001)], appear to exhibit a much larger degree of flexibility: it is likely, however, that the changes in the degree of condensation (or "compaction") of a specific gene region induced by such a flexibility may result in significant changes of functional activity e.g. due to differences in accessibility to macromolecular factors. In this case, a high topological resolution would allow to distinguish different functionally relevant states of the Biomolecular Machine or Module (BMM). From the variance of the structural parameters of such a flexible BMM, elastic parameters characterising the BMM may be determined. Such elastic parameters may be calculated by using appropriate models of BMM. Especially useful in this aspect are quantitative modelling and simulations approaches as disclosed in DE 100 52 583 A1.

Confocal Laser Scanning fluorescence Microscopy allows a nondestructive, high resolution three-dimensional (3D) microscopy of small biological objects, such as individual cells, containing fluorescence labelled targets, with a contrast and 3D-resolution superior to all other light optical far field techniques so far commercially available. Since the introduction of the first Confocal Laser Scanning fluorescence Microscopes (CLSM's) into biological research in the mid 1980's, numerous studies have used this new microscopic technique also for an improved analysis of the architecture of the cell nucleus.

In the beginning of these studies, One/Two Channel Confocal Laser Scanning fluorescence Microscopy's were used which allowed the simultaneous registration of one or two spectral signatures only; i.e. fluorescence labelling of targets could be performed with two colours. A few years ago, Three Channel Confocal Laser Scanning fluorescence Microscopy's, and more recently, Multi-channel Confocal Laser Scanning fluorescence Microscopy's have been introduced by different manufacturers. Presently, Confocal Laser Scanning fluorescence Microscopes with 8 channels are commercially available from the principal manufacturers. In special systems, up to 32 channels are used, allowing to obtain full fluorescence emission spectra on a voxel-by-voxel base. In addition, detector systems suitable for fluorescence life time detection are commercially available. Such Confocal Laser Scanning fluorescence Microscopy's systems are equipped with several lasers allowing one and two photon excitation and discriminated spectral registration for almost any fluorophor presently used in cell biological microscopy. As examples for such fluorophores or fluorochrome markers, DAPI, Hoechst, Indo, Fura2, FITC, DTAF, Cy2, DiO, FDA, Lucifer Yellow, Ethidium bromide, TRITC, Texas Red, Hoechst 33258, etc. are mentioned. In particular, a large collection of fluorescent labelling procedures "in vivo" is available, such e.g. an incorporation of fluorochrome conjugated nucleotides or green fluorescent proteins and their variants [GFP, EBFP, EYFP, dsRed [G. Patterson, R. N. Day, D. Piston, Fluorescent protein spectra, J. of Cell Science 114: 837-838]. In addition procedures have been revealed to allow the "in vivo" fluorescent labelling of specific nucleic acid sequences by complementary base pairing, using fluorescent-labelled nucleic acid probes described for example in U.S. Pat. No. 5,888,734; WO 98/3723]; specific labelling of proteins can be defined by various procedures, such as e.g. antibody staining, aptamere labelling, amino acid residue modification, as well as by binding to a variety of semiconductor nanocrystals with different spectral signatures may be mentioned.

In this context, "spectral signature" (preferably called also optical marker or an optical marker with a spectral signature in the following) means any photophysical property which can be used for optically discriminated registration; spectral registration means any registration mode allowing to realise this discriminated registration (i.e. registration of the optical response of the object) using e.g. different excitation and/or emission wavelengths, in combination with fluorescent life time detectors polarisation state detectors etc. According to the state of the art, it is feasible to simultaneously use for Confocal Laser Scanning fluorescence Microscopy analysis a maximum of about 16 spectral signatures bound to specific biological structures or other macromolecules. As an example, 8 different spectral signatures may be realised by the use of nanometer sized semiconductor "Quantum Dots" bound closely connected to the specific "elements" using for spectral discrimination the narrow fluorescence emission spectra obtained after ultraviolet light (UV) excitation. An additional 8 spectral signatures may be realised by using 4 types of fluorochrome molecules with two different fluorescence life times each. Here, "simultaneous use" is understood to include also sequential illumination within a time frame within the $10^2$ msec range.

As examples for the application of advanced Confocal Laser Scanning fluorescence Microscopy-Spectral Position Distance Microscopy (Spectral Position Distance Microscopy) are mentioned topology problems in the analysis of functional nuclear architecture, such as: the size and spatial distribution of specific chromosome territories, chromosome arm territories, or chromosome band domains; the formation of "Factories" for replication, transcription, splicing, and repair; the arrangement of specific chromosomal subdomains and genes in chromosomal territories; the topological structure of "imprinted" regions where the maternal and paternal genes are differently active; the topological structure of gene regions correlated with the development/progression of cancer; the influence of physical and chemical agents (such as ionising radiation, chemical environmental mutagens) on the topological structure of specific gene regions; the correlation between topological structure and gene expression; the change of topological structure of specific gene regions as a result of cell determination/differentiation; the quantitative analysis of transcription factor binding site accessibility related to a specific gene region; the simultaneous identification of multiple chromosomes (e.g. all chromosome territories in a human or mouse nucleus), chromosomal subregions, and individual gene regions by combinatorial labelling and colocalization analysis.

The information value of the data obtained drastically increases with the number of nuclear targets which can be labelled and identified simultaneously. For example, the independent registration of four spectral signatures allows the simultaneous identification of 15 different nuclear targets at a sufficiently large distance from each other, using 4-colour combinatorial labelling.

An application of 8 channels allows colocalization and topology analysis of 8 different "elements" using 8 spectral signatures and 8 independent registration channels, and the simultaneous identification of up to 255 different nuclear targets (again assuming a distance equal or larger than the optical resolution between targets having the same spectral signature), using 8-colour combinatorial labelling as disclosed in DE 100 52 583 A1. Although presently a maximum of 4-7 different spectral signatures is used, fluorescence labelling techniques are advancing with such a speed that the simultaneous use of even 8 and more spectral signatures in nuclear architecture and other studies is expected. For example, using fluorescence lifetime detection in addition to fluorophor discrimination by different excitation/emission wavelengths, the simultaneous registration of 8-16 spectral signatures is feasible from the optical point of view with optical systems at the state of the art. However, one has to consider that with an increase in the number of labelling targets, a full labelling will become increasingly difficult from the preparative point of view. For example, if the probability p for binding to a given target is $p_0$, then the probability $p_{tot}$ for full N spectral signature labelling can be estimated to be $p_{tot}=(p_0)^N$ e.g N=16 and $p_0=0.9$, $p_{tot}=0.2$; for $p_0=0.8$, $p_{tot}=0.03$. In target configurations obtained by combinatorial labelling, this would not be acceptable, while in Spectral Position Distance Microscopy applications, one may select those structures displaying the desired number of spectral signatures. It is expected that the availability of multi-channel instruments will further stimulate the development of multispectral labelling strategies also from the preparative point of view. Analogous labelling advantages may be obtained for any other Biomolecular Machine or Modules or Macromolecular Complexes.

One of the basic problems of quantitative high precision multi-channel Confocal Laser Scanning fluorescence Microscopy studies using continuous wave One-Photon excitation and different excitations is the correct calibration of chromatic aberrations. These problems are considerably diminished if Two-Photon excitation of different dyes at the same wavelength is possible. In this case, the maximum excitation at different wavelengths, of different fluorochromes is in the same optical plane whereas with One-Photon excitation, the maximum excitation normally occurs in different optical planes. For example, applying a Confocal Laser Scanning fluorescence Microscopy with a Two-Photon option using a Ti:Sa laser source with pulses in the 100 femtosecond range together with time-correlated-photon-counting detectors and measuring fluorescent lifetimes at the same emission wavelength allows to eliminate the chromatic aberration completely. Such "Fluorescent Lifetime Imaging Microscopy" (FLIM) approaches may be realised also using pulsed laser sources producing One-Photon excitation. In this case, the problem is to identify correctly the objects due to their fluorescence lifetimes. Using appropriate algorithms, at the state of the art a fluorescence photon count in the order of $10^4$ is sufficient to obtain a localisation precision in the nanometer range.

Multi-channel Confocal microscopy is increasingly being used to study different aspects of specific MacroMolecular Complexes, such as nuclear nanostructures. For example, Confocal Laser Scanning fluorescence Microscopy's have been used to allow to determine a colocalization of two objects labelled with different spectral signatures with an accuracy well below the nominal optical resolution (given as the smallest detectable distance between two objects of the same spectral signature). Using visual ovservation, colocalization means that the distance of the two objects is so small that the diffraction images of the objects labelled with different spectral signatures are overlapping. Thus, e.g. in the case of large nuclear protein complexes, it is inferred to be probable that the two labelled objects belong to the same complex. The technique of Fluorescence Resonance Energy Transfer (FRET) measurements allows distance determination at very small distances (below 10 nm), it allows quantitative distance measurements only at specific conditions (such as spectral overlap; specific orientation of the molecular dipoles), and only for a few distances simultaneously. Thus, multispectral Spectral Position Distance Microscopy measurements complement FRET analysis to determine the colocalization of multiple elements or other objects. Generally Spectral Position Distance Microscopy allows to bridge the gap between the FRET range and the nominal optical microscopic resolution. Using visual inspection of the Confocal Laser Scanning fluorescence Microscopy images, however, means that the colocalization error still is in the order of at least $\delta_x=\delta_y=50$ nm laterally and $\delta_z=300$ nm axially, due to the uncertainties in visual colocalization and insufficiently chromatic aberration effects. At the state of the art, calibration procedures and digital image analysis algorithms using Spectral Position Distance Microscopy are available which allow to reduce the nuclear colocalization error to about 35 nm laterally and 50 nm axially. If the "Colocalization Volume" ($V_{col}$) is estimated by $V_{col}=(4/3)\cdot\pi\cdot\{(\delta_x/2)\cdot(\delta_y/2)\cdot(\delta_z/2)\}$, then by using Spectral Position Distance Microscopy the colocalization volume is reduced by a factor $(50\cdot50\cdot300)/(35\cdot35\cdot50)=12.2$, i.e. by about one order of magnitude. This considerably smaller colocalization volume comes into the order of the enveloping volume of individual large macromolecular complexes (MMCs). Thus, the Spectral Position Distance Microscopy approach to colocalization allows to increase substantially the probability that the colocalization detected indicates indeed a functional individual macromolecular complex. Furthermore, if distances between "elements" in a MMC are larger than the Spectral Position Distance Microscopy—distance resolution (" topological resolution", see FIGS. 1, 6), the SPDM method allows topology analysis by multiple measurements of the relative positions and mutual distances of objects labelled with different spectral signatures.

A reference is made to FIG. 1 which shows a schematic example of the optical (FIG. 1A) and topological (FIG. 1B) resolution. In FIG. 1A $d_{or}$ is the smallest distance between any two elements, labelled with the same spectral signature and illustrates the Abbe limit of the optical resolution. In FIG. 1B $d_{top}$ is the smallest distance between two elements fluorescent labelled with appropriate spectral signature. For example if the elements 1, 2, 3 in a MMC (A) are labelled with different spectral signature, respectively specs 1, specs 2, specs 3 and if the distance D between the equally labelled elements 1 and 4, 2 and 5, 3 and 6 in a MMC (A) and MMC (B), respectively, is equal or larger than $d_{or}$, then the positions and the mutual distances of and between elements 1, 2, 3 in MMC (A), and of and between elements 4, 5, 6 in MMC (B) can be determined even if the distances between the elements 4, 5, 6 in MMV (B) are considerably smaller than the optical resolution $d_{or}$. The example given applies to a labelling strategy where the elements in a given Macro Molecular Complex (MMC) to be analysed have all different spectral signature.

Using a preferred embodiment of the invention presented below, a topological resolution $d_{top}$ better than the optical resolution $d_{top} < d_{or}$ can be achieved also in the case two elements in a MMC carry the same spectral signature.

Referring to FIG. 6, which shows a schematic example illustrating the limits for topological analysis by SMI. In FIG. 6A the elements 1, 2, 3, 4 . . . N are localized in the interior of a minimum enveloping volume of diameter $d_{top}$ ($d_{top}$ is the topological resolution). In FIG. 6B the elements 1, 2, 3, 4, . . . N are localized in a minimum enveloping volume of diameter $D_c$, such that $D_c > d_{top}$. The distances $d_{ik}$ between any elements i and k are equal or longer to $d_{top}$, so that $d_{ik} > d_{top}$.

To achieve still better distance determinations and topology analysis with a precision in the nanometer range under biologically relevant noise conditions, methods of Point Spread Function engineering (see FIG. 1) may be used. The technical goal is to modify the Point Spread Function of the microscope system in such a way that a maximum precision of position determination of the object can be achieved by the total fluorescence photon count given. Presently, axial distance measurements between small fluorescent objects approaching the range of a few nanometers and with a precision in the One-Nanometer range are feasible using such methods [M. Schmidt, M. Nagorny & S. W. Hell, Subresolution axial measurements in far-field fluorescence microscopy with precision of 1 nanometer, Rev. Scient. Instr. 71, 2742 -2745 (2000); B. Albrecht, A. V. Failla, A. Schweitzer, C. Cremer, Spatially modulated illumination (SMI) microscopy allows axial distance resolution near the one nanometer range, Applied Optics, in press. 2001]. Theoretical considerations based on Virtual Microscopy computer simulations indicate that using microscope systems with an appropriately modified Point Spread Function, the precision of distance measurements in the few-nanometer range can be improved to the sub-nanometer range, using the fluorescence photon counts available from single fluorophores [B. Albrecht, A. V. Failla, A. Schweitzer, C. Cremer: Spatially modulated illumination microscopy: A new approach to biological nanostructure analysis, GIT-Microscopy, July 2001].

The possibility to measure topology related distances in the nanometer range with a precision in the One-Nanometer range, and better will e.g. allow to discriminate functional from aberrant BioMolecular Machines or Modules: It is known that very small changes in the topology of BMMs may have a major influence on their function. As a scientifically as well as economically important application, this will allow e.g. to better analyse and control topological alterations induced by pharmaceutical drugs under physiological relevant conditions.

In other cases, the topological resolution may be better, i.e. have a smaller value, than the biological variation in the distances encountered, e.g. between two labelled genomic sites on a chromatin fiber in a mammalian cell nucleus. In this case, precise topology measurements will allow to measure the variation in the structural states of these sites, and thus provide important parameters for a better understanding of human genome dynamics. For example, at given distance variations, small changes in the mean mutual distances between genomic sites in a gene region may change the probability of access of such a site to transcription factors or transcription factories and thus play an important role in eukaryotic gene regulation [T. Cremer & C. Cremer, Chromosome Territories, Nuclear Architecture and Gene Regulation in Mammalian Cells, Nature Reviews Genetics Volume 2, 292-301 (2001)].

Problems related to the State of the Art

The "state of the art" methods described above, in a number of applications show several drawbacks which make desirable the additional introduction of new techniques.

For example, an important class of problems and applications in biological and biomedical research relates to the diameter (size) of a colocalization volume or to the diameter (size) of a specific BioMolecular Machine or BioMolecular Module. Examples for this are: the discrimination of functional BioMolecular Machines or Modules in the states of formation, by measuring the colocalization volumes of the elements; the sizes of nuclear pores; of transcription factories; of replication factories; of inactive genes (thought to be generally more condensed), or of active genes (thought to be generally less condensed). In polymer research, an important problem is to measure the size of individual macromolecules in their "natural" environment. Although electron microscopy, Atomic Force Microscopy, or Near Field Scanning Optical Microscopy offer important possibilities to perform size measurements in the required range (down to the nanometer range), far field light microscopical approaches towards such high resolution size measurements would allow to complement and facilitate such measurements considerably. For example, they can be performed in thick transparent specimens, such as in three-dimensionally intact cells, eventually even in living ones. Similar considerations apply to other BioMolecular Machines or BioMolecular Modules and MacroMolecular Complexes.

A "truly point like" fluorescent object (e.g. one fluorochrome molecule of 1 nm diameter) would result in a diffraction image with the smallest diameter achievable with the microscope system used. This "ideal" diffraction image would correspond to the Point Spread Function of the microscope system; its diameter corresponds to the Full-Width-at-Half-Maximum [FWHM] of the Point Spread Function. The "ideal" diffraction image would be disturbed by larger objects. In fact a larger object can be represented as the superposition of several point like objects each one emitting independently to the others; the larger the object diameter, the larger the deviation from the ideal diffraction image. This means that knowing precisely the Point Spread Function of the system, object diameters even below the Full-Width-at-Half-Maximum of the Point Spread Function of the system can be determined. Using special procedures like volume conserving algorithms, object diameters down to about half the wavelength of the exciting light (i.e. several hundreds of nanometers) have been determined by confocal laser scanning fluorescence microscopy. For Confocal Laser Scanning fluorescence Microscopy this minimum correctly detectable diameter ("size resolution") was found to be in the order of 200 nm and thus is not sufficient for many of the above mentioned applications in polymer research and in cell biology, especially also in human genome structure research. Using Point Spread Function-engineering with a considerably smaller Full-Width-at-Half-Maximum (FWHM) of the Point Spread Function, it becomes possible to measure considerably smaller sizes of fluorescent objects.

Using a Stimulated Emission Depletion STED-microscope with a Full-Width-at-Half-Maximum of 20-40 nm, it is possible to determine the size of a BioMolecular Machine or BioMolecular Module down to about this value. Using additionally Spectral Position Distance Microscopy methods with appropriate multispectral signature labelling allows topological analysis at the one-to-few nanometer distance resolution, with a precision in the subnanometer range at a moderate fluorescence photon count. This requires the labelling of the BMM with fluorochromes where the STED microscopy can be applied. With these possibilities, STED microscopy opens prospective for the far field light microscopical analysis of fluorescent structures until recently thought to be physically impossible. For example, if 27 (3×3×3=27) "point like" fluorescent objects are positioned within the observation volume of a conventional high resolution confocal microscope, labelled with the same spectral signature and have a minimum mutual distance larger than 30 nm, their topology can still be analysed by a STED-microscope with 30 nm Full-Width-at-Half-Maximum of the STED-PSF. Such a topological resolution, using one spectral signature labelling, can presently be achieved by no other far field light microscopical method.

Nonetheless, Point Spread Function Engineering approaches by measuring the Point Spread Function as revealed so far have drawbacks in a number of instances which makes it desirable to develop and use additional techniques for far field light microscopical analysis. Since Stimulated Emission Depletion microscopy has been revealed to allow the smallest Full-Width-at-Half-Maximum the following remarks are on this technique as the most presently realised, advanced are:

So far only a few fluorochromes useful for Stimulated Emission Depletion microscopy have been revealed. Here "STED-dyes" are called any fluorescent labelling procedures allowing the performance of Stimulated Emission Depletion—microscopy. The application of these "STED dyes" has been performed in a very limited number of cases.

To what extent the "STED dyes" can be used to label MacroMolecular Complexes and especially BioMolecular Machines or BioMolecular Modules without disturbing their structural identity is not known. To what extent "STED-dyes" can be used to label structures in living cell ("in vivo"), is also not known.

To what extent "STED-dyes" can be applied for simultaneous multispectral labelling is not known.

To what extent the "STED dyes" are toxic to the cells to be studied, especially in connection with the high incident light intensities needed for analysis, is not known.

To what extent the high number of laser light induced excitations of specific energy levels of the "STED dyes" needed to obtain the high optical resolution may lead to "bleaching" effects and thus to a significantly reduced count of registered fluorescent photons from a given site, is not known.

To what extent the labelling of MacroMolecular Complexes, especially of BioMolecular Machines or BioMolecular Modules with "STED dyes" is as easy to apply as the "conventional" fluorescence labelling strategies established e.g. in biology it is not known. This applies in particular to "in vivo" labelling schemes using methods of molecular genetic engineering, such as introducing genes for certain variants of "Green Fluorescent Proteins" (GFPs), i.e. proteins which by appropriate excitation show strong autofluorescence and which presently can be introduced having up to five spectral signatures [G. Patterson, R. N. Day, D. Riston, Fluorescent protein spectra, J. of Cell Science 114: 837-838]. Since each such spectral signature is encoded by an appropriate specific gene transfer, change of the label means a complete remaking of the molecular basis. This can take months of labour intensive work.

Present Stimulated Emission Depletion STED-microscopes require long scanning times, limiting the object volume to the 1 $\mu m^3$ range. A speed up in scanning velocity is possible by using multifocal devices. To what extent very large object volumes, e.g. in the order of 100×100×2 $\mu m^3$ can be scanned in a short time, e.g. a few seconds on a routine basis, is not known.

To what extent the technically complex opto-electronical devices required for Stimulated Emission Depletion microscopy can be used on a routine basis in a laboratory dedicated to applications such as polymer science, to cell biology, molecular biology, nuclear genome research, pharmaceutical or biomedical analysis, is not known.

To what extent the constructive interference in the focus of 4Pi-microscope devices can be maintained also in specimens with high refraction index variations it is not known.

Another method to determine the size of a BMM in a range comparable to the Full-Width-at-Half-Maximum of 4Pi/STED microscopy is Spectral Position Distance Microscopy. For example, if a BMM is analysed consisting of 8 "elements", where all of them are labelled with a different spectral signature, then the size of this BMM is analysed by inserting the Spectral Position Distance Microscopy determined positions of the 8 individual elements into a minimal enveloping sphere or ellipsoid. In addition, if the distance $d_j$ between the elements are equal or less than the topological resolution, the Spectral Position Distance Microscopy—method in this case will allow to reveal the "topology" of the BMM (see FIG. 1). Here, Topology is defined as the information concerning the relative positions (with regard to a given coordinate system) and mutual distances of the "elements" of a BMM, a MMC, or other complexes. The Spectral Position Distance Microscopy method described allows to determine the enveloping volume of any collection of N elements, as well as the size and the topology of any BMM/MMC consisting of N elements where each of the elements is labelled with a different spectral signature. Drawbacks of the Spectral Position Distance Microscopy—method are:

In many cases, conditions for correct size measurements by Spectral Position Distance Microscopy may be difficult to fulfil. For example, a BMM of 100 nm diameter may consist of 16 elements with 8 dimers; each dimer is labelled with a given spectral signature so that the entire BMM is labelled with 8 different spectral signatures; then by using Spectral Position Distance Microscopy, it is only possible (using conventional epifluorescence or Confocal Laser Scanning fluorescence Microscopy) to measure for each dimer the position of the joint fluorescence intensity barycenter (of the diffraction image maximum). If the arrangement of the dimer elements is symmetrical around a symmetry centre, then the Spectral Position Distance Microscopy—positions measured will coincide, independently of the actual size of the BMM (which would be obtained only if the 16 elements were labelled with 16 different spectral signatures).

Due to the labelling of more than one element with the same spectral signature (for the example see FIG. 2), the correct topological analysis is greatly impaired. Analogous problems occur wherever it is not possible to label all elements differently, especially where certain symmetries occur. This, however, is the case for many biologically important BioMolecular Machines or BioMolecular Modules, for example nuclear pores, ion-channels, or proteasomes. Referring to FIG. 2A if all the elements are labelled with different spectral signatures, the SPDM procedure allows to determine the topology (position and mutual distances of the elements 1, 2, 3, 4) also in the case that the mutual distances are smaller than the FWHM. Referring to FIG. 2B, assuming a symmetrical arrangement of the element pairs, each pair labelled with spectral signature specs 1, i.e. the elements 1a and 1b labelled with spectral signature specs 1, the elements 2a and 2b labelled with spectral signature specs 2, the SPDM —determined fluorescence intensity gravity centers or also called barycenter or diffraction image maxima coincide in the center denoted with x independently of the actual diameter of the minimum enveloping volume.

The higher the number of spectral signatures to be used for size or topological analysis, the more difficult the application of the method becomes, both in terms of specific and complete fluorescence labelling, and in terms of spectrally discriminated registration and calibration. Whereas the simultaneous use of 4-7 spectral signatures is still relatively straightforward, a Spectral Position Distance Microscopy analysis of e.g. 16 spectral signatures will be technically very demanding. As a consequence, the lower the number of spectral signatures required to solve a given problem of size or topology analysis, the more facilitated the measurement will be.

As a consequence of the drawbacks of the state of the art, additional methods are needed to allow to facilitate Far Field Light Microscopy size and topology analysis also in those cases where the revealed methods are difficult or impractical to apply, and with the minimum number of spectral signatures to solve a given problem with a given microscope technique.

SUMMARY OF THE INVENTION

The above object is solved by a far field light microscopical method according to claim 1, a far field light microscopical system according to claim 18. Preferred embodiments are subject of the dependent claims.

According to the invention, there is provided a far field light microscopical method for analysing at least one object having a subwavelength size in at least one spatial direction to obtain spatial information of the object, in particular size and topology thereof, comprising the steps of:

labelling the object(s) with one or more suitable optical markers;
providing suitably structured illumination light to at least partially illuminate the object(s);
subjecting the object(s) to the structured illumination light;
detecting an optical response of the object(s);
obtaining the spatial information of the object(s) by comparing the obtained response with simulation data of an optical response of object(s) having known spatial information.

The present invention adds to the possibilities to measure quantitatively the spatial information and, respectively spatial structure and dynamics of a wide range of subwavelength objects or complex nanosystems. The possibility to measure topological and morphological parameters made possible by the invention allows also new approaches in modelling and simulation of subwavelength sized objects. In combination with other methods for analysis of the topology, such as Spectral Position Distance Microscopy, the invention considerably extends the possibilities of the topological analysis.

The present invention allows furhter to improve in particular the size and topology analysis of Micromolecular Complexes (MMCs), especially of BioMolecular Machines or BioMolecular Modules (BMMs) by using Spatially modulated illumination (SMI) microscopy, as well as other sources of structural illumination, in combination with special calibration procedures obtained by virtual microscopy (VIM) based specially designed information technology tools. Further it can be applied to measure the size of any fluorescent object, in a direction where this size is below a certain limit, which for visible light is in the order of 200 nm, and for infrared light correspondingly larger. The minimum detectable size diameter depends on the special optical conditions and may be as small as 20 nm and less.

According to a preferred embodiment the spatial information comprises at least one of the following information:
size of the object in at least one spatial direction;
topology of the object in at least one spatial direction;
distance(s) between at least two objects in at least one spatial direction;
size and topology of an enveloping ellipsoid and/or the topology of the elements comprising the object and producing such enveloping ellipsoid;
position of an intensity barycenter of a fringe pattern of the optical response in at least one spatial direction;
size, topology and arrangement of the sequence of elements comprising the object in at least one spatial direction.

Preferably, the spatial information is the information about the size and topology of subwavelength sized objects, such objects being in particular polymeric structures and supramolecular complexes composed of several to many "elements" fluorescence labelled with an appropriate number of one or more spectral signatures, or any other fluorescent structures, having a subwavelength size at least in one spatial direction, by using Spatially modulated illumination (SMI) microscopy or other methods providing suitably structured illumination (SI) in the object space, in combination with special calibration procedures, obtained by virtual micrsocopy (VIM) based specially designed information technology tools. In particular the size of subwavelength sized extended fluorescent objects is determined, even if they are fluorescence labelled with a minimum of one optical marker, or in other words with a minimum of one spectral signature only, and to determine their topology if labelled with than one optical marker, i.e. with more than one spectral signature.

According to a further preferred embodiment of the invention in the step of labelling the object with a plurality of markers:
the optical markers are all the same;
at least two of the optical markers are different;

pairs of different optical markers are used;
all of elements of the object are labelled with a first optical marker, and the elements within are labelled with at least one second optical marker, different from the first optical marker; and/or
the object is labelled with a linear sequence of optical markers.

According to still another embodiment of the invention a modulation contrast of an intensity distribution of the light returned from the object is detected and preferably compared with simulated data of the modulation contrast of the intensity distribution.

According to one more embodiment of the invention the optical marker(s) comprise fluorescent marker(s) and the optical response of the, object is an intensity distribution of the emitted light from the fluorescent markers.

Preferably the objects to be analysed are being subjected to fluorescence registration excited by spatially modulated illumination or other kinds of suitable structured illumination, the resulting data being interpreted by calibration procedures obtained by preferably virtual microscopy tools of Spatially Modulated Illumination (SMI) microscopy, or other suitable kinds of SI, designed in such a way as to determine in a quantitative way the optical response of the labelled objects, in particular the disturbance which small fluorescent objects or elements with a size or diameter below a certain limit below the wavelength of the illuminating light exercise on the modulation contrast R of the Spatially Modulated Illumination/Structured Illumination SMI/SI-fluorescence-intensity-diffraction images allowing the determination of quantitative calibration functions for the evaluation of the modulation contrast R, as preferably a function of exciting wavelength, emitted wavelength, fluorescence life time, refraction index of the transparent media in the optical light path, parameters describing the SMI-intensity or any other suitably light intensity distribution in the object space, or any other parameter describing spectral signature, numerical aperture of the fluorescence light collecting objective lens or objective lenses, of the point spread function of the microscopic system, the photon count statistics, the read out noise of the camera, other noise sources, chromatic and monochromatic aberration, or any other relevant optical features which can be described by an algorithm executable with a digital computer system.

According to another embodiment the illumination light has such a wavelength that the optical markers are excited by an one-photon process.

The far field light microscopical method may use illumination light with especially One-Photon excitation wavelengths down to 360 nm, to allow the minimum detectable object size different from a "point like" object to be in low photon count condition 20 nm, e.g. for a registered total number of 10,000 photons. Preferably, the One-Photon excitation wavelengths in the visible light range between 400 nm and 700 nm, to allow the maximum detectable object size to be around 200 nm. Further preferably, the One-Photon excitation wavelengths in the infrared light range above 700 nm, to allow the maximum detectable object size to be larger than 200 nm. Still further preferably the excitation wavelengths are in the shorter ultraviolet range below 360 nm, by which also smaller minimum object sizes than 20 nm are detected in low photon count conditions, using a minimum of one spectral signature for the labelling of the object.

According to still another embodiment the illumination light has such a wavelength that the optical markers are excited by a two-photon or multiphoton process and wherein the step of labelling comprises labelling the object with more than three different optical markers simultaneously.

Preferably more than three spectral signatures may be used simultaneously, realised by producing a spatially illumination modulation or otherwise structured illumination produced by light intensities resulting in two photon or multiphoton fluorescence excitation of the molecules carrying the spectral signatures. Further preferably, the method comprises a step of blocking the transmittance of the exciting wavelength to the detector system or detector systems, and measuring the intensity of the fluorescence emission having a shorter wavelength than the exciting laser light.

Further preferably, especially more than three spectral signatures may be used simultaneously, realised by a spatially modulated illumination microscope, producing multiwavelength excitation resulting in One-Photon, Two-Photon or multiphoton fluorescence excitation of the molecules carrying the spectral signatures; in the excitation light path after the reflection of the exciting laser beam or laser beams a microlens or microlens system with a diameter considerably smaller than the diameter of the collimated fluorescence emission is used to focus the exciting laser beam or laser beams into the back focal plane or planes of the above mentioned objective lens or objective lenses by selecting for example appropriate filters or other wavelength separating means the fluorescence emission wavelengths for detection, after the collimated fluorescence light passed the above mentioned mirror or mirrors. For example, if the micromirrors and microlenses mentioned above to reflect and focus the exciting laser beam(s) have a diameter of 1 mm, and the collimated fluorescence emission beams have a diameter of 6 mm, then the losses of the fluorescence emission intensity are in the order of a few percent only. The advantage of this is that simultaneous multiwavelength excitation of a spatially modulated illumination field is possible for any wavelength without the necessity to change the mirrors in the excitation light path.

According to another embodiment of the invention the structured illumination is a spatially modulated illumination, still further preferably realised in at least:
one or more directions in a plane containing the object and/or
direction substantially perpendicular to the object;
The method may be also applied to measure the lateral extension of MMCs, by using spatially modulated or structured illumination producing a modulation of excitation light intensity in one, or more direction in the object plane. Further preferably, a spatially modulated or structured illumination producing simultaneously and sequentially a modulation in the lateral and axial direction may be used.

The method further may use preferably any suitably structured illumination in which in the object space in the axial (z) direction and/or in the lateral (x,y) direction, or in any other direction, wherein preferably an illumination light intensity distribution is produced the fluorescence image of which is disturbed by small, subwavelength sized objects in an analogous way as it is the case using spatially modulated illumination. The general method to obtain in such a case the structural information's described above is the same as described in the invention.

Still further preferably, the far field light microscopical method is characterised especially by the circumstance that instead of using axial tomography approaches, in addition to the axial (z) direction described in detail in the invention, the spatially modulated illumination or any other kind of suitably structured illumination is realised also in the lateral x,y plane or any other additional plane as disclosed in DE 198

30 596 A1; J. T. Frohn, H. F. Knapp, A. Stemmer: True optical resolution beyond the Rayleigh limit achieved by standing wave illumination. Proc. Natl. Acad. Sci. USA 97 7232-7236 (2000); J. T. Frohn, H. F. Knapp, A. Stemmer: Optics letters 26:828-830(2001), included herein by reference.

The minimum detectable size or diameter of an object which can be discriminated from a "point like" object is called "size resolution". In the description, methods to obtain a size resolution of about 20 nm in the axial (z) direction have been presented. The application of this invention to obtain a still better size resolution by using a smaller excitation wavelength, or to obtain an analogous size resolution also in the direction of the object plane, or in any other spatial direction is a direct extension of the invention.

Preferably, the axial extensions of MMCs in a two-dimensional array, such as nuclear pores or ion-channels in a membrane are measured.

According to a preferred embodiment of the invention, it comprises the step of obtaining information about the sub-wavelength distance between two adjacent layers, wherein the layers may comprise thin extended elements in a given part of the layers equal or larger than the optical resolution, and the step of illuminating, such that the structured illumination is realised in the direction substantially perpendicular to the layers in this part and wherein the step of labelling comprises at least one of:

labelling the space between the adjacent layers with a minimum of one optical marker;

labelling the layers with a first optical marker, whereas the space between is labelled with another optical marker, or not labelled at all; and/or labelling the layers with the same optical marker as used to label the space within, or additionally with other optical markers not related to the distance measurements.

Preferably the method may be specially applied to measure a small distance between the cell membranes/layers of two neighbouring cells in a given part of the cell membranes equal or larger to the optical resolution, especially equal or larger than 200 nm. Preferably, the molecules in the space between the adjacent cell membranes are labelled with a minimum of one spectral signature, and the cells are oriented in such a way that the spatially modulated illumination is realised in the direction perpendicular to the membrane in this part, or using another angle suitable to produce a modulation contrast according to the invention. In this case, preferably the modulation contrast R of the SMI/SI-fluorescence-intensity-diffraction-image is modified depending on the distance between the cell membranes. Accordingly, the thickness of the fluorescent layer between the two cell membranes in the section analysed is determined down to 20 nm and less, using in the latter case ultraviolet light for excitation.

Further preferably, the adjacent membranes/layers are labelled with one spectral signature A, whereas the space between is preferably labelled with another spectral signature B, or not labelled at all, and the cells or layers are oriented in such a way that the spatially modulated or otherwise structured illumination is realised in the direction perpendicular to the membrane/layer in this part, or using another angle suitable to produce a modulation contrast. In this case, preferably the modulation contrast R of the SMI/SI-fluorescence-intensity-diffraction-image is modified depending on the distance between the cell membranes or layers; the thickness of the space between the two cell membranes/layers in the section analysed is determined down to 20 nm and less, using in the latter case ultraviolet light for excitation.

Still further preferably, the molecules in the space between the adjacent layers/cell membranes are labelled with a minimum of one spectral signature, and the layers are oriented in such a way that the spatially modulated illumination or any other kind of suitable structured illumination is realised preferably in the direction perpendicular to the membrane in this section. In this case, preferably the modulation contrast R of the Spatially Modulated Illumination/Structured Illumination SMI/SI fluorescence-intensity-diffraction image is modified depending on the distance between the layers or cell membranes, the thickness of the fluorescent space between the two layers in the section analysed is determined down to 20 nm and less, using in the latter case ultraviolet light for excitation. In a still another embodiment, the adjacent layers or cell membranes are labelled with the same spectral signature as used to label the space within, or additionally with other spectral signatures not related to the distance measurements.

According to a preferred embodiment of the invention, the step of labelling the object comprises labelling at least one pair of point like elements of the object with the same optical markers and further comprising the step of obtaining at least the distances between the point like elements;

the distance between elements labelled with the same spectral signature using a-priory information that there are only two such elements labelled with the same spectral signature; and/or the topology of the point like elements, especially in combination with Spectral Position Distance Microscopy, axial tomographic tools or other methods of spatially modulated or otherwise structured illumination;

Far field light microscopical method can be applied especially to the determination of small distances between pairs of "point like" elements labelled with the same spectral signature. This is achieved by calibrating the disturbance of the SMI/SI-fluorescence intensity diffraction image. For the excitation wavelength range of 360-650 nm, "small distances" are distances below 200 nm; for distances larger than 200 nm, appropriately longer excitation wavelengths are used; for each distance measurement problem, the useful excitation wavelengths and other relevant optical parameters are determined by virtual microscopy analysis according to the invention. In particular the method may be applied especially to the determination of small distances below 200 nm between layers of thin extended elements labelled with the same spectral signature, again using the disturbance of the SMI/SI-fluorescence intensity diffraction image in combination with calibration by SMI/SI-VIM.

Far field light microscopic methods may be applied, especially to analysing two or more elements within an object, e.g. a MMC, being labelled with different spectral signatures, allowing in combination with Spectral Position Distance Microscopy—methods to determine both the sizes and the relative positions and mutual distances of these elements (FIG. 4, 8, 9).

In the labelling step the object to be analysed may be preferably labelled using more than one spectral signature. In particular, preferably the overall size of a MMC is determined by labelling all of its elements with a spectral signature specs 1; the sizes of elements within is determined by labelling these with other spectral signatures specs 2, specs 3, specs 4.

Far field light microscopical method can be applied further especially to the case that in an object, preferably MMC, "point like" elements are a) labelled with the same spectral signature, and b) it is known from other information that there are only two such elements labelled with the same spectral signature, where using the invention the distance between these elements labelled with the same spectral signature is determined even if it is much smaller than 200 nm.

Far field light microscopical method may be further especially applied to determine the position of the elements producing such an "enveloping size ellipsoid", wherein the minimum half axis of the "enveloping size" ellipsoid is given by half the minimum size determined by the invention procedure for any spatial direction; the maximum half axis of the "enveloping size ellipsoid" is given by half the maximum size determined by the invention procedure for any other direction. It can be applied preferably to the case that any "point-like" objects are with a subwavelength distance smaller than 200 nm; for example, using the prior knowledge that the "enveloping size ellipsoid" is produced by a pair of elements labelled with the same spectral signature.

Far field light microscopical method can be applied according to another embodiment especially to the case that in an object, preferably MMC, pairs of "point like" elements are each labelled with a different spectral signature, while each pair carries the same spectral signature, to allow in combination with Spectral Position Distance Microscopy to determine the relative positions of all labelled "point like" elements. For example, instead of 16 spectral signatures required to resolve a given topology of a MMC containing 16 elements, the use of the invention allows to obtain equivalent topological information using 8 spectral signatures only. In combination with axial tomographic tools for example disclosed in J. Bradl, M. Hausmann, B. Schneider, B. Rinke, C. Cremer, A versatile 2pi-tilting device for fluorescence microscopes. J. Microscopy 176: 211-221 (1994); R. Heintzmann, G. Kreth, C. Cremer, Reconstruction of axial tomographic high resolution data from confocal fluorescence microscopy. A method for improving 3D FISH images. Analytical Cellular Pathology 20: 7-15 (2000), or other methods of spatially modulated or otherwise structured illumination e.g as disclosed in DE 19830596; J. T. Frohn, H. F. Knapp, A. Stemmer: True optical resolution beyond the Rayleigh limit achieved by standing wave illumination. Proc. Natl. Acad. Sci. USA 97 7232-7236 (2000); J. T. Frohn, H. F. Knapp, A. Stemmer, Optics letters 26:828-830 (2001) the extension of a non spherical extended fluorescence labelled object in the three directions of space, e.g. the half axes of a minimal enveloping ellipsoid, can be determined by using the invention. In addition, if a MMC to be analysed contains two non spherical extended elements, each labelled with a different spectral signature, in combination with axial tomography or other methods of structured illumination the invention allows to determine the relative rotation angles between the half axes of the enveloping ellipsoids of the two extended elements.

According to another embodiment of the invention, the step of labelling comprises labelling the object so that a distance(s) between optical markers are smaller than the Full-Width-at-Half-Maximum of the intensity fringes (FWHM$_f$) of the spatially modulated illumination, and further comprising the step of obtaining the distance between the elements of each pair, the position of the fluorescence intensity barycenter of each pair, and/or the relative rotation angles between vectors given by the connecting lines between the centres of the elements of each pair labelled with the same spectral signature and the step of evaluation of this information using geometrical considerations.

Far field light microscopical method can be applied further applied especially to the case that a MMC to be analysed contains two or more pairs of "point like" elements with a small distance, such as a distance smaller than the Full-Width-at-Half-Maximum of the intensity fringes FWHM$_f$ of the spatially modulated illumination, to allow to determine for example the distance between the elements of each pair, the position of the fluorescence intensity barycenter of each pair, and the relative rotation angles between vectors given by the connecting lines between the centres of the elements of each pair labelled with the same spectral signature. Evaluation of these information using geometrical considerations according to the state of the art allows then to determine the relative positions and distances of all individual "point like" elements in the MMC. In case the distance is larger than to be determined with the invention using visible light excitation wavelengths, infrared light with an appropriate wavelength is used, such as the light emitted by a Ti:Sa-Laser system, or other laser sources emitting coherent infrared light.

Far field light microscopical method can be applied especially to the case of an object (preferably a MMC) with elements forming pairs labelled with the same spectral signature, such "elements" are not "point like". The method can be applied for size and topology evaluation as described, as long as the diameter of the minimum enveloping "size ellipsoid" of the pair does not exceed the size range where under the SMI/SI conditions used, modulation contrast according to the invention occurs. For the examples used in the description for visible light excitation (about 0.4-0.7 µm, this means that the size/diameter of the individual elements should not exceed 200 nm. In cases of larger sizes, conditions allowing a modulation contrast can be realised according to the invention by using longer excitation wavelengths as indicated in a previous claim.

According to one more embodiment of the invention, the step of labelling the object comprises a labelling a plurality of elements (E1, E2, E3 . . . E$_N$) each element with a subwavelength size, such that the entire sequence being within the limits of conventional optical resolution and each element is labelled:
  with all elements of the sequence labelled with different optical markers or
  with at least two elements of the sequence are labelled with the same optical markers or
  randomly, wherein all the optical markers are different or
    randomly, wherein the object is labelled with pairs of different optical markers.

According to a preferred embodiment of the present invention, the far field light microscopical method can be used to determine the topology, in particular the arrangement of a linear sequence of "different elements" with a size allowing size measurements according to the invention, wherein the entire sequence is being within the limits of conventional optical resolution and in particular if the end-to-end distance of the arrangement is smaller than 200 nm if illumination (preferably excitation) wavelengths in the visible range are used. If maximum distances are larger, such as 300 nm, infrared light can be used for excitation. In this respect "different elements" are elements E1, E2, E3 . . . E$_N$ which can be optically labelled, preferably fluorescence labelled specifically for example by reporter molecules. Instead of using N different spectral signatures for labelling as in Spectral Position Distance Microscopy methods according to the state of the art, half the number (N/2) of spectral signatures is used here. Two elements are labelled in pairs with the same spectral signature, to the discretion of the applicant.

Furthermore, the far field light microscopical method according to still another embodiment may be used to determine preferably the three-dimensional arrangement of an object, preferably a MMC, composed of "different elements" with a size as described above, the entire MMC being within the limits of the conventional microscopical epifluorescence observation volume given by an ellipsoid with the half axes $FWHM(x,y)_{EPI}/2$ and $FWHM(Z)_{EPI}/2$, where $FWHM(x,y,z)_{EPI}$ are the FWHMs of the Point Spread Function of the conventional epifluorescence microscope in x,y, and z direction, respectively. The method can be used in particular if the diameter of the minimum enveloping volume of the arrangement is smaller than 200 nm. Instead of using N different spectral signatures for labelling as in Spectral Position Distance Microscopy methods according to the state of the art, half the number (N/2) of spectral signatures is used. Two elements are pairwise labelled with the same spectral signature. In case the number N of the elements is uneven, N/2+1 spectral signatures are used. In this case, for the remaining element detected with the additional spectral signature, the application of the method allows to determine the position and in case of a size larger than the size resolution, the size. Generally, in a MMC composed of pairs of elements having the same spectral signature and single element with a spectral signature different from the other single elements and pairs of elements in the MMC, the invention allows to determine the position and the size of the single elements, in addition the position and the mutual distances of the elements pairs. The method described above can be preferably used for the topology analysis of the pairs of elements.

Furthermore, according to still another embodiment, far field light microscopical method can be used to determine the arrangement of a MMC with a linear sequence or the three-dimensional arrangement of an object, preferable a MMC, containing N "equal elements" with a size described above, the entire MMC being within the limits of conventional optical resolution, in particular if the end-to-end distance of the arrangement is smaller than 200 ml. "Equal elements" are elements $E1, E2, E3 \ldots E_N$ which cannot be identified individually by differential binding of the optical markers, preferably of the reporter molecules applied. In particular, equal elements are proteins of the same aminoacid sequence and 3D-structure, or nucleic acids with the same DNA sequence, or any other polymeric molecules with the same type of subunits or "elements". Individual identification means that an optical marker, preferably a reporter molecule with a spectral signature 1 binds specifically to element 1; a reporter molecule with a spectral signature 2 binds specifically to an element 2, etc. In the case of equal elements, an optical marker, preferably a reporter molecule with a spectral signature 1 can bind to element 1, or to element 2, or to element 3, . . . etc. According to an embodiment of the invention, in this case the spatial arrangement ("topology") is determined by a) bringing the MMC in contact with a liquid mixture of reporter molecules specific for the equal elements, with N/2 different spectral signatures, each reporter molecule having one spectral signature only, the reporter molecules being e.g. fluorescence labelled nucleic acid aptamers, or other fluorescence labelled nucleic acids, or fluorescent proteins, or any other fluorescence providing molecules with one binding site on an element only; b) allowing one reporter molecule to be bound to each element only, conferring a label with one of the N/2 spectral signatures at random; c) identifying by far field light microscopical means, in particular by SMI/SI-microscopy, the MMCs labelled in the way useful for LIMON-analysis. Such a "useful" MMC-label is characterised in particular by displaying N/2 different spectral signatures in each MMC, each spectral signature intensity not being larger than twice the intensity displayed by one equal element bound to a reporter molecule with this spectral signature; c) performing the LIMON analysis in the way as described above. The method described applies also to the case that a MMC containing the N equal elements, containing in addition other elements to which the reporter molecules binding the equal elements do not bind. This is a situation very often encountered in BMMs.

Far field light microscopical method can be used furthermore to determine the spatial arrangement, for example the linear or two-dimensional, or three-dimensional arrangement of objects, preferably MMCs of equal type if the distance between the MMCs is smaller than the optical resolution. Such objects, respectively MMCs of equal type are for example MMCs composed of the same elements, such as chromatin fibers containing the same sequences, transcription factories of a given type, nuclear pore complexes of a given type, ion-channels of a given type, proteasomes or ribosomes, of a given type, or any other MMCs which cannot be identified specifically by reporter molecules. The linear or two-dimensional arrangement of the MMCs of equal type can be determined by a) bringing the MMCs in contact with a liquid mixture of reporter molecules specific for the equal MMCs, e.g. to one of the elements they are composed of, with N/2 different spectral signatures, the reporter molecules being e.g. fluorescence labelled nucleic acid aptamers, or specific antibodies, or any other type of fluorescence labelling fit to the purpose; b) allowing one reporter molecule bearing one spectral signature to be bound to each MMC only; c) identifying by far field light microscopical means the MMCs labelled in the way useful for the application of the invention. Such a "ueful" MMC labelling is characterised by displaying the signals of N/2 different spectral signatures within the observation field or observation volume given by the optical resolution, each spectral signature intensity not being larger than twice the intensity displayed by one equal element bound to a reporter molecule with this spectral signature; d) performing the analysis as described in one or several of the previous claims. In particular, the claim refers to linear, two-dimensional, or three-dimensional arrangements having not more than 14 equal MMCs in the observation field/observation volume given by the optical resolution. For example assuming as an estimate for the probe density P of a "useful" MMC labelling $P \geq \{(N/2)!\}^2/\{(N/2)^N\}$, $P(N=14) \geq 3.7*10^{-5}$ follows, using e.g. nanolithographically produced arrangements as disclosed in DE 100 52 823 included herein by reference, even such a low probability can be handled advantageously: in such a nanolithography produced pattern of MMCs, in one far microscopical field of view, e.g. of an SMI/SI microscope, up to about $10^4$ MMCs can be arranged in such a way that the SMI/SI measurements can be performed. Since evaluation procedures are executable in a fully automatic way, the analysis of $10^4$ or more MMCs technically is feasible. The lower N, the higher the probability of a useful MMC labelling e.g. $P(N=12) \geq 2.4*10^{-4}$, $P(N=10) \geq 1.5*10^{-3}$, $P(N=8) \geq 0.8*10^{-3}$, $P(N=6) \geq 0.05$, $P(N=4) \geq 0.25$. For example, if in the deconvolution volume 8 MMCs are found, about 1% of MMCs will have a useful labelling, displaying N/2 each with a different spectral signature. Such a condition may apply e.g. to the distribution of cell nuclear pair complexes in a membrane. Since the nuclear membrane of a cell may contain a total of several thousands of such nuclear pore complexes, even analysing the nuclear pore complexes in one cell only, a number of "useful" labelling according with the claim may be found. In addition, all MMCs not fulfilling this complete "pair wise labelling" condition but displaying spectral signature intensities corresponding in one or more cases to the labelling of a single element in a MMC only, may be used to obtain information in particular on the size of the elements labelled.

In still a further embodiment, the far field light microscopical method may be used to determine the distances between equal MMCs if this distance is smaller than 300 nm. This can be performed for example by a) bringing the MMCs in contact with a liquid mixture of reporter molecules specific for the equal MMCs, e.g. to one of the elements they are composed of, with a number of different spectral signatures; the reporter molecules being e.g. fluorescence labelled nucleic acid aptamers, or specific antibodies, or any other of fluorescence labelling fit to the purpose; b) allowing only one reporter molecule bearing one spectral signature to be bound to each MMC; c) identifying by far field light microscopical means in the SMI/SI-fluorescence intensity diffraction images pairs of MMCs labelled with the same spectral signature, and occurring once only in the light microscopic observation volume; this selection is possible by selecting those images which have the fluorescence intensity fitting to a pair; d) performing the analysis for size and topology as described in the previous claims. If the modulation contrast R is too low to allow a proper distance analysis, the excitation wavelength is changed accordingly. Basic combinatorial considerations show that using a proper number of different spectral signatures, such as 4 or 5 or 6, a considerable percentage of MMCs within the volume consists of pairs with a given spectral signature, allowing size and topology measurements.

According to another embodiment of the present invention, the step of labelling comprises labelling in the object a plurality of linear sequence arrangements of elements L1s1s2s3 . . . sn; L2s1s2s3 . . . sn; L3s1s2s3 . . . sn; LNs1s2s3 . . . sn, such that si, i=1, 2, . . . ,n, is realised either by an element $S^0$ representing the binary code 0, or by an element $S^1$, representing the binary code 1 and wherein the element $S^0$ binds to a first optical marker, the element $S^1$ binds to a second optical marker and the starting element L1 binds third optical marker, the starting element L2 binds to a fourth optical marker, etc.;

the individual sequence arrangements have a mean distance from each other larger than or equal to the optical resolution of the optical system used for analysis;

the far field light microscopical method further comprising the step of determining the at least one-dimensional sequence arrangement, the size and the topography of the linear sequences.

Preferably, the far field light microscopical method according to still another embodiment may be used to determine the sequence arrangement in a Bar-Code type linear sequence, preferably in a DNA-"Bar Code" or any other Polymer "Bar Code" or MMC "Bar Code". Here a Bar Code is a linear sequence, wherein a) the sequence arrangements being composed of elements L1s1s2s3 . . . sn; L2s1s2s3 . . . sn; L3s1s2s3 . . . sn; LNs1s2s3 . . . sn in a linear way, such that si is realised either by an element $S^0$ representing the binary code "0", or by an element $S^1$, representing the binary code "1", L and n being in particular smaller or equal to 5. b) An element sequence s1, s2, s3 . . . representing a decimal number in binary code, e.g. "00000, 00001, 00010, . . . 11111" is constructed in such a way that each si dedicated to represent "0" in the binary code is realised by the element $S^1$, in such a way that it specifically binds to an optical marker, preferably a reporter molecule, with spectral signature 1; Each element sk dedicated to represent "1" in the binary code is realised by the element $S^1$, in such a way that it specifically binds to an optical marker, preferably a reporter molecule with spectral signature 2. Appropriate elements $S^0$ and $S^1$ can be realised in many different ways, according to the state of the art, e.g. using nucleic acid oligosequences, or oligopetide sequences. c) The starting element L1 is constructed, in such a way that it binds specifically to a optical marker 3, e.g. spectral signature 3. The starting element L2 is constructed in such a way that it binds specifically to a spectral signature 4, etc. Appropriate starting elements can be constructed in the same way as $S^0$ and $S^1$. d) The sequence arrangements L2s1s2s3s4s5 . . . sn are displayed in whatever medium designated for identification in such a way that the individual sequence arrangements have a mean distance from each other larger than or equal to the optical resolution of the SMI-system used for analysis, in particular a mean distance either larger than 200 nm in the lateral (x,y) direction, or larger 1 µm in the axial direction. This can be achieved by using an appropriate dilution. e) For Bar Code analysis, the sequence arrangements are subjected to labelling with reporter molecules with spectral signatures specific for L1, L2, . . . , and $S^0$ and $S^1$, respectively. The topological analysis according to the invention is performed as described above, with the exception, that in this case, more than two elements s1s2 . . . can be labelled with the same spectral signature. In cases with not more than 5 elements s1s2s3s4s5 . . . , the topological analysis of size and fluorescence intensity barycenter position by application of the invention allows to determine unequivocally whether a given element si at a given position i represents $S^0$ (for binary code "0"), or $S^1$ (for binary code "1" d) Sequence arrangements labelled with L1 represent the binary code for the first 5 binary digits for decimal numbers 0, 1, 2, 3, . . . 31; two types of sequence arrangements labelled with L1 and L2, respectively, represent 10 digits of the binary code, allowing the encoding and detection of decimal numbers from 1 to 1023, the encoding being done in such a way that the first 5 binary digits are encoded in the sequence arrangement starting with L1, and the following 5 binary digits are encoded in the sequence arrangement starting with L2; three types of sequence arrangements labelled with L1 for the first 5 binary digits, with L2 for the second 5 binary digits, and with L3 for the third 5 binary digits allow the encoding and detection of decimal numbers from 1, 2, 3 . . . , $2^{15}-1=32767$; four types of sequence arrangements labelled with L1 for the first 5 binary digits, with L2 for the second 5 binary digits, L3 for the third 5 binary digits, and L4 for the fourth 5 binary digits allow the encoding and detection of decimal numbers from 1, 2, 3 . . . , $2^{20}-1=1048575 \approx 10^6$, etc. Using the invention according to one or several of the previous claims together with this kind of label procedure, about 1 Million decimal numbers may be encoded using 6 spectral signatures for light microscopical detection according to the invention. Using e.g. 8 spectral signatures for L1 . . . L6, $S^0$ and $S^1$, 6×5=30 digits representing decimal numbers up to $2^{30}-1=1073741823 \approx 10^9$ may be encoded. To encode the same decimal numbers by combinatorial labelling, 20 different spectral signatures would be needed in the first case, and 30 different spectral signatures would be needed in the second case. For a schematic example see FIGS. (5, 10).

According to a one more embodiment, when determining the size of a fluorochrome object and comprising the step(s) of:
  determining the fluorochrome density of objects by comparing the determined size with a size of the object determined by other means than far field light microscopical methods and/or
  determining the average time in which the fluorochrome object(s) lose their homogeneity properties by applying several statistical measurements of the objects after different time intervals.

Preferably, another application of the far field light microscopical method is to determine the fluorochrome density of artificial microspheres or beads having the size (diameter S) determined by other means than far field light microscopical methods but in which the "effective fluorescence size" as determined by the invention procedure strongly depends on the homogeneity of the fluorochrome in a way that an extended object covered not homogeneously by the fluorochrome appears like an object with an "effective fluorescent size" smaller than the sphere/bead size determined by other means, or like a superposition of several smaller fluorescent objects. Further, preferably applying several statistical measurements of the objects extracted from the same preparation after different time intervals can be used to calibrate the decay time, i.e. the average time in which the particles of the above claim lost their homogeneity properties.

According to another preferred embodiment, wherein the object is an extended object comprising a plurality of point like elements symmetrically or not symmetrically distributed within the object with respect to the fringe barycenter and comprising the step(s) of:
  determining the position of the barycenter of a fluorescent object with respect to the barycenter of the fringe pattern;
  determining how the position of the barycenter of an extended homogeneous fluorescent object with respect to the fringe pattern barycenter changes in different time acquisitions; and/or
  determining the time and space stability of the laser illumination used in the step of providing suitably structured light by measuring how the position of the barycenter of an extended homogeneous fluorescent object changes with respect to the fringe pattern barycenter in different time acquisitions and in different illumination conditions.

Preferably, the far field light microscopical method may be used to improve the nanotopological analysis of MMCs determining the position of the barycenter of a fluorescent object with respect to the barycenter of the fringe pattern, using appropriate calibration functions and considering extended objects like the superposition of several "point like" objects symmetrically or not symmetrically distributed with respect to the fringe barycenter. In another embodiment, the far field light microscopical method may be used to calibrate a spatially modulated/structured illumination far field light microscope by measuring how the position of the barycenter of an extended homogeneous fluorescent object with respect to the fringe pattern barycenter changes in different time acquisitions.

Preferably, the far field light microscopical method may be used to determine in a SMI microscope or any other SI microscope set up, the time and space stability of the laser illumination used by measuring as in a claim above how the position of the barycenter of an extended homogeneous fluorescent object changes with respect to the fringe pattern barycenter in different time acquisitions and in different illumination conditions.

According to one more embodiment of the invention, the far field light microscopical method comprises the step of visualising online on a monitor the fluorescence intensity distribution wherein any region of interest can be preferably marked interactively by a computer pointer and displaying the axial and the lateral fluorescence intensity distribution registered in this region of interest.

Furthermore. Far field light microscopical method, respectively a system can be combined with special software tools, to visualise "online" on a monitor the fluorescence intensity distribution, in such a way that after the registration of the SMI/SI data set, a lateral projection image is produced, in which any region of interest can be marked interactively by a computer pointer, displaying then the axial and the lateral fluorescence intensity distribution registered in this region of interest.

Preferably the method is used for size and topology analysis of preferably MacroMolecular Complexes, especially of BioMolecular Machines or BioMolecular Modules by using preferably Spatially modulated illumination microscopy, as well as other sources of structural illumination in combination with special calibration procedures obtained by Virtual Microscopy based specially designed information technology tools. Generally, the method can be applied to measure the size of any fluorescent object, in a direction where this size is below a certain limit, which for visible light is in the order of 200 nm, and for infrared light correspondingly larger. The minimum detectable size diameter depends on the special optical conditions and may be as small as 20 nm and less. Far field light microscopical method can be also applied especially to the analysis of MMCs, e.g. BMMs. In addition, it relates to all microscopic structures or objects where the invention described to determine size is applicable, such as the thickness of fluorescence labelled specimens; the distance between fluorescence labelled cellular or other membranes; the distance between non-fluorescent cellular and other membranes, where the space between is filled with a fluorescent substance; the size and topology of polymeric structures used in material sciences and their applications, or used in computer sciences and their applications applying organic polymeric molecules. Where the invention for convenience is referred to MMCs or BMMs only, these other cases are included without being mentioned explicitly.

According to the invention there is further provided a far field light microscopical system to obtain information of the spatial structure of the objects labelled with optical markers comprising:
  an illumination optical system capable of providing suitably structured illumination light to at least partially illuminate the object(s);
  a detection system to detect the light returned from the object;
  an evaluation system to evaluate the detected data using simulated data of the optical response of the object.

According to a preferred embodiment the illumination system is capable of providing a spatially modulated light.

According to a further preferred embodiment, the optical markers are fluorescence markers and wherein the illumination system is capable of providing light with a wavelength so as to excite the fluorescence markers by a one-photon process and/or multi-photon process.

According to one more preferred embodiment, the illumination system is capable of providing
- a structured light modulated in one or more directions in the object plane;
- a structured light simultaneously and sequentially modulated in the lateral and axial directions; and/or
- providing structured light modulated in a direction perpendicular to the object plane.

According to still another preferred embodiment, the evaluation system is capable of evaluating:
- size of the object in at least one spatial direction;
- topology of the object in at least one spatial direction;
- distance(s) between at least two objects in at least one spatial direction;
- size and topology of the enveloping ellipsoid and/or the topology of the elements comprising the object and producing such ellipsoid;
- position of an intensity barycenter in at least one spatial direction; and/or
- size, topology and arrangement of the sequence of elements comprising the object in at least one spatial direction.

According to still one more preferred embodiment, the illumination and detection system are integrated and there are provided means to separate the illumination from detected light.

There is also provided a computer program product for obtaining information of the spatial structure of an object having a subwavelegth size in at least one spatial direction in particular for carrying out a method according to the invention or a preferred embodiment thereof when loaded on a computer and carried out thereof, the computer program product comprising an instruction set for performing the following steps when suitably loaded on a computer:
- obtaining the detected data of an optical response of the object;
- obtaining the optical response of objects with known spatial structure;
- comparing the detected data with the simulated data and quantitatively determining the spatial structure of the object.

These and other objects, features and advantages of the present invention will become more apparent upon reading of the following detailed description of preferred embodiments and accompanying drawings. It should be understood that even though embodiments are separately described, single features may be combined to additional embodiments.

BRIEF DESCRIPTION OF THE TABLES AND THE FIGURES

Table 1 shows virtual determination of object sizes using different virtual microscopy approaches of Example 10.

Table 2 shows virtual determination of object sizes using different virtual microscopy approaches of Example 14.

Table 3 shows the results of experimental data analysis of Example 21.

DETAILED DESCRIPTION OF THE PREFERRED EMBODIMENTS

In the following preferred embodiments of the invention will be described in detail in with reference to the appended tables and figures.

First some of the terms used will be shortly explained:

The observation volume of a microscopic system as a measure for the overall three-dimensional (3D) optical resolution is given by the volume of an ellipsoid with axes $FWHM_{x,y,z}$ (FWHM in x, y, and z-direction, respectively).

Size Resolution is the smallest diameter of an isolated preferably fluorescent object (distance to neighbouring objects larger than the FWHM) which can be detected if the object is labelled with a minimum of one optical marker, respectively spectral signature only.

Figure 4:
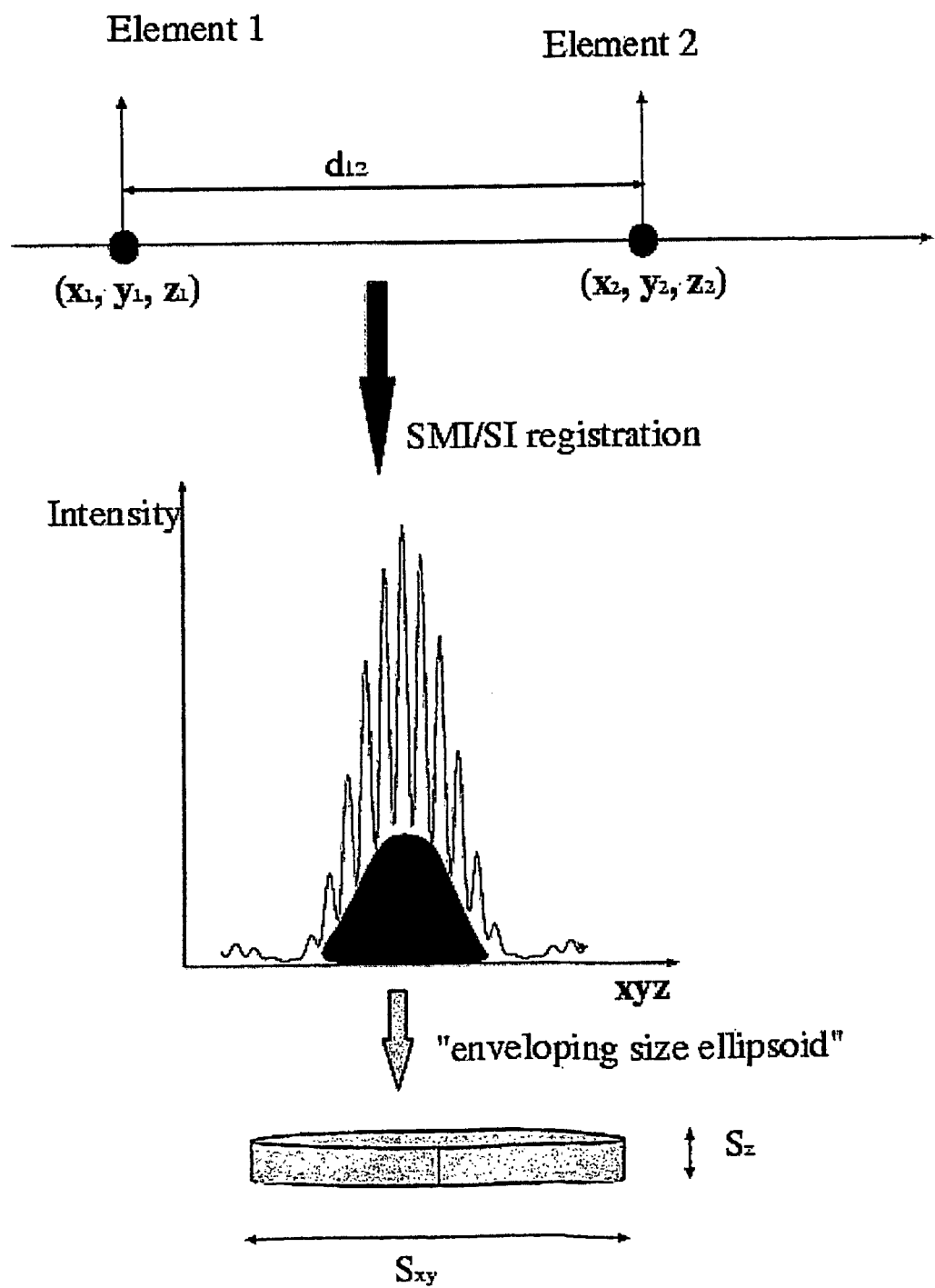
FIG. 4 illustrates schematically the determination of the distance between to point like elements labelled with the same spectral signature.

Reference is made to FIG. 4, which illustrates the determination of positions $(x_1, y_1, z_1)$ and $(x_2, y_2, z_2)$ of the two point like elements (for example between elements 1 and 2) labelled with the same spectral signature and their distance $d_{12} = \sqrt{(x_1-x_2)^2 + (y_1-y_2)^2 + (z_{1za-z2})^2}$ by calculating to which distance $d_{12}$ is fitting. First a SMI/SI registration of the axial intensity distributing in for example x, y and/or z direction is performed, followed by determining the size of the enveloping ellipsoind, i.e. the size in z direction $S_z$ and in x, y direction $S_{xy}$.

Spectral Signature is any photophysical feature of an object by which it can be identified by appropriate detector systems, such as absorption/emission wave lengths, fluorescence life time, polarisation etc.

Spatially Modulated Illumination (SMI) microscopy is a far field light microscopy method where a "standing light wave field" is produced in the object plane by crossing two collimated laser beams emerging from the front lenses of two opposing high numerical aperture objective lenses.

Spectral Precision Distance Microscopy (SPDM): At a given optical resolution, mutual positions and distances between "point like" or small objects can be determined with an error considerably smaller than the optical resolution if a) all objects to be measured and located within the same observation volume carry different spectral signatures; b) the diffraction images obtained from the different spectral signatures are registered independently from each other; c) the maximum of the diffraction image intensity distribution, or its fluorescence intensity barycenter, or another parameter describing the geometrical position of the diffraction image of the object, is determined by quantitative image analysis; d) where necessary, the positions obtained in c) are corrected for chromatic and other aberrations. Using special microscopical conditions and evaluation procedures ["Light MicroscOpical Nanosizing], up to a few objects may carry the same spectral signature.

Here the topology of an object especially a MMC or BMM composed of several parts ("elements"), is the relative position of these fluorescent labelled elements with regard to each other, or to another coordinate system and the mutual distances between the elements. The geometrical position of the fluorescent labelled elements may be defined e.g. by their fluorescence intensity gravity centre ("barycenter") of their light microscopical diffraction image, as by the maximum of this image.

Topological Resolution is the smallest distance detectable between two point like objects of different spectral signature. The topological resolution determines also the precision of colocalization of two objects of appropriate spectral signature. Since the definition of Topological Resolution is very close to the common definition of Optical Resolution, it may also be called "Resolution Equivalent".

In the following, under the term fluorescence it is to be understood any photon-interaction wherein there are differences between the illumination, respectively excitation spectrum, and the emission spectrum of the same object which cannot be explained based on the monochromatical absorption only. That includes for example in particular Multiphoton interactions, by which the excitation wavelengths can be greater than the emission wavelengths. Thus the term fluorescence will be also used for the closely related phenomena as Luminescence and Photophosphorescence. This includes in particular the cases of longer fluorescence duration, for example in the millisecond range.

The invention (called also "Light MicroscOpical Nanosizing" or LIMON) is based on the physical use of preferably Spatially modulated illumination as disclosed in DE 198 30 596 A1; B. Bailey, D. Farkas, D. Taylor & F. Lanni, Enhancement of axial resolution in fluorescence microscopy by standing-wave excitation, Nature 366, 44-48 (1993); B. Schneider, I. Upmann, I. Kirsten, J. Bradl, M. Hausmann, C. Cremer: A Dual-Laser, Spatially Modulated Illumination Fluorescence Microscope, Microsc. & Anal. 57(1), 5-7 (1999);B. Albrecht, A. V. Failla et al, Spatially Modulated Illumination Microscopy: Online Visualization of Intensity Distribution and Predictions of Nanometer Precision of Axial Distance Measurements by Computer Simulations, Journal of Biomedical Optics, in press. (2001) included herein by reference or any other kind of suitable structured illumination as disclosed by J. T. Frohn, H. F. Knapp, A. Stemmer: True optical resolution beyond the Rayleigh limit achieved by standing wave illumination, Proc. Natl. Acad. Sci. USA 97, 7232-7236 (2000); J. T. Frohn, H. F. Knapp, A. Stemmer, Optics letters 26:828-830(2001) included herein by reference or 4Pi-illumination with a destructive interference around the focal intensity maximum, resulting in two or more side peaks of high intensity relative to the main peak.

According to one embodiment of the invention, a relevant property of a Spatially modulated illumination light microscope or SI microscope is that the excitation light forms an interference "fringe pattern" in the object space. Thus, all methods of structured illumination are suitable for the present invention which allow a "standing wave field" illumination or otherwise structured illumination in the object space, providing either intensity modulated illumination in the direction of the optical axis (z), or in any direction parallel to the object plane (x,y), or both, or in a given angle to object plane and optical axis, respectively. Preferably, a spatially modulated or structured illumination is used which produces in at least one spatial direction in the object space an extended or localised modulated light intensity pattern, i.e. a "fringe pattern", with at least three of such fringes having an intensity maximum above background noise level, the fringes having a Full-Width-at-Half-Maximum (Full-Width-at-Half-Maximum$_f$) considerably lower than the Full-Width-at-Half-Maximum of the epifluorescence PSF $FWHM_{EPI}$ of a microscope system with lens objectives of same or different Numerical Aperture, excitation and detection wavelengths. At least two fringes adjacent to the fringe with the maximum intensity are assumed to have peak intensities of at least 30% of the maximum. Methods to realize this have been described in the above cited writings and are regarded to be relevant for the technical basis of the invention, but as such do not form a part of it. Experimentally, the fringe pattern may be determined by using an appropriate "point like" object excited to fluorescence by the excitation field, i.e. an object with a diameter considerably smaller than the $FWHM_f$ allowing a maximum of modulation contrast of the fluorescence image detected.

Preferably, the structured illumination is a Spatially modulated illumination along the optical (z) axis and further preferably, a specific case of an axial Spatially modulated illumination excitation field. Similar procedures for the other types of modulated illumination are obvious for any specialist trained in the art.

To achieve spatially modulated illumination in the z-direction, a collimated and vertically polarised beam of coherent light may be focused into the back plane of two opposite objective lenses after it is split in a Mike Zender interferometer. This configurations generates, between the two objective lenses, a standing wave-field configuration characterised by $sin^2$ fringe intensity patters along the optical axis (z). The advantage of this system is that the emission light intensity distribution is modulated by oscillation fringes. Since this modulation is highly sensitive to the axial extension of the object excited to fluorescence, this will make it possible to obtain, with the help of specially designed information technology tools making part of the invention, quantitative information's about the size of the object along z even if this size is considerably smaller than the excitation wavelength. The fact as such has been noted previously [B. Bailey, D. Farkas, D. Taylor & F. Lanni, Enhancement of axial resolution in fluorescence microscopy by standing-wave excitation, Nature 366, 44-48 (1993)] in a qualitative statement. However, so far no attempt has been described to use this fact for the quantitative analysis of subwavelength sized fluorescent objects. Preferably, the invention can be applied to all MacroMolecular Complexes, in particular BioMolecular Machines or BioMolecular Modules, a) which are appropriately fluorescence labelled to allow the registration of a sufficient number of fluorescence photons, if necessary in a spectrally discriminated way, and b) which have a minimum distance of a neighbouring object or element fluorescence labelled in the same way, this distance corresponding at least to the optical lateral (x,y) resolution, or at least to the axial (z) optical resolution. For example, using a system with objective lenses with a numerical aperture of 1.4 and light in the wavelength range of 360-800 nm, this means that two MacroMolecular Complexes labelled with the same spectral signatures have to have either a lateral (x,y) distance of at least 200 nm from each other, or an axial (z) distance of at least 600 nm from each other. Where this latter condition cannot be fulfilled, methods of narrowing the Point Spread Function according to the above described state of the art have to be applied. However, the minimum distance requirements mentioned in many cases do not severely impede the range of applications of the invention, since the specimens containing the MacroMolecular Complexes and in particular the BioMolecular Machines or BioMolecular Modules to be analysed can often be prepared in a way fulfilling these requirements. For example, if in a mammalian cell nucleus of a diameter of 10 μm only a few nuclear sites with a size smaller than the observed volume $V_{OBS}$ and located on different chromosome territories, are labelled with the same spectral signature then this condition is easily fulfilled. In cases, where only two objects of the same spectral signature are located within the observation volume $V_{OBS}=(4/3)\pi(FWHM_x FWHM_y FWHM_z)/(8)$. In special cases, techniques can be applied which allow by special labelling and selection schemes to measure even the distance between MacroMolecular Complexes of the same type, or the topology of "equal" elements within such MacroMolecular Complexes, being located in the same observation volume.

Basic Concept of Spatially Modulated Illumination-Virtual Microscopy (SMI-VIM).

Virtual Microscopy (VIM) is based on computer simulations of the structure to be studied, using a set of assumptions including labelling schemes. The computer data sets are convoluted with the PSF of the microscope system used for the registration of corresponding experimental data, adding appropriate noise conditions as well as other condition describing the imaging process. The virtual microscopy data obtained may be analysed in the same way (e.g. especially using digital image analysis tools) as the experimental data. The results of the virtual microscopy data can then be directly compared with the experimental results. Deviations between model predictions and experimental results can be used to refine the model.

Figure 7:
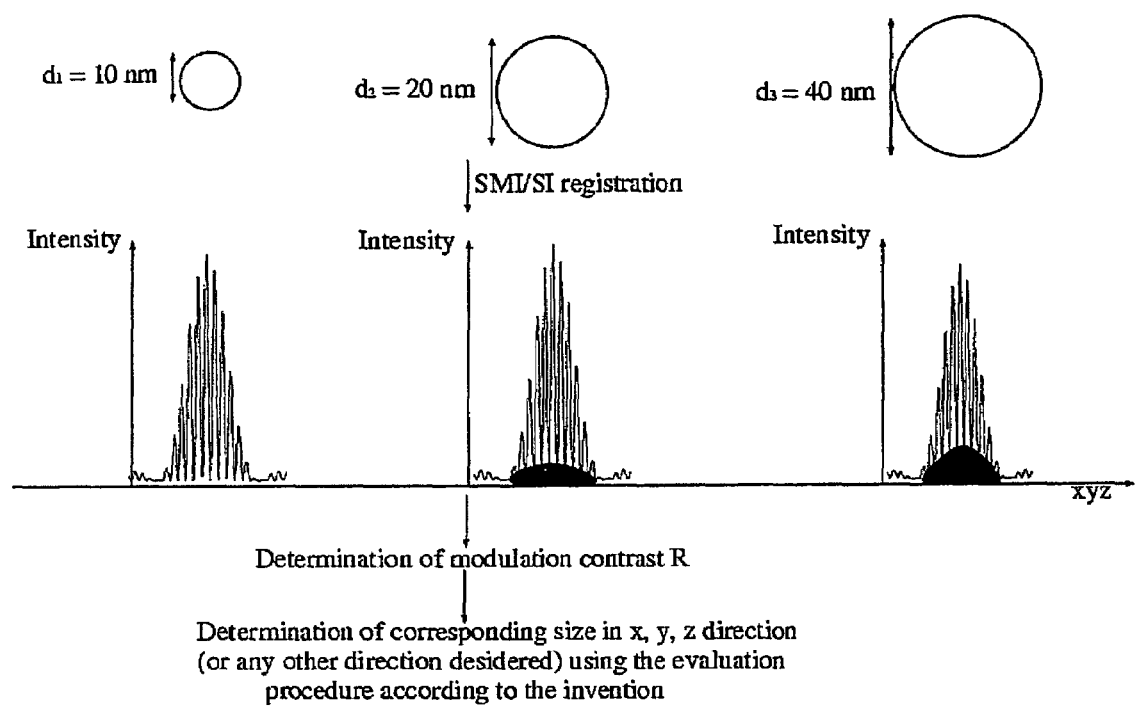
FIG. 7 shows a schematic example of determination of the size.

Under the above mentioned minimum distance requirements, the basic concept to determine the diameter ("size") of small fluorescent objects considerably below the optical resolution of advanced microscope systems (about 500-600 nm in axial direction under conditions relevant in routine applications) is to calibrate the disturbance of the modulation of the Spatially modulated illumination/Structured Illumination (SMI/SI) fluorescence intensity diffraction image as shown on FIG. 7, which illustrates the determination of the corresponding size on x, y, z direction or any other direction desired. On FIG. 7, the x, y and z are the spatial coordinates. In the actual measurements the intensity is measured at least along one spatial coordinate. Referring to FIG. 7, first a step of measurement of the optical response, i.e. SMI/SI registration of the intensity distribution in for example direction x, y, and/or z, of objects with different sizes is performed. Here, the optical response of objects with size $d_1=10$ nm, $d_2=20$ nm and $d_3=40$ nm is shown. Subsequently a step of determination of the modulation contrast and a step of determination of corresponding size in x, y, z direction (or any other direction desired) using evaluation procedure according to any of the embodiments of the invention are performed.

To determine the size, an extended fluorescent MMC, e.g. a BMM, or any other "extended fluorescent object" is represented as the superposition of several "point like" preferably fluorescent objects, each one emitting light independently with respect to the other. Still further preferably the invention described below may also be used to discriminate a "point like" object from an "extended object".

Figure 8A:
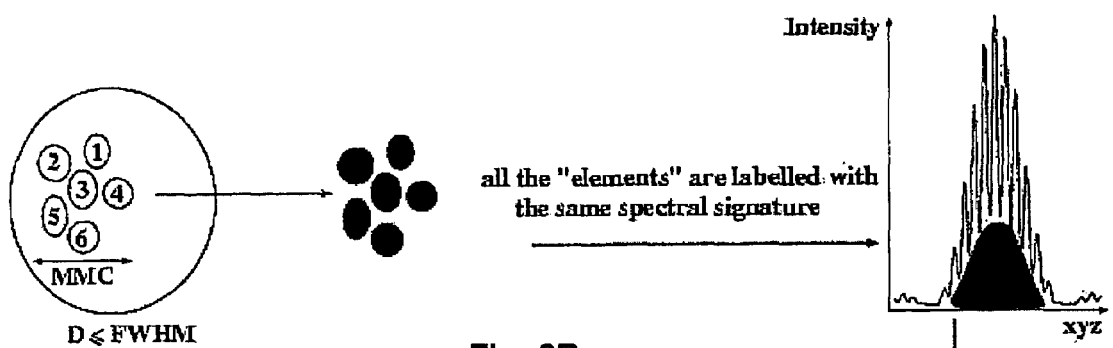
FIG. 8A shows a schematic example of determination of the overall size a MacroMolecular Complexes (MMC) in the case all the elements within the object are labelled with the same spectral signature.
Figure 8B:
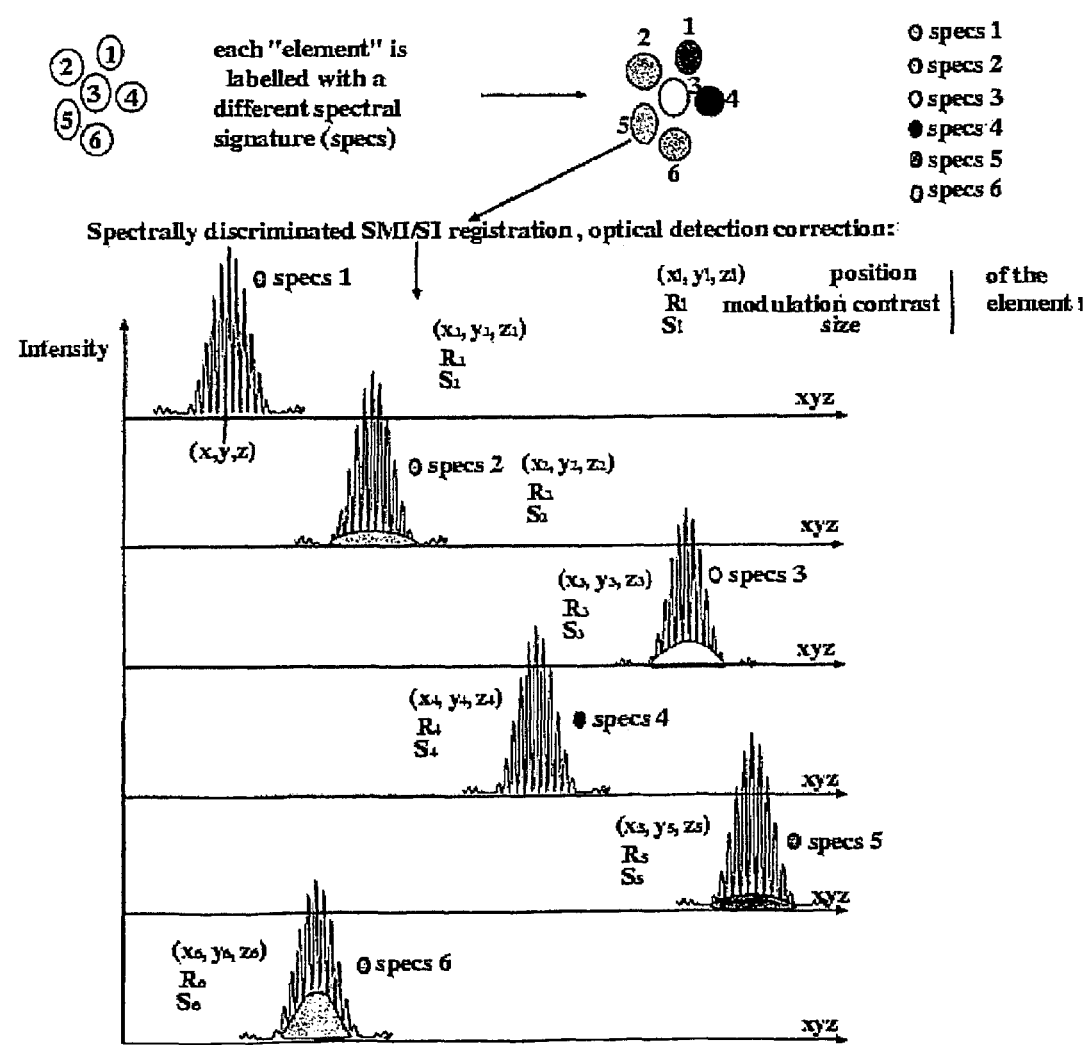
FIG. 8B shows a schematic example of determination of the topology of a MacroMolecular Complexes (MMC) in case each elements is labelled with a different spectral signature (specs).

The resulting fluorescence intensity distribution in the image plane of one or more objective lenses used to realise the modulated illumination, is the incoherent sum of the contributions of each point like object, each contribution corresponding to a Spatially modulated illumination-Point Spread Function (SMI-PSF) located at the respective position. FIGS. 8A and 8B show in more detail the principle of determination of size and topology of an object, e.g. a MMC, wherein $(x_i, y_i, Z_i)$, $R_i$, $S_i$ are respectively the position, the modulation contrast and size of the i-th element. In FIG. 8A all the elements 1, . . . 6 are labelled with the same spectral signature. Then the step of registration of the intensity distribution in any desired direction (for example x, y, z direction) is performed followed by a step of evaluation of the size of the MMC in the desired direction (for example x, y, z). In FIG. 8B each of the elements 1, . . . , 6 is labelled with a different spectral signature (specs). Thus i-th element, i=1, . . . , 6, having coordinates $(x_i, y_i, z_i)$ element, is labelled respectively with specs i (i.e. with a i-th optical marker). Then the step of spectrally discriminated SMI/SI and optical correction detection is performed, wherein the intensity distribution in a desired direction (for example in x, y, or z direction) of the light from each of the object is independently recorded.

Figure 9:
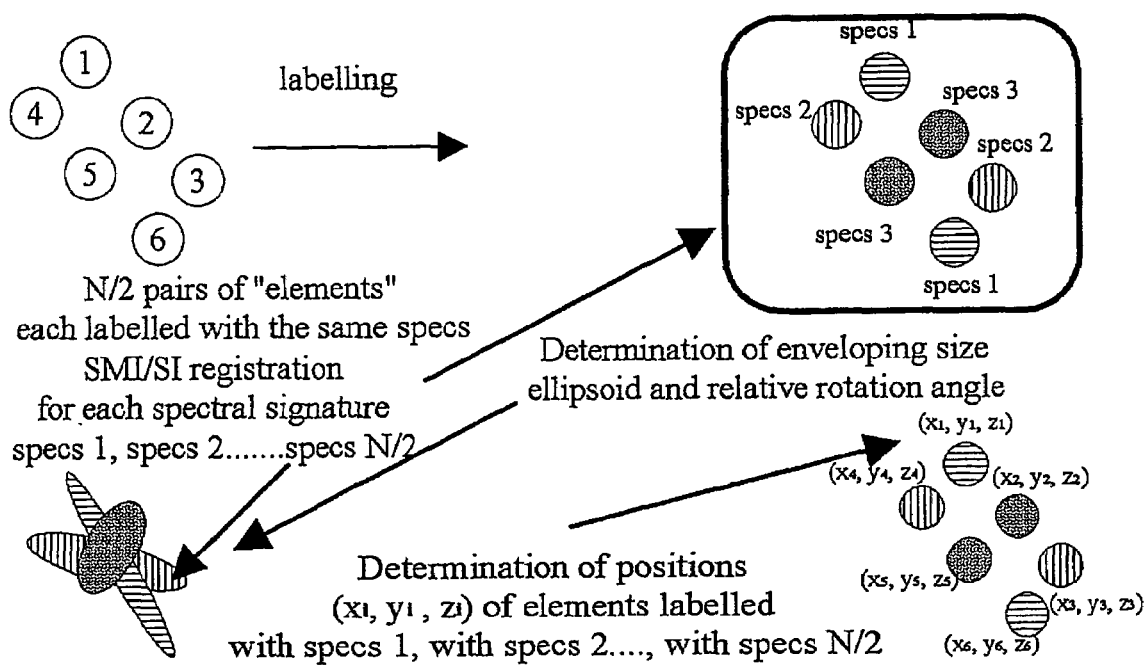
FIG. 9 illustrates schematically the determination of the topology of N elements within a subwavelength sized observation volume using N/2 spectral signatures.

FIG. 9 shows a schematic example, wherein the elements 1, 2, . . . 6 are labelled in pairs, for example elements 1 and 6 with specs 1, elements 2 and 5 with specs 3 and elements 3 and 4 with specs 2, thus there are N/2 pairs of elements each labelled with the same specs. A step of determination of enveloping size ellipsoid and relative rotation angle and/or a step determination of positions $(x_i, y_i, z_i)$ of element "i" labelled with specs 1, specs 2, . . . specs N/2. The following description is for the use of two opposed objective lenses for excitation (see [B. Albrecht, A. V. Failla, A. Schweitzer, C. Cremer: Spatially modulated illumination microscopy: A new approach to biological nanostructure analysis. GIT-Microscopy, July 2001; B. Schneider, I. Upmann, I. Kirsten, J. Bradl, M. Hausmann, C. Cremer: A Dual-Laser, Spatially Modulated Illumination Fluorescence Microscope, Microsc. & Anal. 57(1), 5-7(1999);]) and for one objective lens for fluorescence light collection. For the Spatially modulated illumination (SMI) pattern assumed, the extension to other directions is obvious for anyone trained in the art.

The Spatially modulated illumination-Point Spread Function (SMI-PSF) is defined as the appropriately normalised axial (z) intensity distribution in the image plane obtained using a "point-like" fluorescent object. In the present description, the "point like" object may be represented by an object of e.g. 10 nm diameter, whereas an MMC represents a specimen whose axial diameter size (S) starts to be comparable with the $FWHM_f$ of the individual fringes of the SMI-PSF. The application to other sizes of "point like" objects is obvious for anyone trained in the art. Thus, for the purpose of size determination, a MMC can be replaced by several fluorescent point-like objects (an ensemble), each e.g. having a size $s_0$ equal to 10 nm. Following this scheme, it is possible to represent the Axial Fluorescence Intensity Distribution (AID) in the image plane of this ensemble as the incoherent superposition of axial Point Spread Functions. For more details see Example 2 and FIG. 12.

Preferably, any size which is considerably smaller than the FWHM of the individual or secondary fringes ($FWHM_f$) according to the invention. Further preferably, for the sake of a clear description, here the size of the constituent point like objects are fixed to 10 nm. The number of "point-like" objects and their distances from each other represent the size of the MMC formed by these constituent "point like" objects (see Example 2). For example, the maximum distance measured between two elements of a MMC corresponds to the diameter of the minimum spherical enveloping volume, i.e. the colocalization volume (see FIG. 3).

Figure 1A:
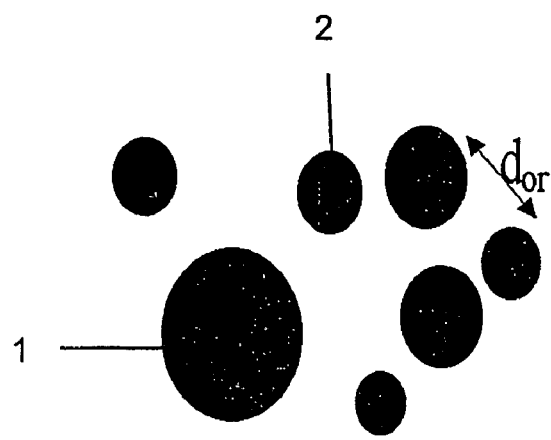
FIG. 1A shows a schematic example of an optical resolution $d_{or}$.
Figure 1B:
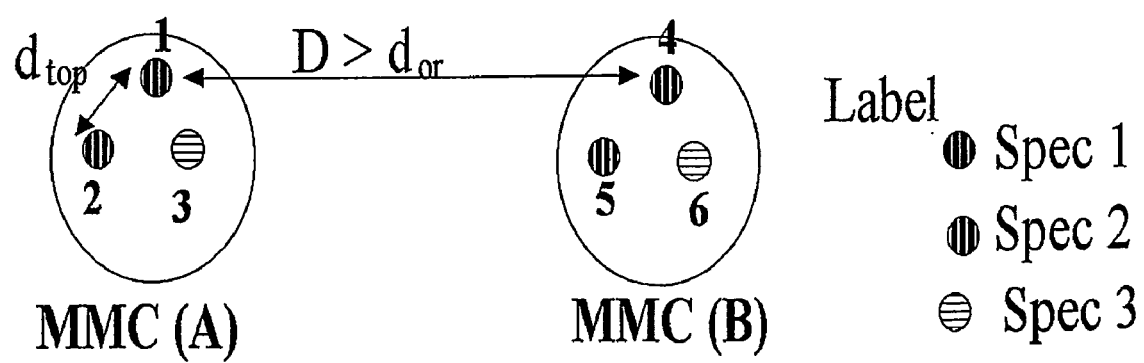
FIG. 1B shows a schematic example of a topological resolution $d_{top}$.
Figure 2:
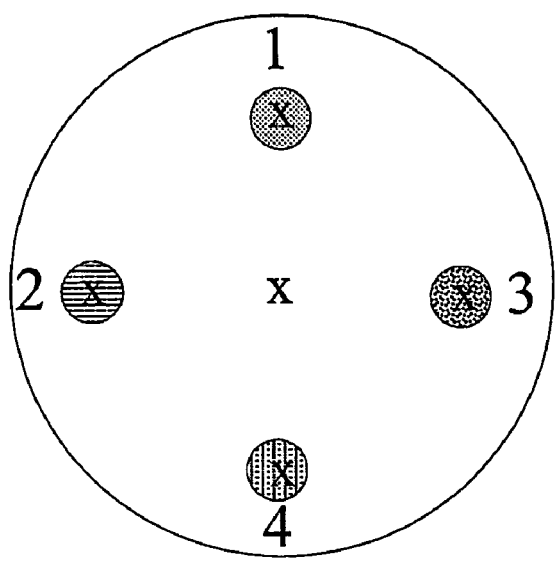
FIG. 2 illustrates schematically the problem of Spectral Precision Distance Microscopy using a Point Spread Function having one peak with width FWHM.
Figure 2:
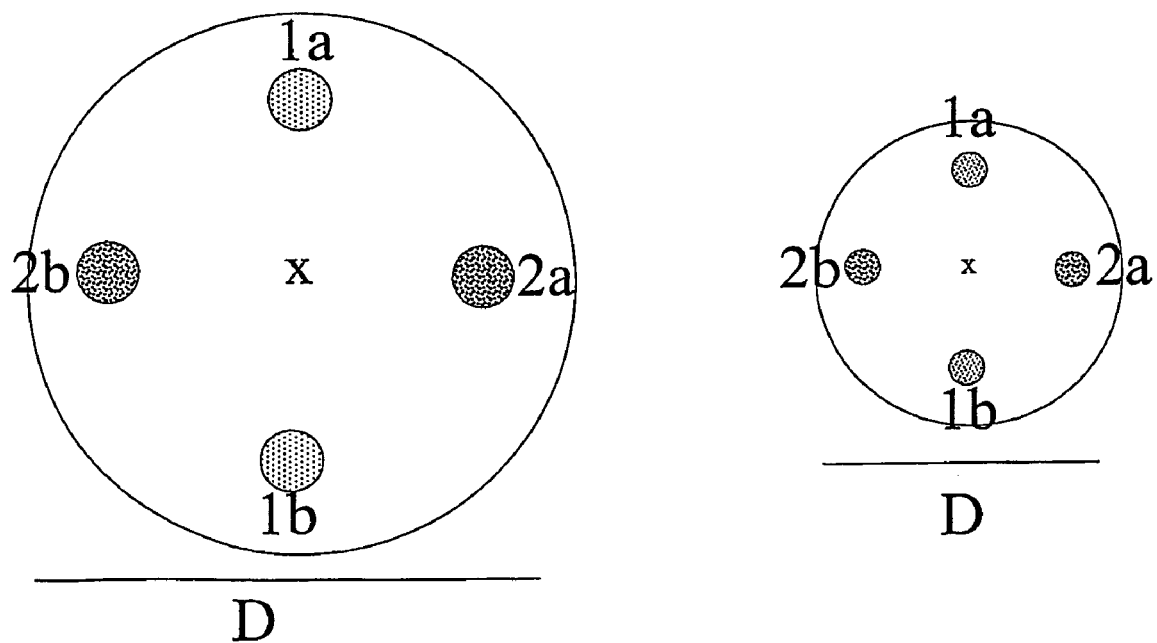
Figure 3:
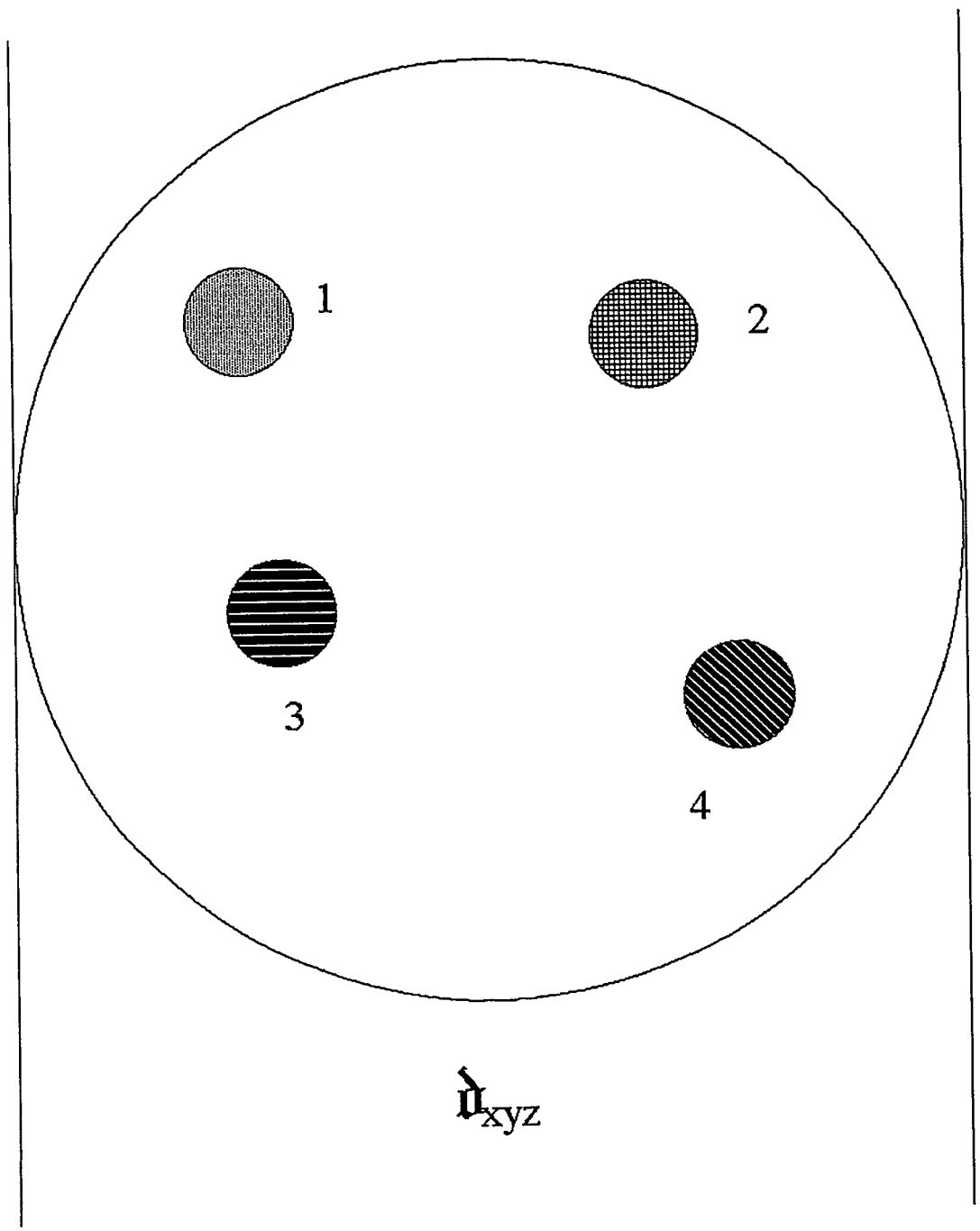
FIG. 3 shows a schematic example of a topological resolution and colocalization volume

With respect to FIG. 3, a colocalization error $\delta = \delta_y = \delta_z = \delta_{xyz}$ means that the mutual distance between all the fluorescent labelled objects 1, 2, 3, . . . N [for example labelled respectively with specs 1, specs 2, specs 3, etc] are equal or smaller than $\delta_{xyz}$. Frequently they may be enclosed by an enveloping volume of a diameter $\delta_{xyz}$. (in case of different $\delta_x$, $\delta_y$, $\delta_z$ the colocalization volume is given by an appropriate ellipsoid volume). The smallest detectable distance between two objects (for conditions see FIG. 1) is $d_{top}$. Thus the minimum detectable colocalization error is equal to $d_{top}$.

Increasing the number of "point like" objects with a given distance, the size of the MMC formed increases and the modulation of the axial intensity distribution decreases. The size range that can be evaluated for each excitation wavelength ($\lambda_{ex}$) is limited. In fact, it is not possible to recognize any differences in the axial intensity distribution for sizes smaller than about 20 nm and larger than about 190 nm, using a $\lambda_{ex}$=488 nm for the Spatially modulated illumination pattern assumed (see the following section). In the case where the MMC size approximately corresponds to two times the $FWHM_f$ of the individual fringes, the axial intensity distribution does not present any useful modulation.

Figure 11:
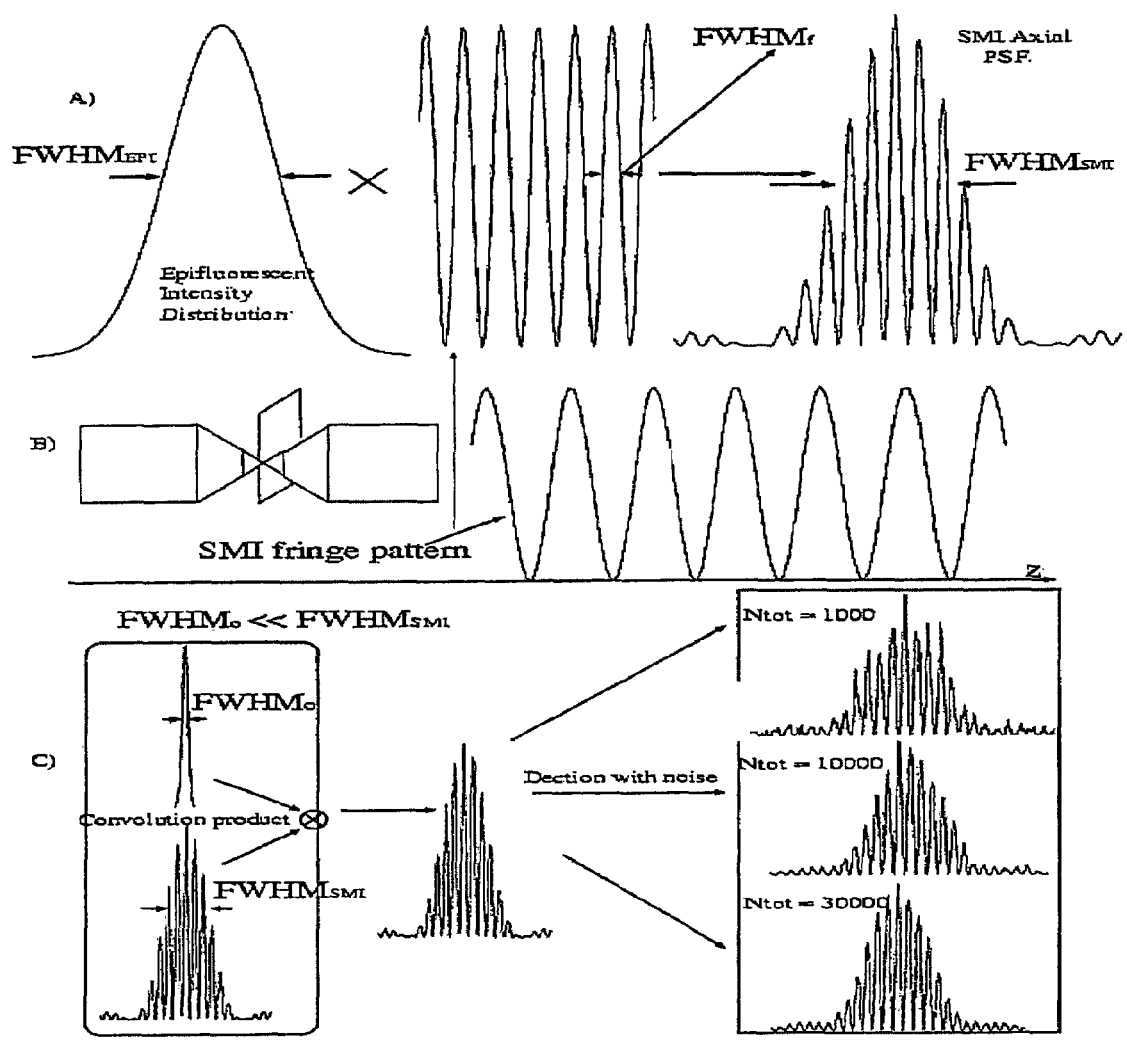
FIG. 11A illustrates the principle of Spatially modulated illumination/SI Virtual Microscopy (VIM) and VIM visualisation of the effects of the photon noise of the Axial Intensity Distribution (AID) in case of point like object of Example 1.
FIG. 11B shows illustrating the dependency of the Axial Intensity Distribution on The Total Number ($N_{tot}$) of detected photons of Example 1.
Figure 11:
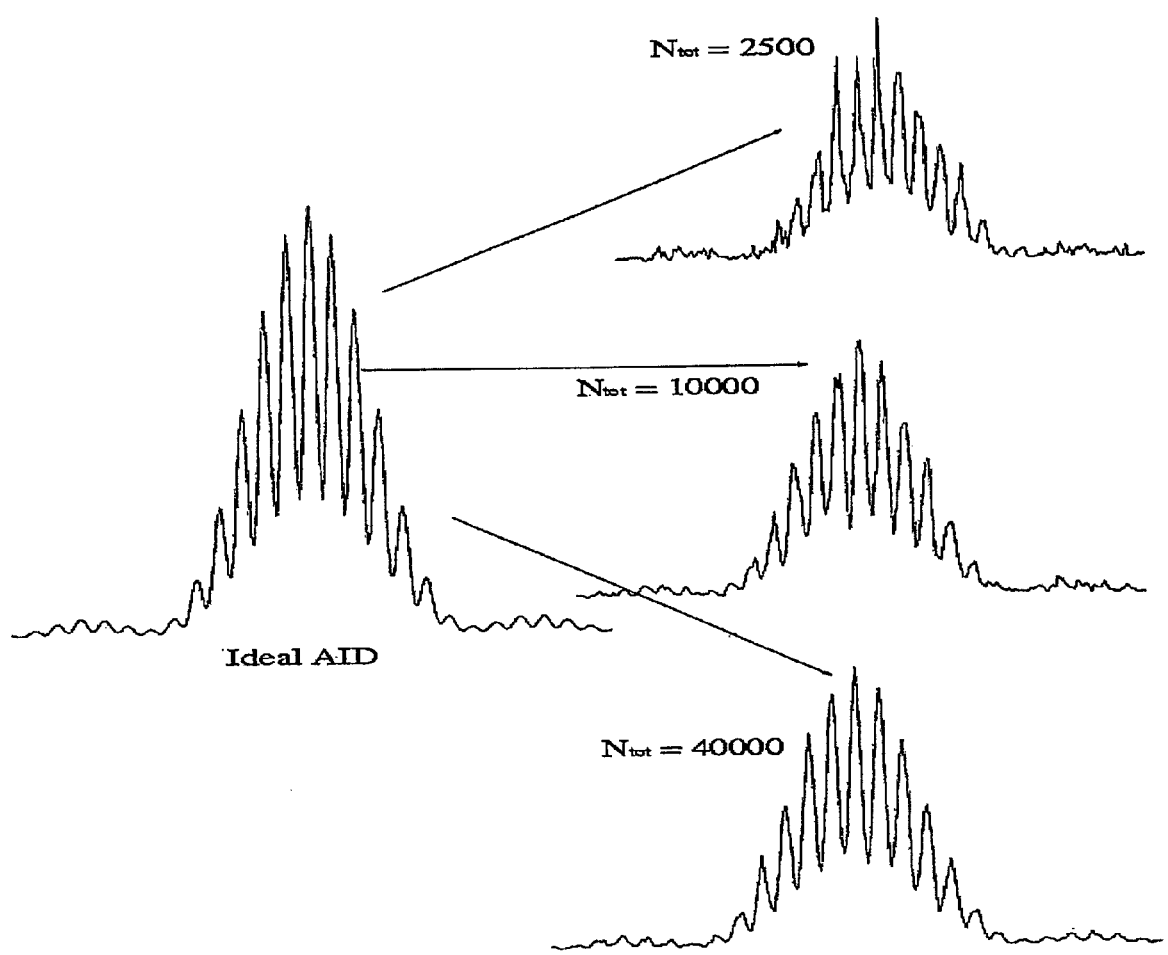

The size range discussed above depends on the fringe Full-Width-at-half-Maximum Point Spread Function ($FWHM_f$ PSF) of the fluorescence collecting objective lens being directly related to the numerical aperture of the objective lens, and to the excitation wavelength $\lambda_{ex}$. A still another preferred embodiment of the invention, uses invention related information technology tools to determine the object diameter size along the optical axis (z) in a quantitative way, and how it depends on the fluorescence photon count conditions. To describe the basic content of the invention, the conditions shown in Example 1, 2, respectively FIGS. 11, 12 are assumed. To obtain the AID of the object, the individual axial intensity distributions of the constituting point like objects were summed up. Note that for a better schematic representation, the axial intensity distributions of the constituting point like objects in Example 1 are not represented in scale. The resulting AIDs are shown on the right in FIG. 11, respectively FIG. 12.

Figure 12A:
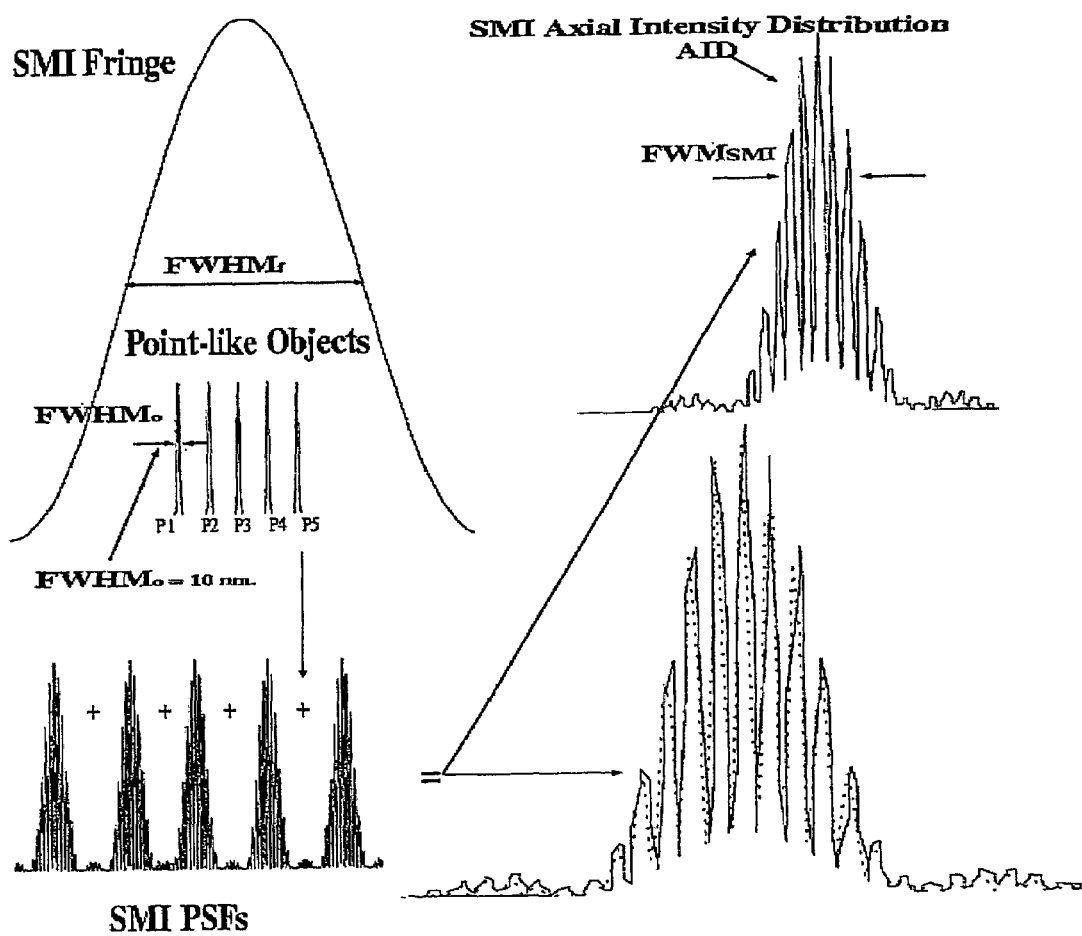
FIG. 12A illustrates the Spatially modulated illumination-VIM extended object axial intensity distribution computation of Example 2.
Figure 12B:
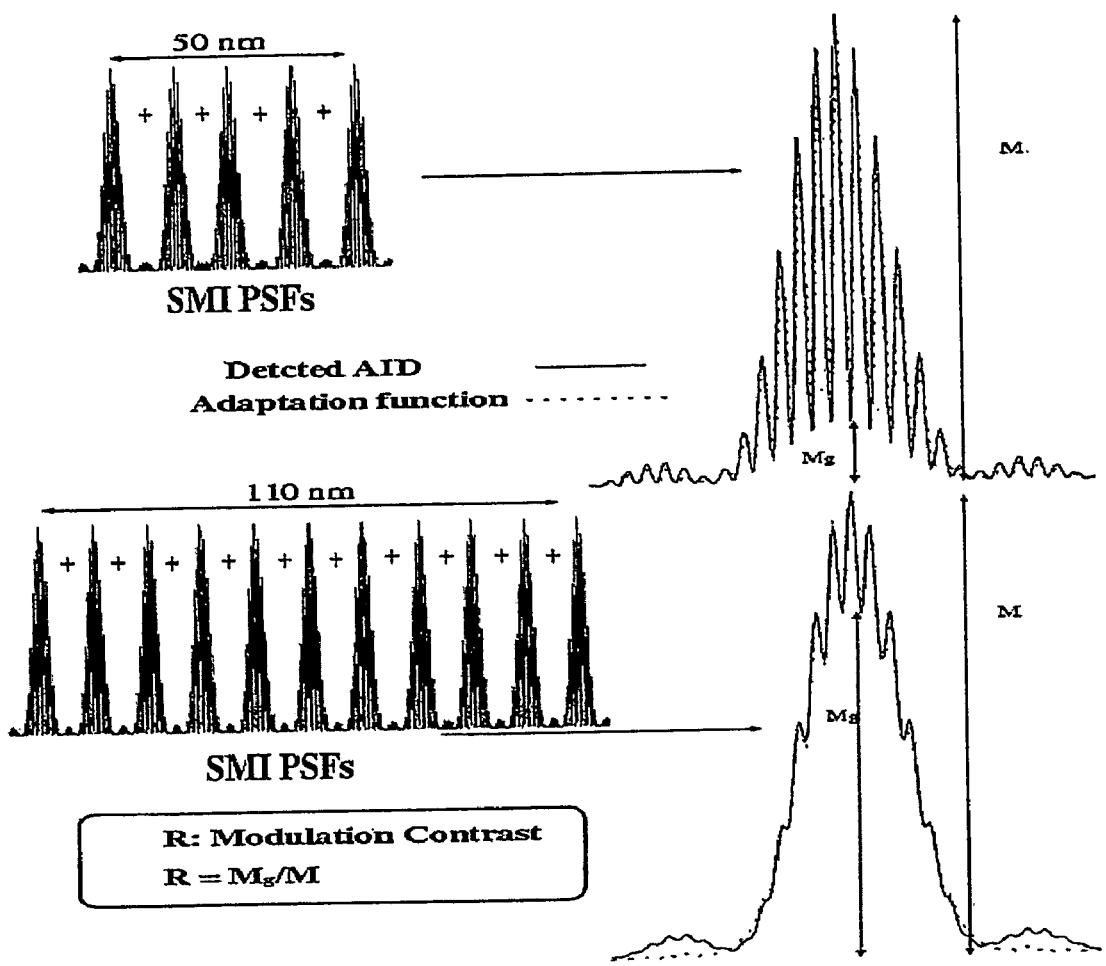
FIG. 12B illustrates the relation between the modulation contrast R and the size of an extended object of Example 2.
Figure 13:
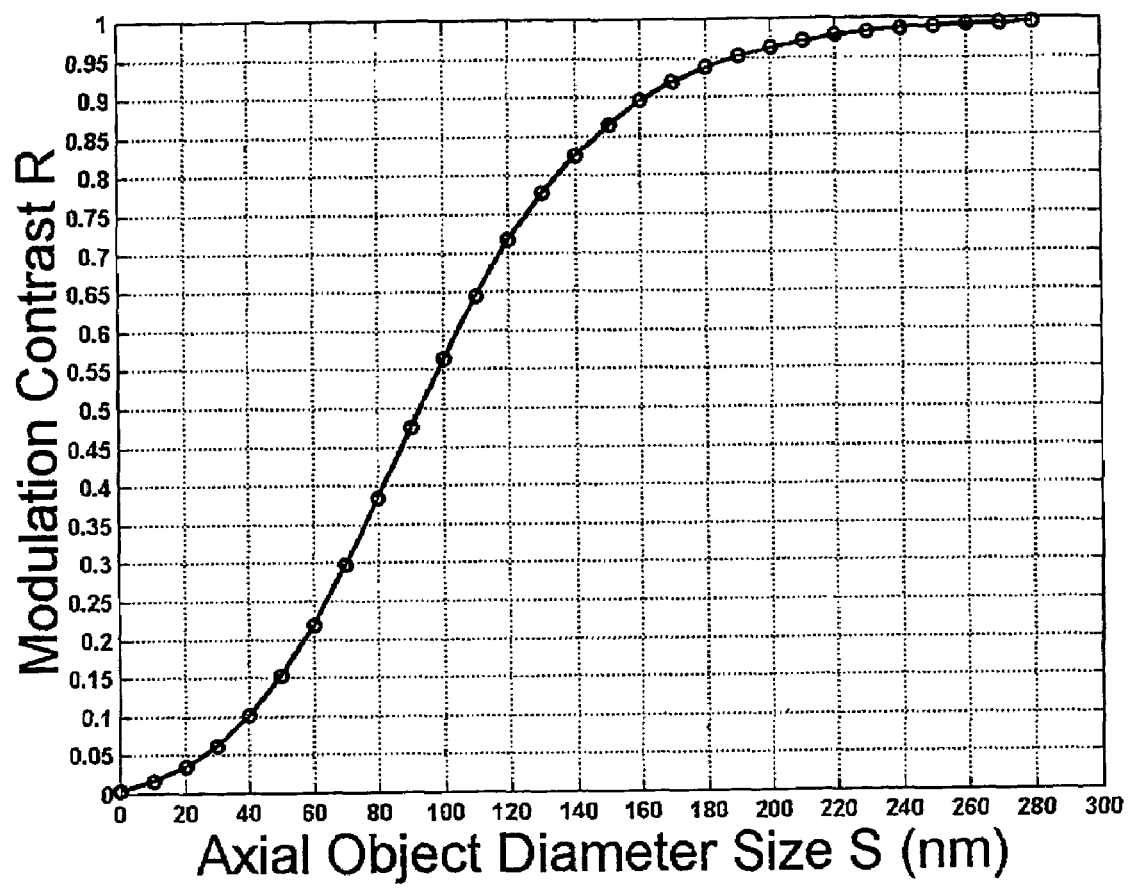
FIG. 13 shows a graph of the relation between the modulation contrast and the side of the object of the Example 3.

It is obvious that the modulation contrast R strongly depends on the object size (see Example 2, 3 and respectively FIGS. 7, 12, 13). In particular, a preferred embodiment of the invention relates to a method to determine R as a function of the size of the MMC, or any other subwavelength sized fluorescence labelled object, and $\lambda_{ex}$ using information technology approaches, under given boundary conditions of excitation wavelength, emission wavelength, $FWHM_f$, $FWHM_{EPI}$, $FWHM_{SMI}$, further preferably the FWHM of the Point Spread Function of the system, numerical aperture of the objective lenses, total number of fluorescence photons registered for a given spectral signature, adaptation function used, noise other then photon noise etc. For an example of the influence of the total number of detected photons see Virtual Microscopy Example 1.

For the modulation contrast determinations as a function of object size, three dimensional (3D) digital axial intensity distributions (AIDs) produced by Spatially modulated illumination-virtual microscopy can be used.

In a first virtual microscopy computational experiment, the voxel size of each image was 100 nm×100 nm×20 nm. Here, the projection on the z axis of the 3D axial intensity distribution was calculated. The axial diffraction image intensity distributions (AID) of extended objects symmetrically positioned with respect to the axial Spatially modulated illumination fringes were analysed. Furthermore, here it was assumed that 3D distances (D) between an extended object and its nearest neighbour of the same spectral signature was D>>$FWHM_{SMI}$, where $FWHM_{SMI}$ denotes the Full-Width-at-Half-Maximum of the envelope of the Spatially modulated illumination-Point Spread Function (SMI-PSF), corresponding to the FWHM of the detection PSF. This $FWHM_{SMI}$ can be approximated by connecting the maxima of the individual fringes in the SMI-PSF.

To obtain the desired relationship between object size and modulation contrast, it was analysed by Spatially modulated illumination-virtual microscopy (SMI-VIM) how the axial intensity distribution (AID) changed on variation of the object size. Here, this object size was defined as the maximum distance between the axial positions of two or more constituting "point like" objects representing the axial extension S of the extended object to be analysed, in particular a MMC or more specifically, a BMM. It was found that the modulation contrast of the AID decreased with increasing size S. The basis of a quantitative determination of the size consisted on the study of the relation between the maximum of the $sinc^2$ envelope and the size of the specimen. In particular, the size dependent variation of this relation was analysed, changing S, The modulation factor R between the total intensity maxima M and the maxima of the $sinc^2$ envelope was determined by SMI-VIM (see above), taking into account optical aperture, exciting wavelength, refraction index as well as fluorescent photon count statistics. A first example for the calculation of a calibration curve by Spatially modulated illumination-VIM according to preferred embodiment of the invention is shown in Virtual Microscopy Example 3, assuming "ideal" optical conditions (see Example 1, 2 assuming the absence of noise).

In a first application, the modulation contrast R was studied for the excitation wavelengths $\lambda_{ex}$=360 nm, 488 nm, 564 nm and 647 nm. For each excitation condition, the factor R was computed as a function of the size S of the extended object representing, e.g. a BMM. In this case, the AID was calculated as the axial projection of the 3D convolution product between a Gaussian-like "point like" object (Full-Width-at-Half-Maximum of intensity=$FWHM_0$, and the Spatially modulated illumination-PSF. In this description, extended objects asymmetrically positioned in the fringe patterns of the modulation illumination where not further considered. For an execution example according to the invention see Spatially modulated illumination-VIM Example 3 and FIG. 13. A test function G(z) was used, extracting information's from the axial intensity profile, in order to evaluate S. The test function, based on a least square algorithm, is described in the attachment (Example 1, 2).

In Example 3, R is given as a function of the extended object size S, corresponding to the axial diameter. As an example, R is shown for $\lambda_{ex}$=488 nm. For simplicity, also the emission wavelength $\lambda_{em}$ of the excited fluorescence was set to $\lambda_{ex}$. In principle, such a condition can be experimentally obtained by e.g. using fluorescence life time microscopy [P. P. Kerten, P. Tinnefeld, M. Sauer: Identification of single fluorescently labelled mononucleotide molecules in solution by spectrally resolved time-correlated single-photon counting. Appl. Physics B 71: 765-771 (2000); P. Tinnefeld, V. Busalmann, D. P. Herten, K.-T. Kan, M. Sauer: Confocal Fluorescence Lifetime Imaging Microscopy (FLIM) at the single molecule level. Single Mod. 1:215-223(2000)].

Figure 14:
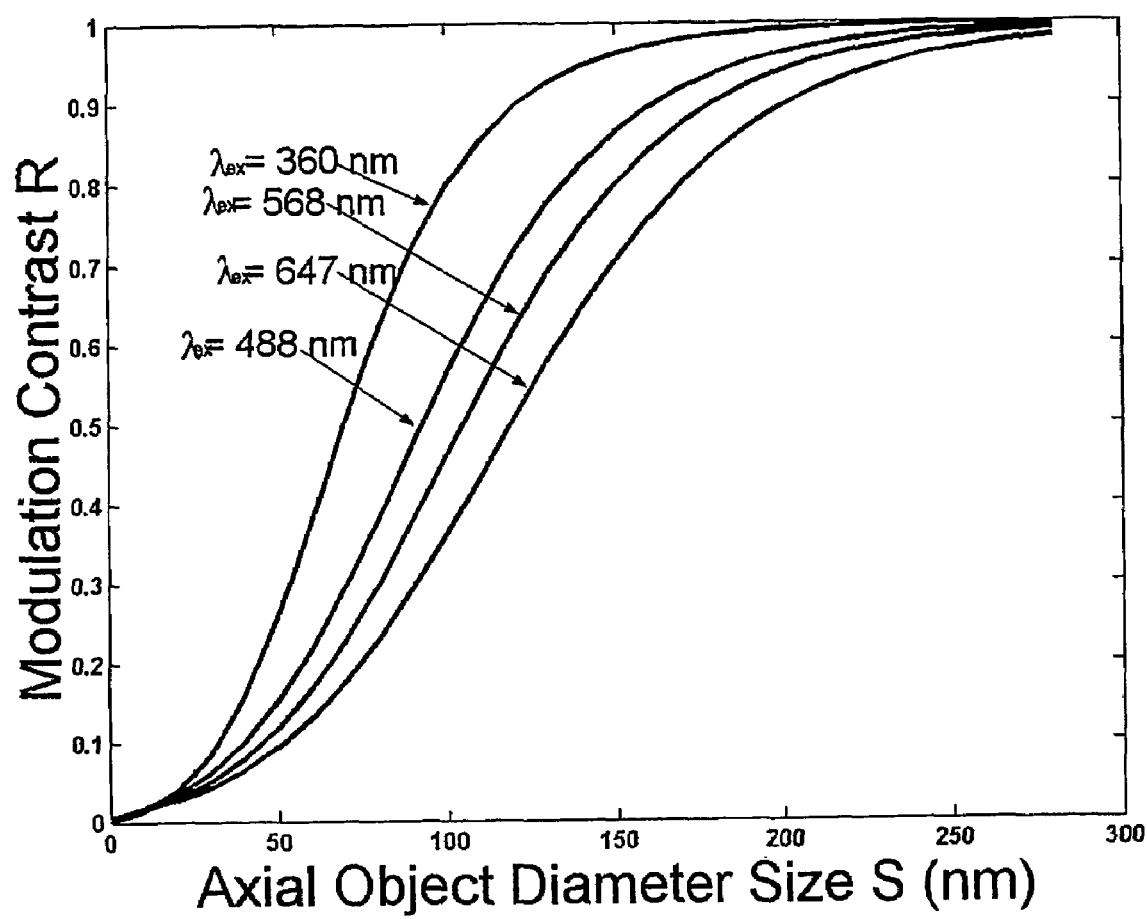
FIG. 14 shows a graph of the dependence of the modulation contrast R from the excitation wavelength of the Example 4.

In Example 4, respectively FIG. 14, the above mentioned relation R=R{S} is represented for four different wavelengths. In a certain size range, being different for different excitation wavelengths, assuming else constant conditions, R=R{S} increases strongly with the axial size of the object. For a special case see Example 3, 4. In case a spherical object is assumed, this corresponds to the diameter of the object in all directions.

In a limited range it is possible evaluating S to determine the axial object size graphically or within certain limits, with the help of a linear approximation function. This range, as it is expected, depends on the fringe Full-Width-at-Half-Maximum, $FWHM_f$, and varies by changing the excitation wavelength. For object diameters under 20 nm and above 180 nm, no significant changes of the parameter R were detected under the assumptions used in Example 3 ($\lambda_{ex}$=488 nm).

The fit parameters α, β (for definition see Example 5) were evaluated using all the above cited excitation wavelengths. The resulting means and their standard deviation values are given by the equation described in the Example 5.

In a second application, using the four calibration functions R=R{s} above described, the analytical function R=R{s, $\lambda^*_{ex}$} was calculated, where $\lambda^*_{ex}$ is a parameter called effective wavelength (see Example 6). The effective wavelength of an Spatially modulated illumination/Structured illumination (SMI/SI) microscope takes into account all the variations of the refraction index; furthermore, in the case of the SMI microscopical device it takes into account the tilting angle between the beams and the optical axis (z) and the camera acquisition axis. To facilitate size and topology measurements according to the invention, in the case of different excitation wavelength, the optical conditions, in particular the tilting angles of the exciting laser beams, may be chosen in such a way that the effective wavelength $\lambda^*_{ex}$ for modulation contrast R determination is equal for the different excitation wavelength.

After testing several functions, in order to fit three in the example given (the calibration functions concerning $\lambda_{ex}$=360 nm, $\lambda_{ex}$=568 nm and $\lambda_{ex}$=647 nm) of the four calibration functions, one closed analytical expression, (described in the examples), characterised by three parameters depending only on $\lambda^*_{ex}$, was chosen. For each parameter, several fitting functions were tested varying the effective excitation wavelengths. In the case shown here, the effective wavelength (see example 3) coincided with the excitation wavelengths. Then for each parameter the explicit dependence on $\lambda^*_{ex}$ was determined, and this relation was placed inside the expression R=R{s, $\lambda^*_{ex}$}. As a prove of the validity of the algorithm implemented, a comparison between the fourth calibration function measured by virtual microscopy ($\lambda_{ex}$=488 nm), and the one obtained plotting R=R{s, $\lambda^*_{ex}$=488 nm} was made. The two calibration functions, in different ways evaluated, were in good agreement as shown by the Example 6 and FIG. 16. In this way a fast and high precision algorithm to determine the relation between the object size S and the modulation contrast R was developed, allowing the user to determine such a relation for all the experimentally realised and detected effective wavelengths.

Figure 17:
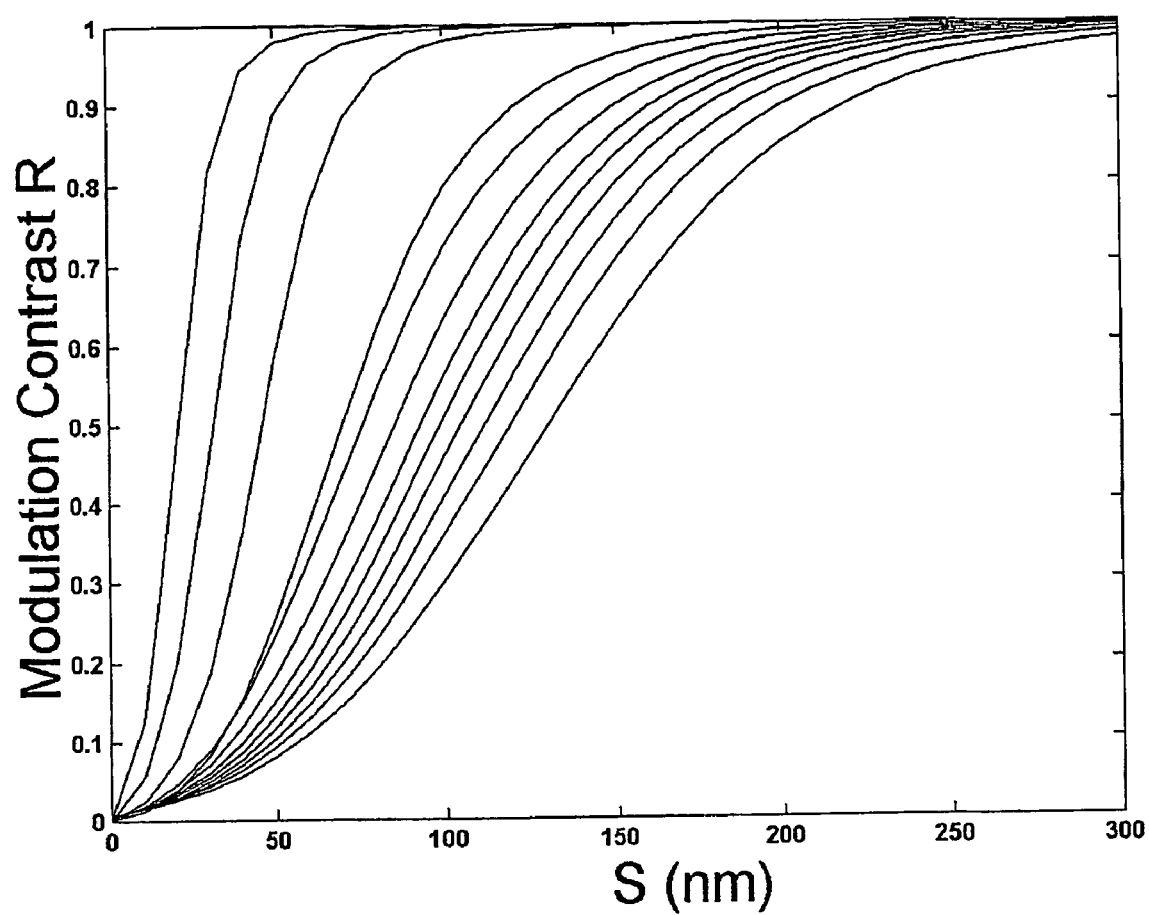
FIG. 17 shows a graph of the wavelength dependence of R as calculated by the analytical adaptation function of Example 7.

A plot of several calibration functions obtained using the previous relation is shown in Example 7 and FIG. 17.

A major obstacle to high resolution light microscopical analysis of small fluorescence objects in biological or individual polymer applications is the low number of detected fluorescence photons; therefore, preferably an important part of the invention relates to a method to determine the influence of photon noise on the size measurements. To achieve this, extensive Spatially modulated illumination-virtual microscopy simulations of the effect of photon count noise were performed.

To illustrate further the invention, examples for four different excitation wavelengths (in four independent detection channels), $\lambda_{ex}$=360 nm; =488 nm; =588 nm; =647 nm were executed. For details see Example 8 and FIG. 18. The application to any other excitation wavelength, refraction index, numerical aperture of the fluorescence collecting objective lenses, number of channels, monochromatic and chromatic aberrations, number of photons and other optically relevant parameters, registered is obvious for anyone trained in the art, using the invention. The Spatially modulated illumination-VIM simulations allow to estimate the theoretical limits of size measurements in the different channels. In each channel, 3D diffraction image intensity distributions were produced for extended objects of a given size S. The total number of detected photons was fixed to be $N_{tot}$=10,000. Before performing image analysis of the virtual data, appropriate Poisson noise was added to the 3D intensity distribution of the object; for each specimen, 40 different acquisitions were made.

In addition, two other conditions were studied: In the first, the excitation wavelength $\lambda_{ex}$ and the emission wavelength $\lambda_{em}$ were assumed to be the same; in the second condition, a difference between the excitation and the emission wavelength was assumed. It is obvious for anyone trained in the art to use also other differences as those shown here, applying the invention. In Example 9 and FIG. 19, a comparison is shown between an ideal calibration function (compare Example 3, 4) and the result obtained under the non ideal photon count condition described above for the case in which the emission and excitation wavelength were considered to be different. The large bars represent the region where the variability of R is high, due to slight instabilities in the calculation of the adaptation function. Obviously, these instabilities do not impair the usefulness of the calculation mode used.

In Example 10, the results of the virtual Spatially modulated illumination-microscopy for R=R{S} assuming that excitation wavelength and emission wavelength are equal, are listed in Table 1 for the wavelengths 360 nm; 488 nm; 568 nm; 647 nm, and $N_{tot}$=10,000 photons. For each wavelength, the axial sizes were determined from R a) using the graphical visualisation of the calibration function columns A (see Example 3, Example 4,) b) using the analytical calibration function columns B (with the help of a set of programs described below, with the application Examples 6, 7) or c) using the linear approximation formula columns C (see Example 5). As expected, the accuracy in evaluation depends on the "true" size S of the extended object that is evaluated, and even more on the wavelength used. As the "true" size of the object in the Spatially modulated illumination-VIM microscopy simulations the size value assigned as the starting point of the calculation was assumed. For each excitation wavelength, the accuracy of the size evaluation was better in the region where the graph was fairly well approximated by a linear fit function. This region changes for different excitation wavelengths. Using lower excitation wavelengths and the non-linear calibration mode, "true" extended object sizes/diameters S as low as 20 nm were detected with an error (standard deviation) of a few nanometers for the conditions assumed in the example. Using a linear approximation calibration mode, "true" extended object sizes/diameters S down to about 40 nm were correctly detected by the Spatially modulated illumination-evaluation procedure. Using longer wavelengths, "true" extended object sizes/diameters S up to about 200 nm were correctly determined.

Figure 20:
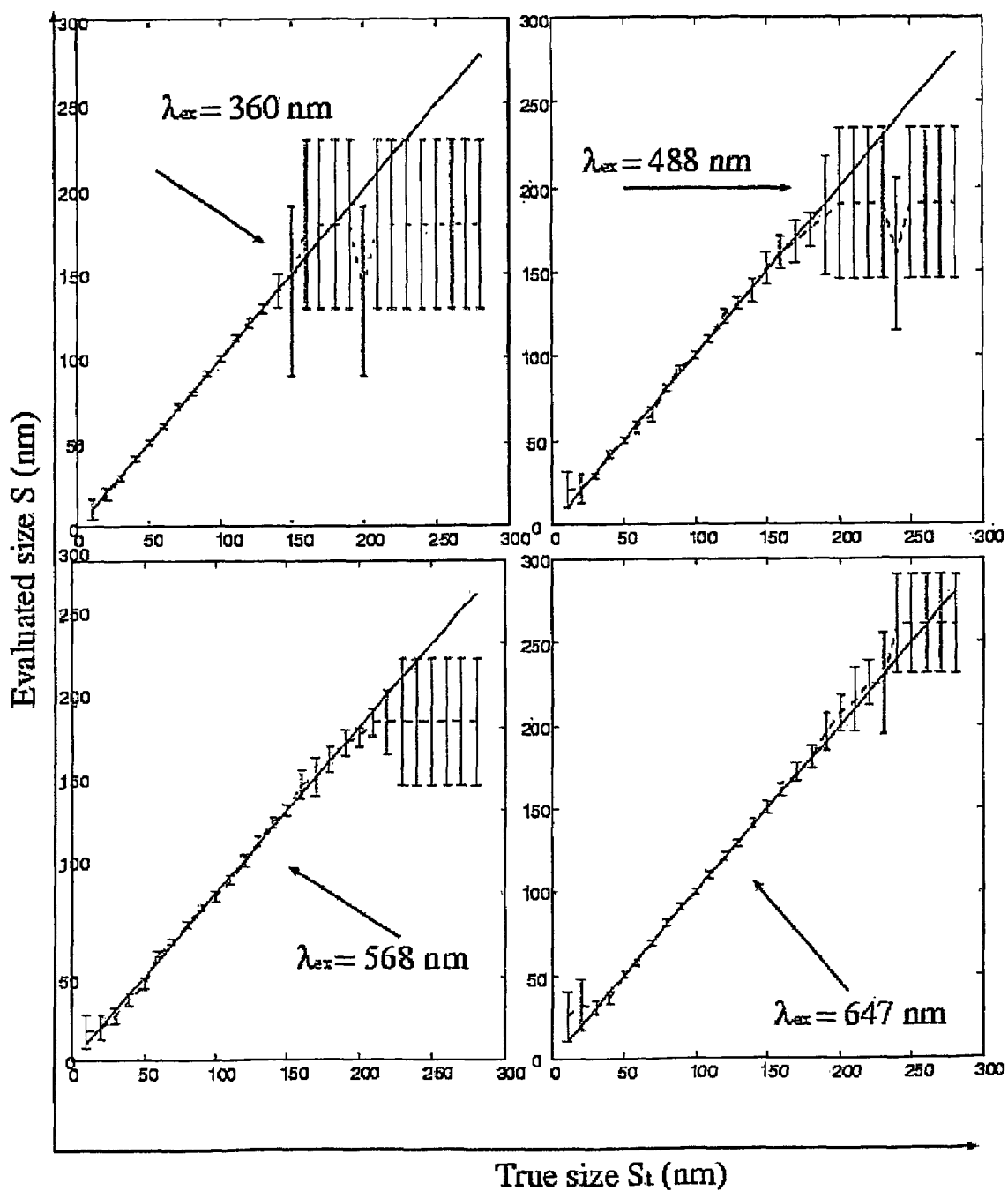
FIG. 20 shows a graphical visualization of the results shown in Table 1 (Example 10), columns A.
Figure 21:
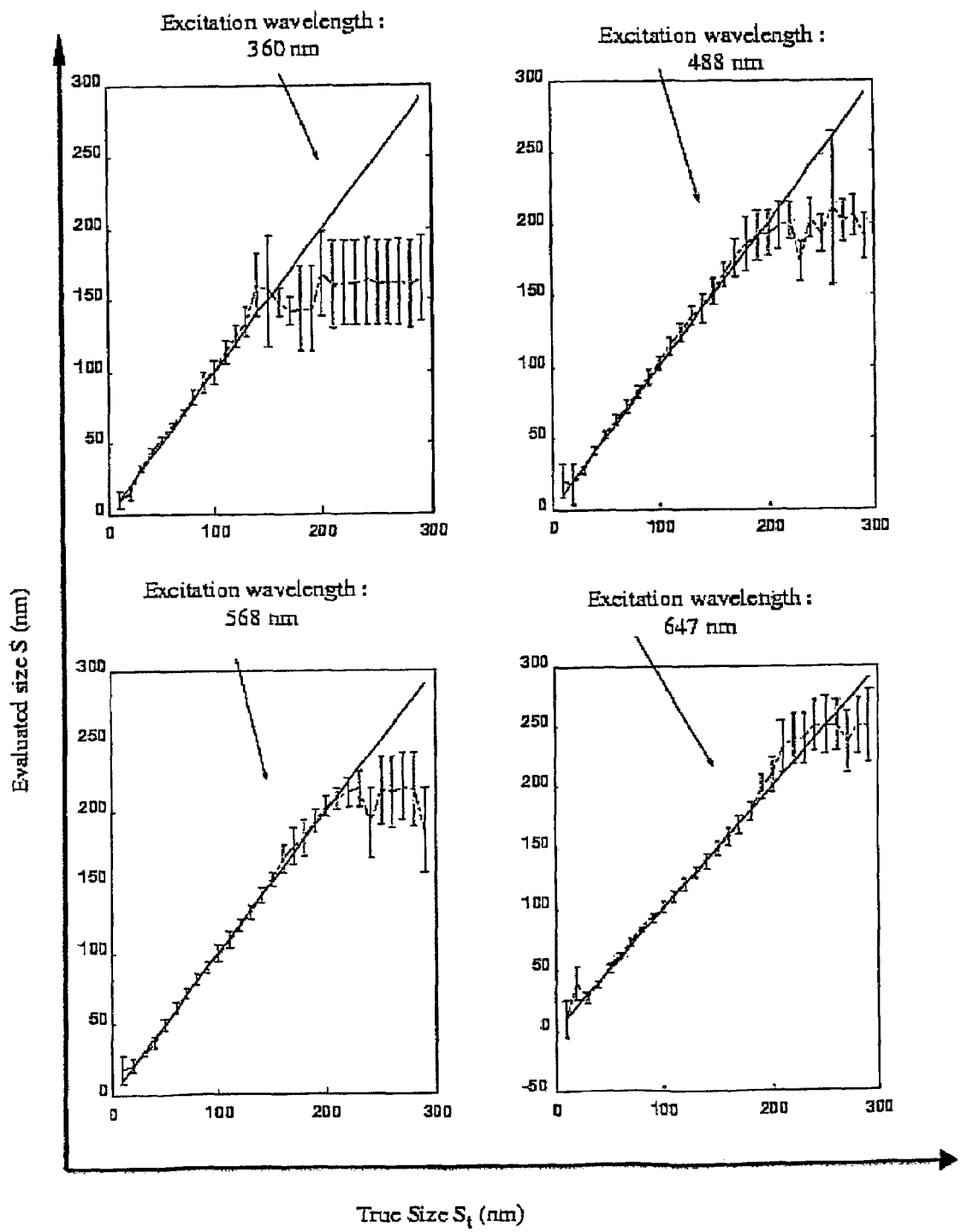
FIG. 21 shows a graphical visualization of the results shown in Table 1 (Example 10), columns B.
Figure 22:
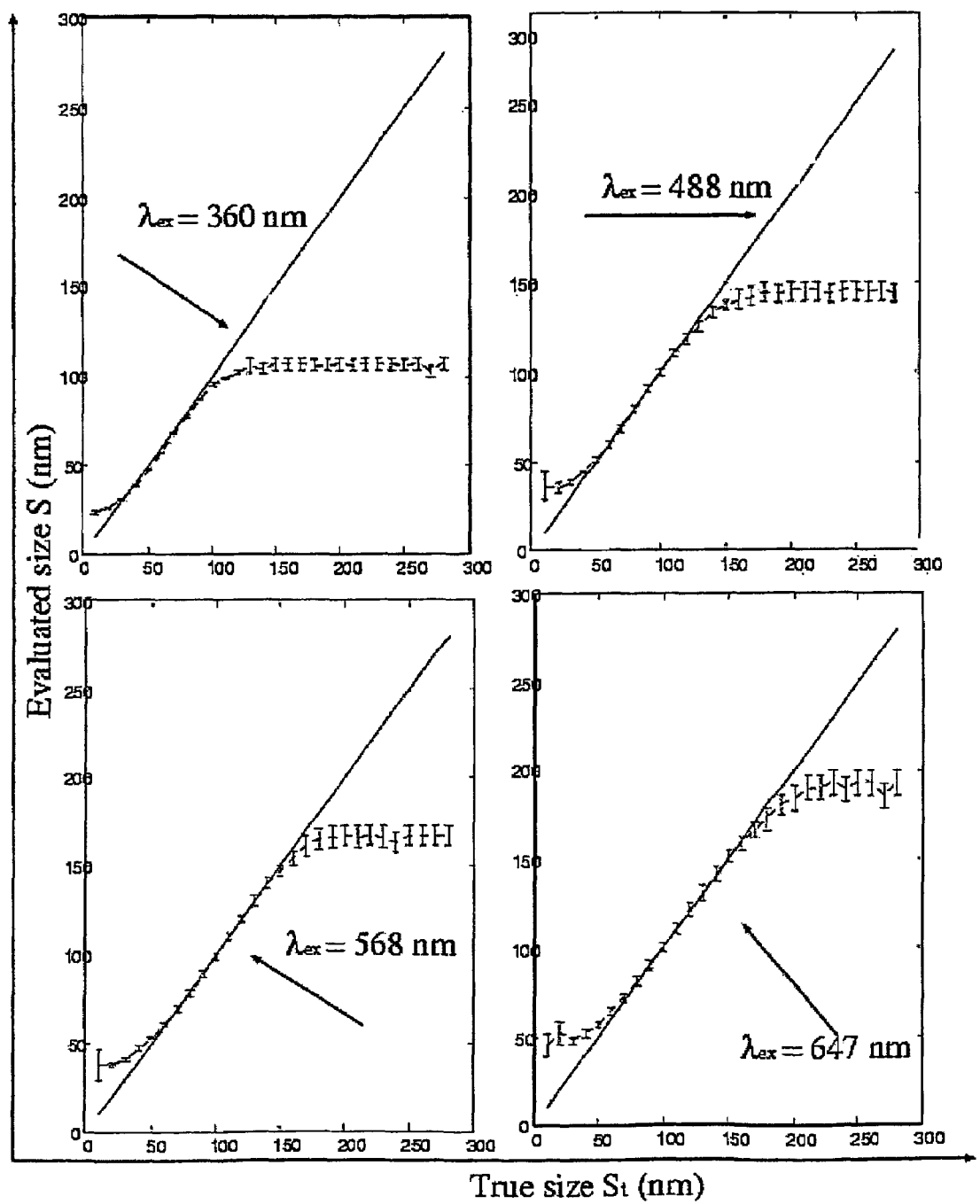
FIG. 22 shows a graphical visualization of the results shown in Table 1 (Example 10), columns C.

Examples 11, 12 and 13, respectively FIGS. 20, 21 and 22 show the relationship obtained between "true" size/diameter St and detected size S determined according to any of the embodiments of the invention. Example 11 describes the relationship for the excitation wavelengths 360 nm, 488 nm, 568 nm, 647 nm and a total number of 10,000 registered photons, using the analytical calibration function and the related inversion software; in Example 12, for the same conditions as in the previous example, a direct evaluation of the calibration functions determined (see Examples 3,8) was studied. Example 13 shows the relationship under the same conditions as in Example 11 and 12, but calculated using the linear approximations. The most simple correlation between "true" size $S_t$ and "evaluated" size S is given by the continuous straight line, using the linear approximation mode. The vertical bars indicate the standard deviation obtained under the assumption of a Poisson noise corresponding to a total number $N_{tot}$=10,000 of fluorescent photons detected for each object. For each excitation wavelength, the range where the linear approximation can be used successfully is given by the region with small size error bars. It is obvious for any one trained in the art to insert other noise distributions in the virtual Spatially modulated illumination-microscopy calculation, e.g. an appropriate combination of Poisson noise and camera read out noise.

After the evaluation of the parameter R was made, the size computation was performed using the analytical calibration function (see Examples 6, 7) and using the Virtual Microscopy calibration function (see Examples 3,4), given in the Table 1 in Example 10 in the left and in the center column, respectively; or the linear approximation formula (Example 5) was used, given in the Table 1 (Example 10) in the right column.

Example 14, respectively Table 2 shows the results of a size determination under the condition of a difference between the excitation wavelength and the corresponding emission wavelength: $\lambda_{em}=\lambda_{ex}+100$ nm. A comparison of the results of Example 14 with those of Example 10 shows that similar results are obtained for both cases above sizes of ca. 30 nm: in case a) $\lambda_{ex}=\lambda_{em}$; in case b) $\lambda_{em}=\lambda_{ex}+100$ nm. This indicates that using reasonable Stokes-shifts, the size evaluation on the whole does not critically depend on the small enlargement of the FWHM of the enveloping curve (corresponding to the detection Point Spread Function of the collecting objective lens. Problems may occur to distinguish 10 nm and 20 nm sized objects under the large Stokes-shift of 100 nm assumed. This problem can be overcome by using still shorter wavelengths for excitation, or shorter Stokes-shifts, or both. An extension of the determination of R to any other excitation wavelength and emission wavelength according to the invention is obvious for any one with knowledge in the field.

Figure 23:
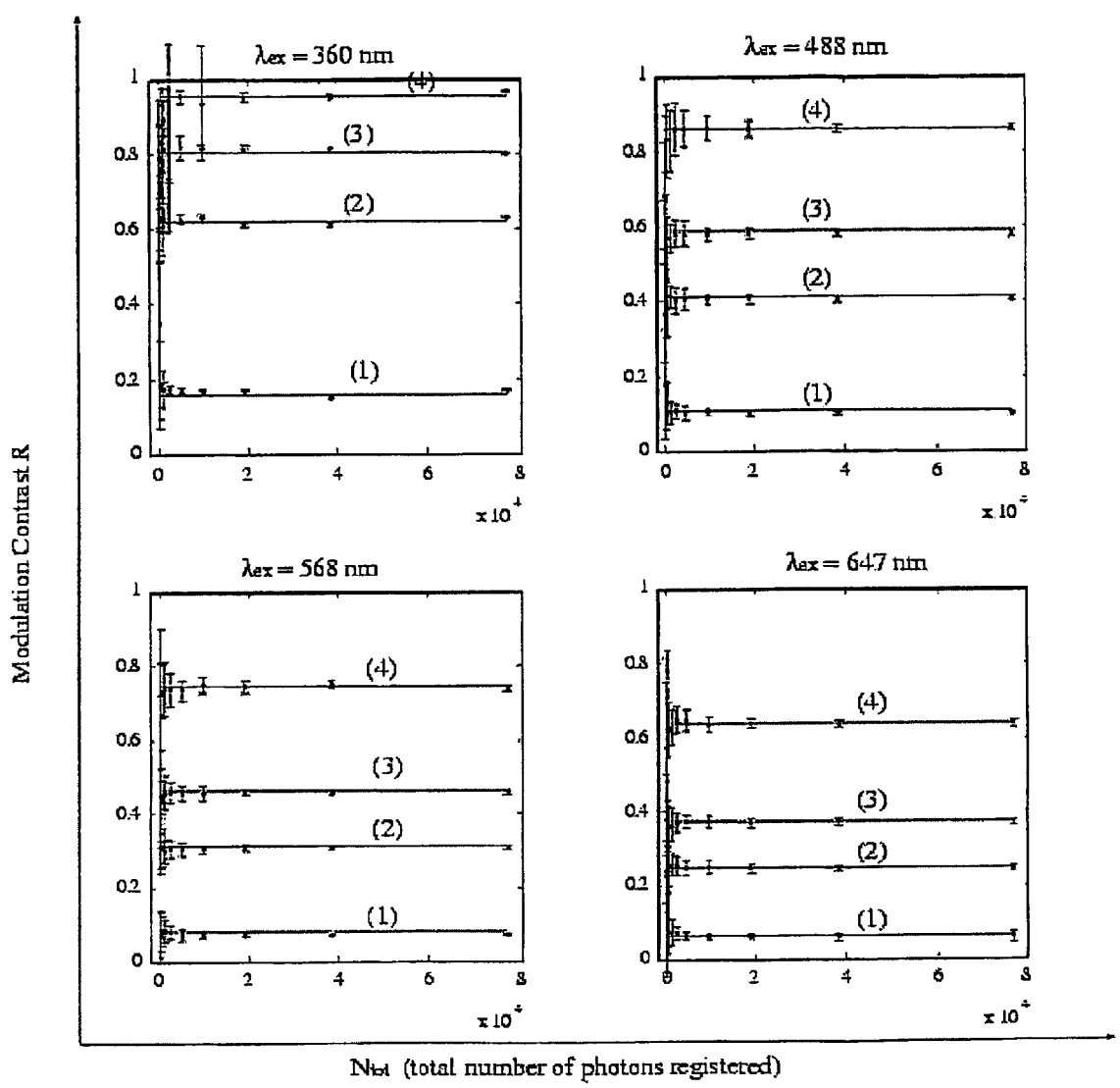
FIG. 23 shows the evaluation accuracy of modulation contrast R and size S as function of the total number of detected photons of Example 15.
Figure 24:
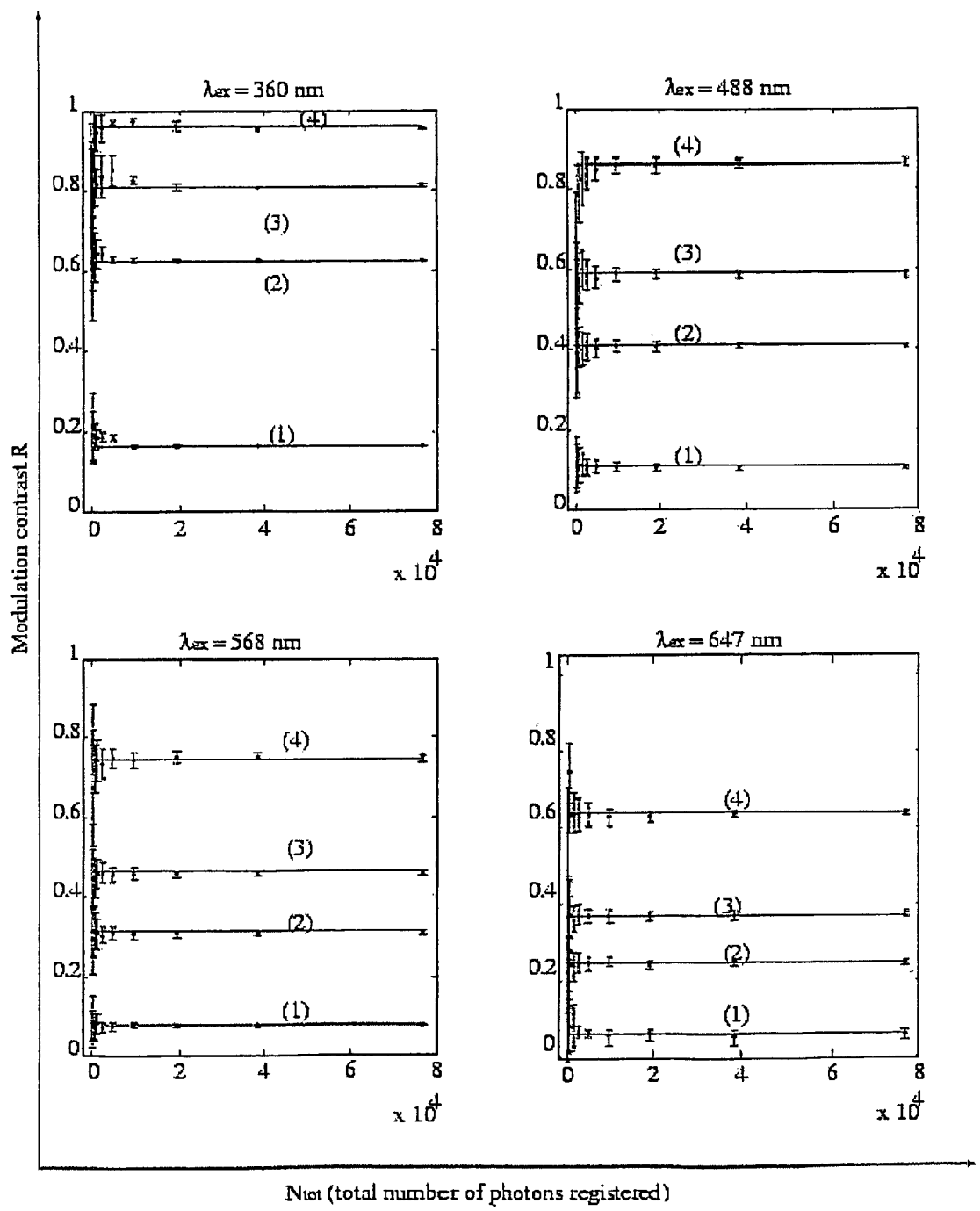
FIG. 24 shows the evaluation accuracy of modulation contrast R and size S as function of the total number of detected photons of Example 16.

In Examples 15 and 16, respectively FIGS. 23 and 24, it is shown how the dependence is between the total number of photons registered ($N_{tot}$) and the accuracy in the determination of the modulation contrast R depending on size see (1), (2), (3), (4). In these cases the condition a) and b), respectively were considered. In particular, it was studied for a fixed value of the modulation contrast R how the accuracy of its determination changes varying the total number of photons detected. It is important to point out that a fixed value of the modulation contrast factor corresponding to different values of object sizes depends on the effective wavelength $\lambda^*_{ex}$. As it is expected, the higher the photon counts, the higher is the accuracy in modulation contrast R and consequently in object diameter (size) determination.

Examples 17 and 18 show how the calibration functions change considering for different photon count conditions in the case a) ($\lambda_{ex}=\lambda_{em}$) and b) ($\lambda_{em}=\lambda_{ex}+100$ nm), respectively.

Examples 15, 16, 17, 18 help any one expert in the field to determine the optimal conditions to realise high precision experimental size determination and to figure out the advantages or the drawbacks of the method applied in different experimental conditions. Further it is important that under both conditions, a strong dependence of R as a function of S on the excitation wavelength $\lambda_{ex}$ was noted and quantitatively and analytically calculated in dependence of the optical conditions, such as the value of the excitation and the emission wavelength; the numerical aperture of the collecting objective lens used and generally, the Point Spread Function of the fluorescence light collecting system; the number of fluorescence photons registered. It is obvious for any one trained in the art that the way of calculation of R described here can be extended to other forms of modulated illumination or otherwise structured illumination, such as in the lateral (x,y) plane; to other forms of noise, such as read out noise of the camera, to other excitation and emission wavelengths; to the simultaneous use of different excitation and emission wavelengths or fluorescence lifetimes to measure the sizes of any objects labelled with such spectral signatures; to errors in chromatic calibration; to errors in the discrimination of different fluorescence lifetimes etc.

A still further most preferred embodiment of the invention, may also be used to determine the distance between two "point like" objects labelled with the same spectral signature and having a distance smaller than the Full-Width-at-Half-Maximum of the individual fringes of the spatially modulated illumination ($FWHM_f$). Example 19 shows an example for the dependence of R on the distance between the two "point like" objects. In the example shown, unequivocal distances measurements are feasible for distances below 60 nm. It is obvious for anyone trained in the art that the invention can be used to determine the dependence R on distance for any other optical condition mentioned.

Preferably, the invention may be used to determine the extension of any fluorescent object in the direction or directions where this extension is below a certain limit, in particular for object extensions below or around 200 nm, using visible light in the range from 0.4-0.7 µm for excitation of fluorescence. Furthermore, the invention can be preferably used as described in Example 19, to improve the MacroMolecular Complexes topological analysis.

Figure 28:
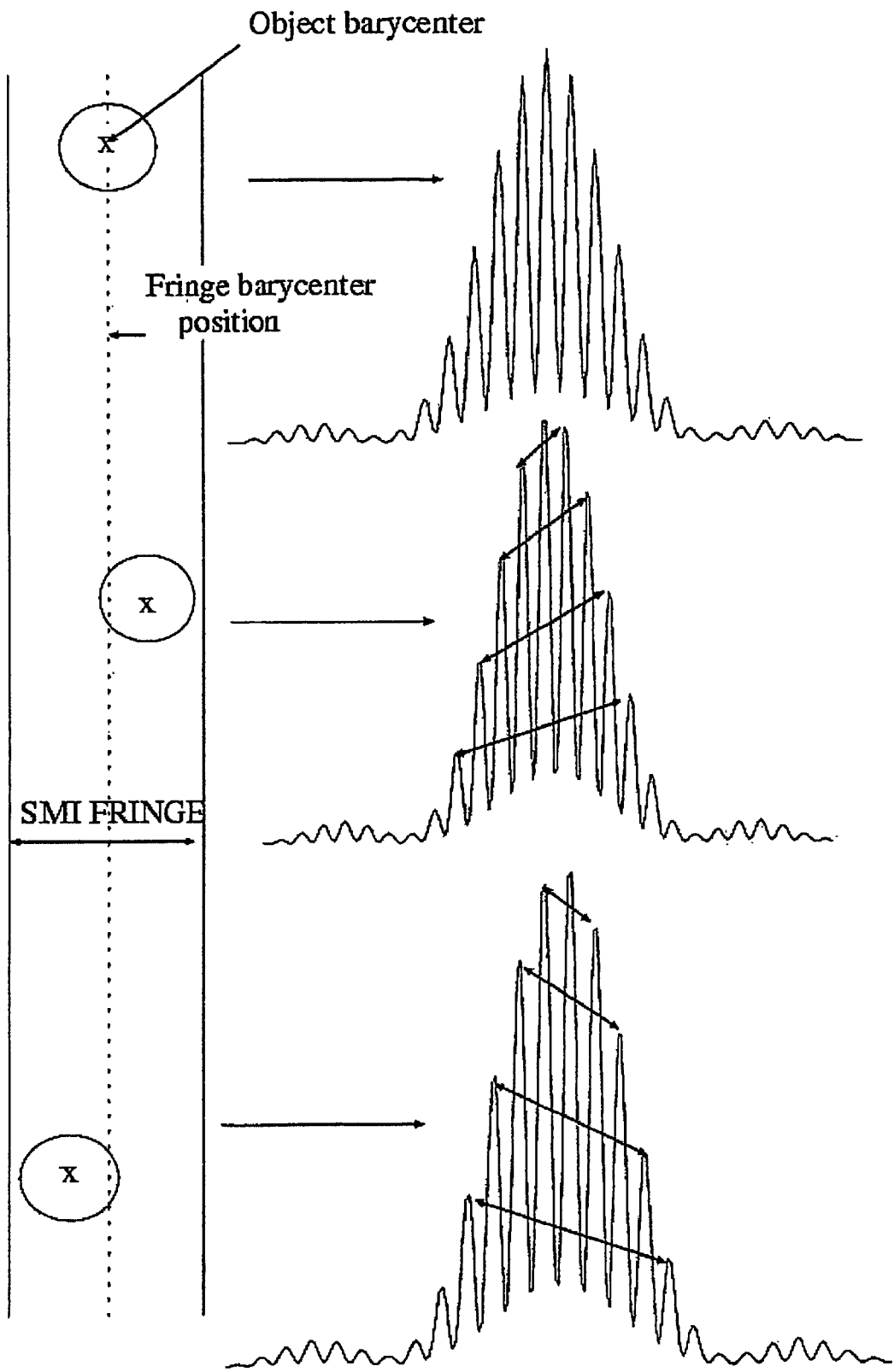
FIG. 28 shows a schematic example of the virtual microscopy evaluation of the object barycenter position in respect to the fringes barycenter of Example 20.
Figure 29:
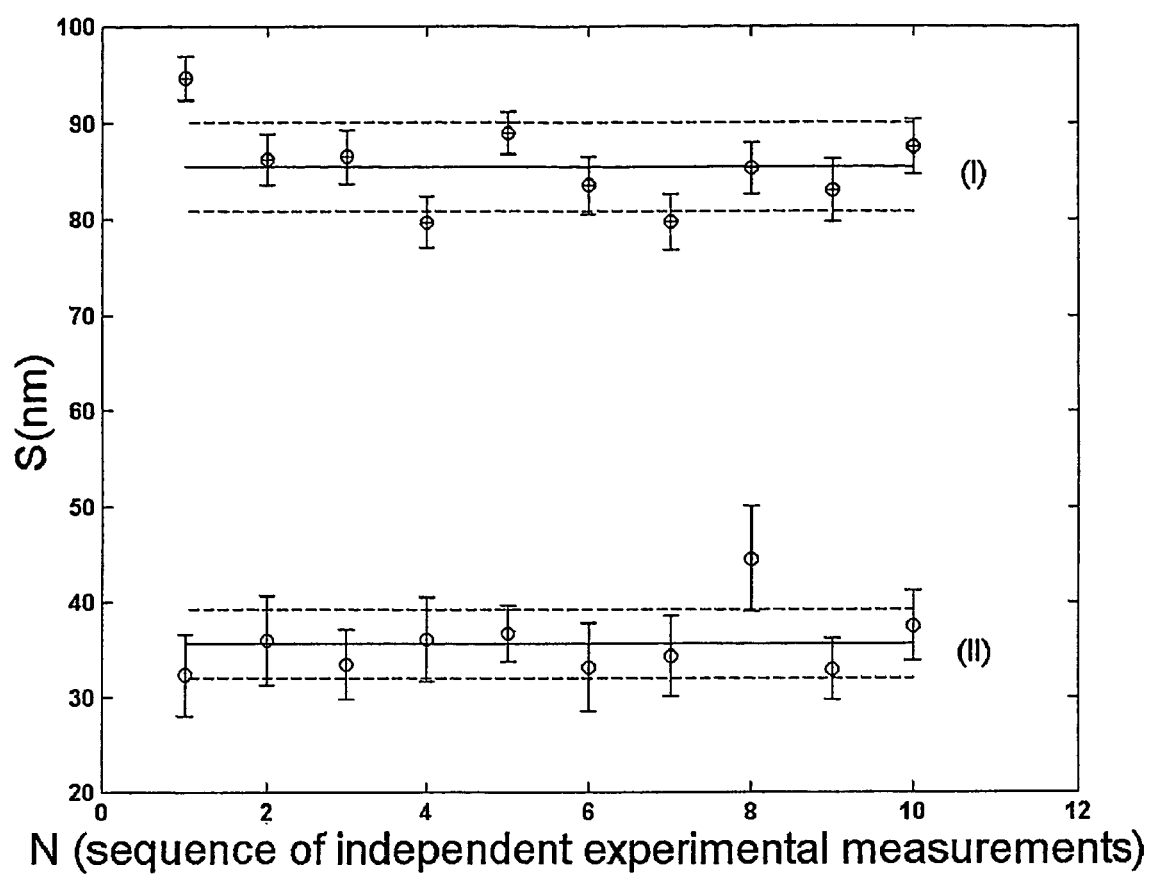
FIG. 29 shows the results of experimental data analysis of Example 21.

In fact, as it is shown in Example 20, respectively FIG. 28, the method also allows to determine the position of the barycenter of an extended object with respect to the fringe pattern barycenter also in the case that such an object is not symmetrically positioned in the fringe pattern. Example 21, respectively FIG. 29 shows the results of the methods applied on experimental measurements.

Perspectives of the Invention

Since Ernst Abbe in 1873 formulated his famous relation describing the limits of resolution in a light microscope, any access appeared to be barred to the three-dimensional (3D) structure and temporal dynamics (3D-structure plus time=4D-geometry) of complex nanosystems such as the dynamic structures constituting the basis of life. This principal limit of knowledge appeared to be a direct consequence of the physical nature of light. In the 130 years since then, thanks to the progress of science and technology, many new methods have been discovered and successfully applied to increase knowledge of complex nanostructures in all disciplines of science, such as X-ray analysis and X-ray microscopy, Transmittance Electron Microscopy [1EM], Scanning Electron Microscopy [SEM], electron tomography, neutron diffraction analysis, Atomic Force Microscopy, Near Field Scanning Optical Microscopy, or FRET-microscopy. All these methods have contributed essentially and still contribute to improve our understanding of the structure of complex nanosystems. Each system has been shown to be needed in its special range of applications: Thus, the experience of the last 130 years is that to understand the 3D-structure of such nanosystems, and especially the most complex 4D geometry of living systems, a spectrum of microscopical techniques is needed and to be broadened by new methods.

Especially, this spectrum has to be broadened by methods to study the structure and dynamics of nanosystems in the interior of thick transparent specimens, such as BMM, in the interior of cells and under "physiological" conditions, eventually "in vivo". This, however, requires methods of Far Field Light Microscopy capable to break the "Abbe limit of resolution" at least under certain, structure relevant conditions. Since strictly speeding the "Abbe limit" refers to the situation in coherent illumination, for fluorescent microscopy one may speech of the "Rayleigh limit of resolution" [J. T. Frohn, H. F. Knapp, A. Stemmer, True optical resolution beyond the Rayleigh limit achieved by standing wave illumination. Proc. Natl. Acad. Sci. USA 97, 7232-7236 (2000)]. In practice, however the differences in the actual resolution estimates are small. Here, only recently it became clear that by using physical principles and technologies completely unknown at the time of Ernst Abbe and Lord Rayleigh, such an improvement of far field light microscopy is indeed possible. Examples for these new developments are 4Pi-confocal microscopy, or Stimulated Emission Depletion microscopy. These methods break the "Abbe Limit" in the sense that the "smallest detectable distance between any two objects" may be considerably smaller than predicted by the respective formula for any conventional Far Field Light Microscope.

In addition, the advent of multispectral fluorescence labelling of specific molecules has allowed to realise additional ways to topological nanostructure analysis by the application of Spectral Position Distance Microscopy. The present invention "Light MicroscOpical Nanosizing" [LIMON], adds to these new possibilities. From the optical point of view, LIMON is more limited than Point Spread Function narrowing approaches like 4Pi-confocal microscopy and Stimulated Emission Depletion—microscopy, since like previously described Spectral Position Distance Microscopy—techniques it does not provide an increased optical resolution in the sense of a narrowed Point Spread Function. Thus in LIMON, the "smallest detectable distance between two objects" can be decreased below the smallest "conventionally" detectable distance only by imposing certain constraints on the objects to be measured, such as appropriate fluorescence labeling, or number of objects within the observation volume. From the application point of view, however, these constraints are much less disturbing: A detailed analysis of the strategies necessary for LIMON-analysis shows that LIMON is a powerful new tool to analyse for example the structure and dynamics of a wide range of complex nanosystems, down to the molecular level. The reason for this is that due to the large amount of scientific tools available today to analyse the chemical composition and to estimate structural properties of complex nanostructures, e.g. in molecular cell biology and human and mammalian genome research, so much is already known about the system that in contrast to the past, the role of Far Field Light Microscopy is often to answer very specific questions. A few examples for this may be mentioned briefly: How fast do certain, already well known molecular components colocalise to form a functioning system; How are proteic and/or nucleic acid subunits of known molecular structure arranged in a functional complex; Is the size and topology of such a complex in the living cell the same as observed in the electron microscope (recent experience has shown that this is often not the case); How do size and topology of an intracellular nanostructure change with cellular activities under the influence of well defined other agents and molecules, including e.g. not only the effects of thousands of different but identified macromolecules in a cell but also including pharmaceutical drugs, ionising radiation, and electromagnetic fields; What is the velocity of assembly and disassembly of specific nanostructures; How does this velocity change under "physiological" conditions and under the influence of other agents and molecules; What is the variability of nanostructure topology under physiological conditions, eventually in the living cell; Which of the topological conformation alternatives of a nanostructure predicted by Biocomputing approaches based on the X-ray structures of the subunits is under physiological condition and in the intact cell. These and many others questions are important problems to be solved, and can in many cases be answered using LIMON and/or Spectral Position Distance Microscopy—techniques. These techniques usually require specific fluorescence staining; this staining requirement, however, at the present stage of molecular cell biology and human & mammalian genome research, is obligatory practically for a very wide range of problems to be answered by light microscopy.

LIMON is a method to analyse the spatial information of an object, e.g. the size and topology of subwavelength sized objects, such objects being in particular polymeric structures and supramolecular complexes composed of several to many units fluorescence labelled with an appropriate number of one or more spectral signatures, or any other fluorescent structures, having a subwavelength size at least in one spatial direction, by using Spatially modulated illumination microscopy or other methods providing SI in the object plane, in combination with special calibration procedures obtained by "virtual microscopy" based specially designed information technology tools.

Figure 5A:
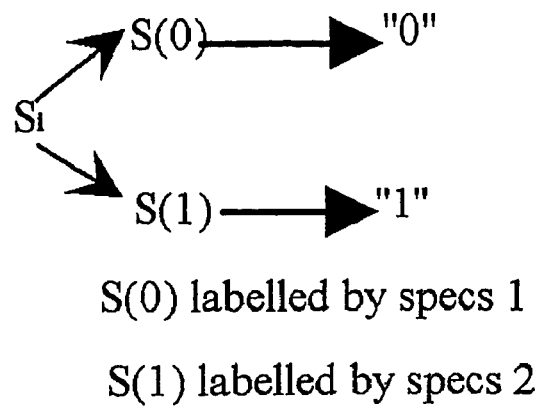
FIG. 5A illustrates schematically the determination of the MacroMolecular Complexes (MMC) bar code.
Figure 5A:
Figure 5B:
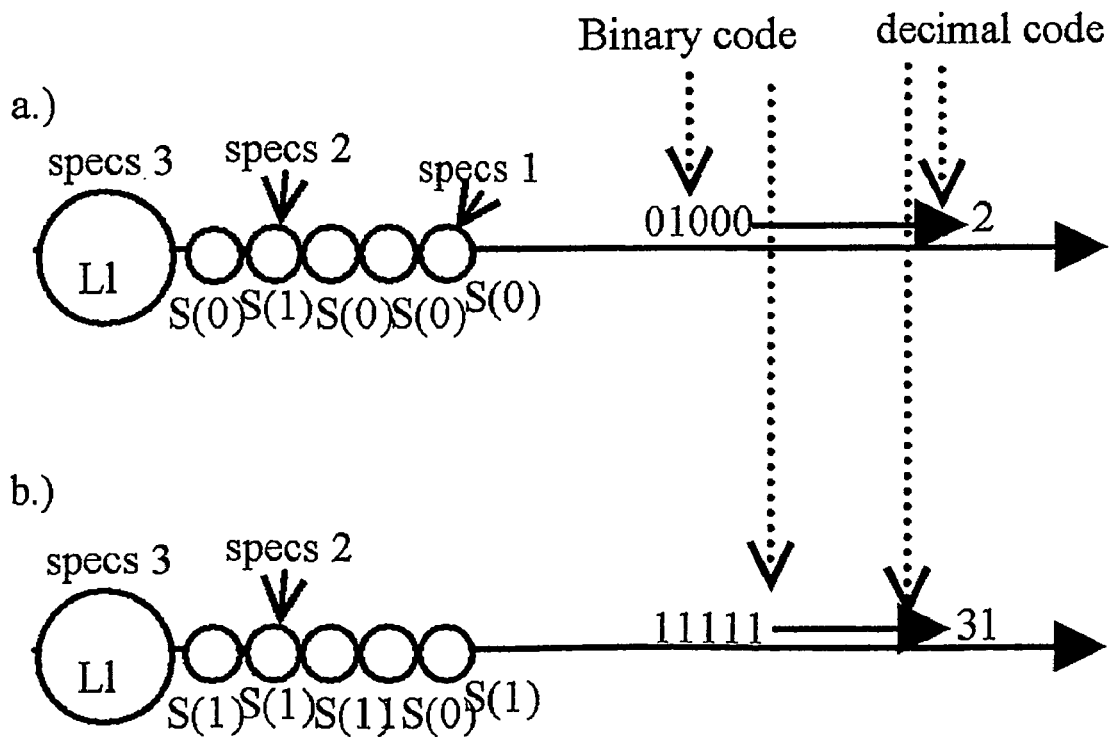
FIG. 5B shows a schematic example of determination of the MacroMolecular Complexes (MMC) bar code in case of the first five binary digits.
Figure 6A:
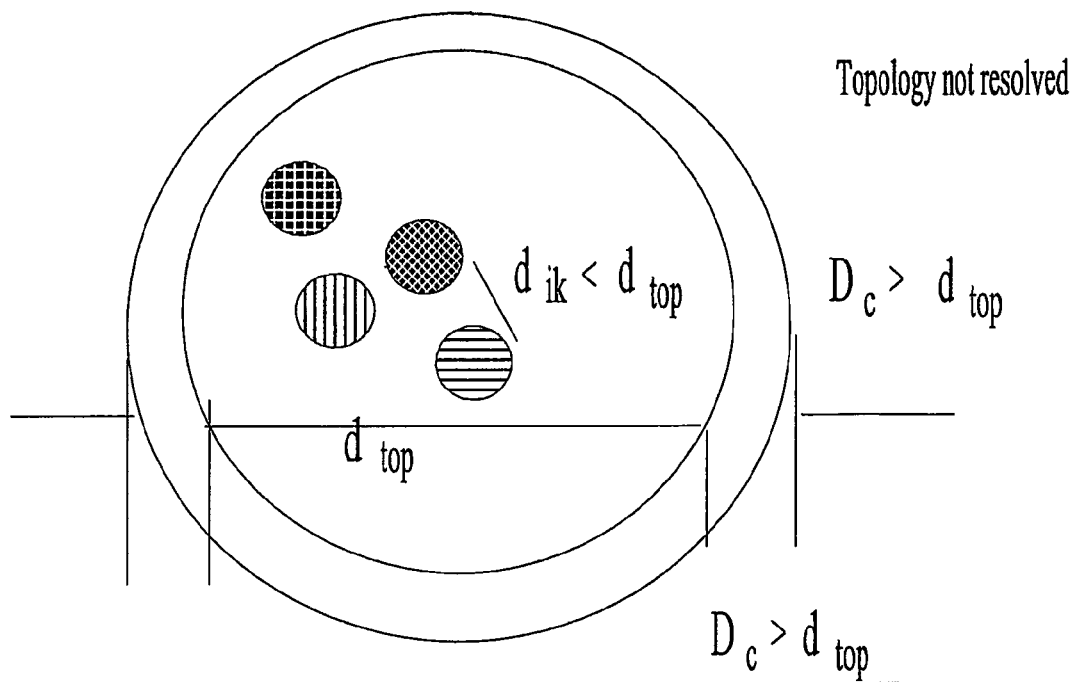
FIG. 6A shows a schematic example of the limits for topological analysis by Spatially modulated illumination SMI in case the topology is not resolved.
Figure 6B:
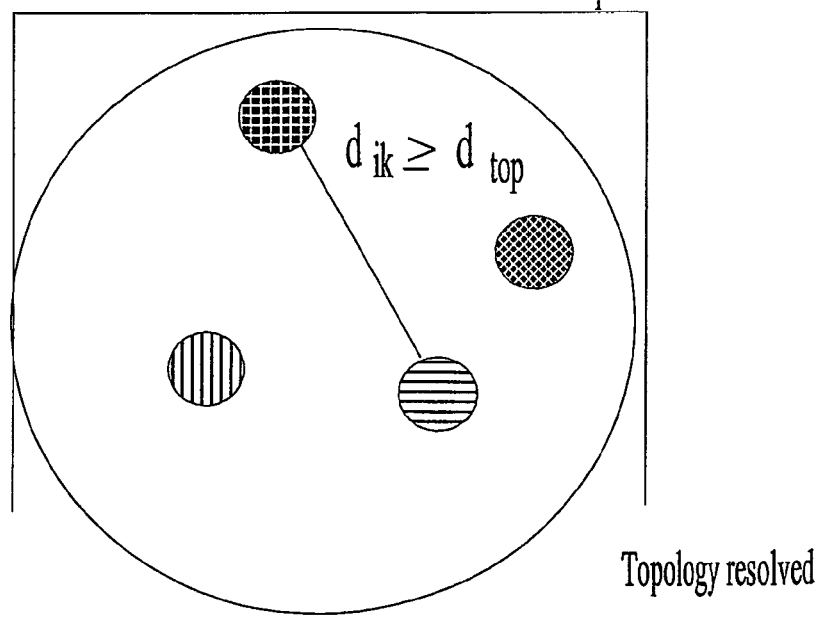
FIG. 6B shows a schematic example of the limits for topological analysis by Spatially modulated illumination SMI in case the topology is resolved.
Figure 10:
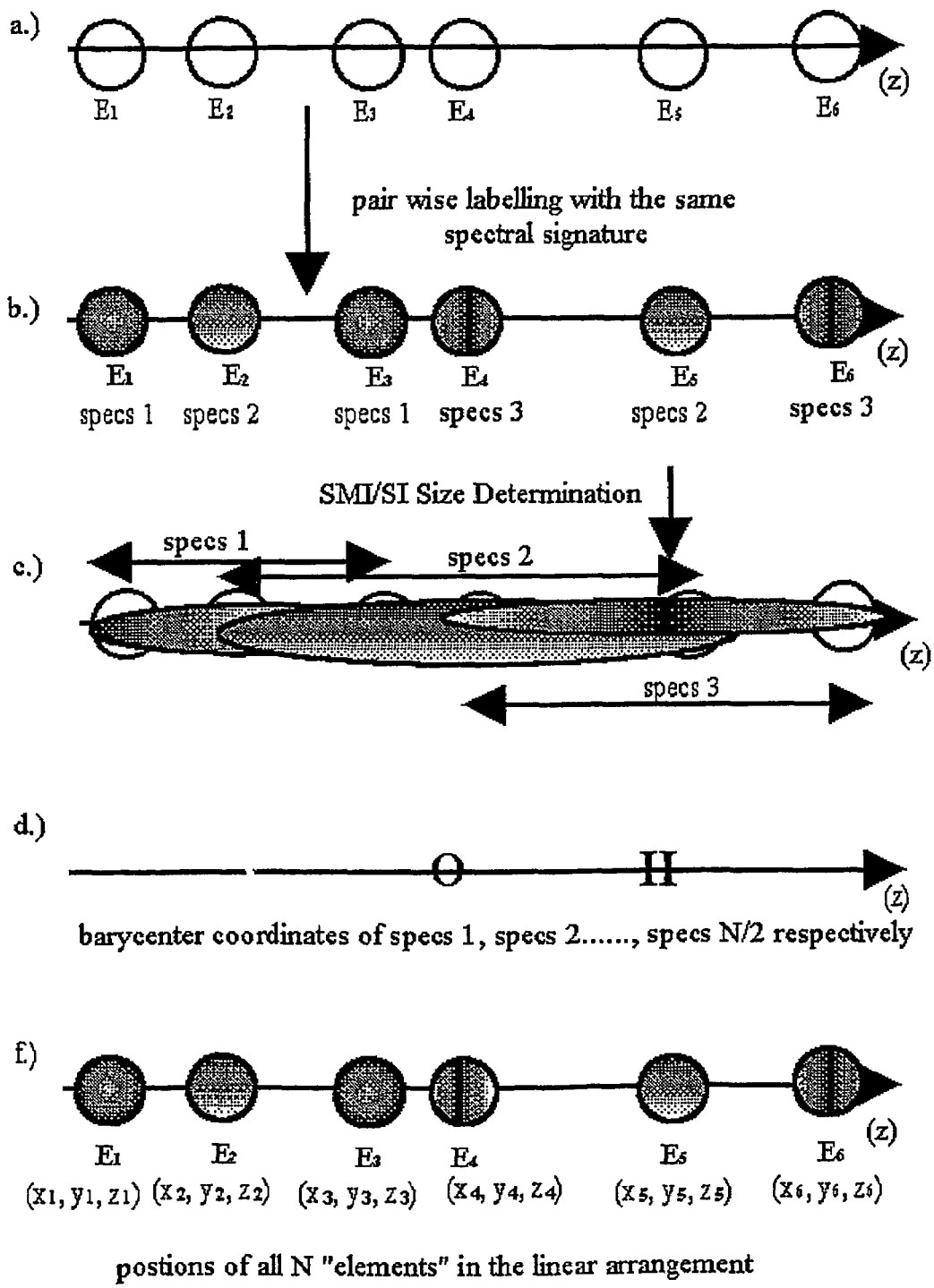
FIG. 10 illustrates the determination of the arrangement of a linear sequence of elements.

LIMON allows a far field light microscopic size and colocalization resolution of an extended fluorescent object, such as a polymeric structure, a MMC, in particular a BMM, in the order of a few tens of nanometers, even if a minimum number of only one spectral signature labelling is available. In combination with appropriate multispectral labelling protocols, a topological resolution/colocalization resolution in the few nanometer range is achieved. As an example, for a number of problems in cell biology, in particular in human and mammalian genome structure research, this will allow to reach the domain so far held by electron and X-ray microscopy, as well as Atomic Force Microscopy and Near Field Scanning Optical Microscopy methods. At the same time, however, all the established advantages of Far Field Light Microscopy are maintained: Nondestructiveness; multispectral imaging potential; observations of MacroMolecular Complexes in the interior of thick transparent specimens, especially in the interior of 3D-conserved ("intact") and even living cells. Together with appropriate specific molecular labelling techniques down to the single molecule level [Knemeyer, J.-P., Marmé, N., Sauer, M. (2000) Probes for Detection of Specific DNA Sequences at the Single-Molecule Level. Anal. Chem. 72, 3717-3724] and image analysis procedures, using these conditions a preferred embodiment of the invention allows to analyse by means of Far Field Light Microscopy in particular the arrangement, size, and topology of MacroMolecular Complexes, in particular of BioMolecular Machines or BioMolecular Modules, such as the nanostructure of specific sites of the human genome and their dynamics in intact and even living cells. Since now the major elements of life (such as genome sequence, biochemistry, individual protein sequences and their structure) are known, the optical analysis of the cellular and in particular the nuclear nanostructure and its dynamics will become one of the major issues in the understanding of the specific organisation of cells and their differences, e.g. in different stages of development, in different tissues, or in different pathological conditions. Such an improved understanding of the "4-D geometry" of life will be of utmost importance for a better understanding also of the structural basis of genome reprogramming, one of the fundamental problems of modern biology and medicine. From this follows a wide range of practical applications of LIMON, for example:

The analysis of the "compaction" of specific genetically active and inactive gene regions in three-dimensionally (3D) conserved ("intact") cell nuclei, including artificial chromosomes or other gene vectors introduced in a cell nucleus. Using e.g. LIMON-conditions allowing to measure quantitatively the size of a specifically fluorescence labelled gene region in the order of 30-50 nm diameter, gene regions as small as a few kbp in DNA sequence length can be analysed. This corresponds to the sequence length of even relatively small genes. If such a small gene region is transcribed by transcription factories with a size in the order of 50 nm, it will be decondensed to a degree which can be measured by the LIMON technique even using labelling with one spectral signature only. Another application example is the estimate of copy number of gene by size determination, on a cell by cell basis. This is interesting e.g. in such case where differences in the overall intensity of the registered fluorescence label are not sufficiently reliable;

If a number of gene regions each corresponding to the conditions mentioned in 1) is to be analysed for genetic activity correlated "compaction" changes, each of these regions can be labelled by a different spectral signature and analysed for "compaction" by LIMON;

The methods described above allow compaction analysis up to chromatin regions in the order of 200-300 nm, choosing the appropriate Spatially modulated illumination/Structured illumination SMI/SI conditions;

If a number of gene regions each corresponding to the above conditions is to be analysed, and if these gene regions have a minimum distance from each other which is either larger than the lateral (x,y) optical resolution, or larger than the axial (z) optical resolution, then combinatorial labelling schemes [M. R. Speicher, G. S. Ballard, D. C. Ward (1996) Karyotyping human chromosomes by combinatorial multifluor FISH: Nature Genet. 12: 368-375.] can be applied. For example, using $N_{spec}$ different spectral signatures, $2^{Nspec}-1$ different gene regions can be identified in a cell nucleus. In each of these identified gene regions, the size of this region can be determined by LIMON using a minimum of one of the spectral signatures used for labelling. For example, if Nspecs=4, the compaction of 15 different gene regions in a given nucleus can be determined by LIMON; if Nspecs=8, the compaction of 255 different gene regions in a nucleus can be determined by LIMON. Since the observation volume in Spatially modulated illumination-microscopy is in the order of 0.1 $\mu m^3$, in principal a combinatorial labelling of a large number of gene regions is feasible e.g. in a human cell nucleus, having a typical volume in the order of 500 $\mu m^3$. Thus, LIMON analysis of cells with combinatorially labelled gene regions provides a possibility to use the entire cell like a "DNA expression chip". Although the number of genes to be analysed is considerably smaller, it is still sufficient to allow important analysis types. A great advantage, however, with respect to DNA expression chips is that this method allows a considerably faster and more economical cell-by-cell-analysis. The relatively limited number of gene regions to be analysed by LIMON in a cell can even advantageous from the clinical point of view: Methodologically, the LIMON analysis has to be restricted to the interesting part of the genome. Some examples for application of LIMON are: Selection of gene regions with cell type specific genetic expression and "compaction" patterns allows to discriminate different cell types light microscopically on the cell-by-cell level, using LIMON. Under these conditions, LIMON analysis of gene regions allows to analyse the determination of cells before other signs of differentiation become visible, on a cell-by-cell level. In cases where the labelling can be performed in the living cells e.g. [T. Tsukamoto et al. 2000: Visualisation of gene activity in living cells. Nature Cell Biol. 2, 871-878], the cell type and or the state of its determination/differentiation can be identified by LIMON even "in vivo" on a cell-by-cell level. Using suitably fast CCD-cameras for registration, Spatially modulated illumination-data registration is possible in the one-second range. During this time, Brownian movements of gene region is sufficiently slow to allow "compaction" analysis. Special examples for application of this on a cell-by-cell level are: Discrimination of cancer cells and normal cells in a tissue section; follow up of cell determination/differentiation in ontogenetic development; follow up of genetic changes in stem cells related to further differentiation; changes in the genetic expression pattern induced by pharmaceutical drugs, by ionising radiation, by electromagnetic fields, or by environmental chemicals;

The sequence differences between homologue chromosomes in mammalian cells such as in human cells are assumed to be usually very small, except for the sex chromosomes. The difference is believed to be in the order of 0.1%. This amounts to sequence differences between autosomes in the order of 3 Million base pairs, or in the order of 100 kbp per chromosome. As a continuous sequence, 100 kbp may amount to a size in the order of 100×10 nm of a folded 30 nm chromatin fiber [T. Cremer & C. Cremer, Chromosome Territories, Nuclear Architecture and Gene Regulation in Mammalian Cells, Nature Reviews Genetics Volume 2, 292-301 (2001)]. In Human Genetics, examples are known where homologues differ from each other by small continuous pieces of DNA sequences. If in a chromosome in a given region only a small sequence length difference of a few kbp can be identified, then LIMON allows to distinguish the two autosomes. This can either be done by labelling the small sequences directly and then measure size differences in the two homologues; or by labelling flanking sequences. Examples for practical applications of this method are: The identification of homologues with imprinting regions, such as the maternal and paternal human chromosome #15; the identification of many or all homologues on a cell-by-cell basis; the identification of maternal or paternal chromosomes carrying cancer correlated or other disease correlated genes, on a cell-by-cell basis; the stem line identification of stem cells on a cell-by cell basis using the homologue identification pattern;

The improved assignment of individual DNA sequences to given sites on the linear sequence map of a chromosome, measured on a cell-by-cell-basis, in particular in cell nuclei: Whereas the Spectral Position Distance Microscopy—methods described in the "state of the art" allow to assign the site of a short DNA-sequence with high precision if neighbouring sequences are labelled with different spectral signatures, due to the complex folding of the chromatin fiber this method may give equivocal results if the linear sequence distances become larger. Using the a preferred embodiment of the invention, the folding of the chromatin fiber can be taken much better into account, and hence the reliability of assignment can be improved. This applies also to analysis of artificial chromosomes or other gene vectors, e.g. used gene therapy approaches;

The improved analysis of the folding of the chromatin fiber in a given region: Whereas the Spectral Position Distance Microscopy—methods described in the "state of the art" allow a detailed analysis of the folding of the chromatin fiber, e.g. in a specific gene region, only if a high and thence technically difficult realisable number of spectral signatures is applied, in a preferred embodiment of the invention a combination of topological and size measurements is used; following established principles of geometrical analysis, this leads to a considerably improved folding analysis, using the same number of spectral signatures;

The measurement of the size of a BMM other then a gene region, such as the size of a nuclear pore in vivo in Far Field Light Microscopy under specific conditions; the size of a replication factory; the size of a transcription factory; the size of repair complex; the size of a proteasome; the size of a membrane protein cluster; the size of an ion-channel. The sizes of such BioMolecular Machines or BioMolecular Modules are well known from electron microscopy, as well as Atomic Force Microscopy and Near Field Scanning Optical Microscopy. However, due to the special conditions necessary to perform such measurements, the large scale observation of thousands of such BioMolecular Machines or BioMolecular Modules under special physiological conditions, such as multiple drug testing has been difficult to impractical. LIMON analysis, if necessary in combination with special nanolithographic procedures as disclosed in DE 100 52 823, included herein by reference, allows to speed up such measurements considerably;

In LIMON-supported Spectral Position Distance Microscopy—analysis of topology, LIMON considerably extends the possibilities of previously revealed Spectral Position Distance Microscopy analysis of topology. For example, if for the topological analysis of a BMM the determination of the relative positions and mutual distances of 16 "point like" elements is required, the solution of this problem due, to those previous procedures requires the specific labelling of the 16 elements with 16 different spectral signatures, followed by the spectrally discriminated registration of the fluorescence of 16 spectral signatures. Although this is in principle technically possible, it is presently very difficult to perform. In the LIMON supported solution of this problem, instead of labelling all 16 elements with different spectral signatures, 8 pairs of elements are labelled with 8 different spectral signatures. For each pair, the distance between the "point like" elements, their joint fluorescence intensity barycenter, and the relative orientation of the vector connecting the calculated positions of two elements are determined applying the LIMON method as described. From this, the relative positions and mutual distances of all 16 element are determined. This way of LIMON supported topology analysis can be extended in an analogous way to any other number of elements allowing spectrally differential labelling and registration;

Another example of LIMON supported topology analysis refers to the measurement of the topology of BioMolecular Machines or BioMolecular Modules containing a large number of equal elements, e.g. of proteins of the same kind, or nucleic-stretches with the same sequence of bases or base pairs. A way to solve this problem is to bring such a BMM together with a mixture of reporter molecules, such as fluorescence labelled nucleic acid aptamers where each of the elements can bind one of these reporter molecules only. For example, a BMM Contains 12 equal elements. If the mixture contains reporter molecules with 12 different spectral signatures, then each of the 12 elements has 12 possibilities to be labelled; this gives a total of $12^{12}=8.9 \times 10^{12}$ possibilities of labelling. For normal Spectral Position Distance Microscopy analysis (i.e. without LIMON), only those label patterns are useful where each spectral signature in a BMM analysed is occurring only once. This is the case in $12!=4.8 \times 10^8$ cases. Thus, the overall probability to encounter in a specific BMM analysed the kind of labelling useful for Spectral Position Distance Microscopy analysis of the topology of all 12 equal elements is estimated to be $12!/[12^{12}] =5.4 \times 10^{-5}=1/18600$. To analyse such a number of BioMolecular Machines or BioMolecular Modules is technically possible using nanolithographic approaches as described in DE 100 52 823 included herein by reference. Using LIMON supported Spectral Position Distance Microscopy, instead of BioMolecular Machines or BioMolecular Modules with all 12 equal elements labelled by chance differently, it is sufficient that only 6 pairs of elements are labelled with 6 different spectral signatures. This can be performed by subjecting the BioMolecular Machines or BioMolecular Modules to a mixture with types of reporter molecules of 6 different spectral signatures. Then, element 1 has 6 possibilities for labeling; since pairs with the same label are allowed for LIMON-supported Spectral Position Distance Microscopy, also element 2 has 6 possibilities of labelling; element 3 has to be labelled with one of the remaining 5 spectral signatures to be useful for Spectral Position Distance Microscopy analysis; element 4 again has 5 possibilities for LIMON-supported Spectral Position Distance Microscopy, since pair with the same label are admitted, etc. In the end, $6 \times 6 \times 5 \times 5 \times 4 \times 4 \times 3 \times 3 \times 2 \times 2=[6!]^2=518,400$ useful labelling possibilities exist. The probability for such a useful labelling is then $P=[6!]^2/6^{12}=518,400/2.2 \times 10^9=2.4 \times 10^{-4}$. In this case, one in about 4,200 can be analysed by LIMON, whereas in the other case of the previous Spectral Position Distance Microscopy methods, one BMM in about 18,600 only has the right label. Thus the use of LIMON in these cases is also highly advantageous. The example given may easily be extended to other number of elements and spectral signatures;

LIMON allows another possibility to read DNA "Bar codes", or any other bar code arranged and labelled as described above, by far field light microscopy. An example of the determination of the MMC Bar Code is shown on FIGS. 5A and 5B., wherein specs denotes the spectral signature. The analysis of the arrangement of the linear sequence is explained in more detail in FIG. 10, wherein for convenience an orientation in z direction is assumed. Any other direction where SMI/SI excitation occurs can be used according to the invention. In FIG. 10 the liner sequence of elements $E_1, E_2 \ldots, E_6$ which for the sake of clarity is assumed to be in z direction are pair wise labelled with the same spectral signature (specs 1, specs2, specs 3) at the first step. Then step a SMI/SI discrimination is performed. Then, in the next step barycenter coordinates of specs 1, specs 2, specs 3, . . . , specs N/2 are determined. Finally the positions $(x_i, y_i, z_i)$, where i=1, 2, 3, . . . N (in FIG. 10 N=6), of all N elements in the linear arrangement are determined. This allows an identification on a cell-by-cell, or "spot-by-spot" or "field-of-view-by field-of-view-basis, with a limited number of different spectral signatures even for the encoding of high decimal numbers. For example, using LIMON analysis, 8 spectral signatures are sufficient for about $10^9$ different decimal numbers with combinatorial labelling, a considerably lower number of spectral signatures is needed for the encoding of higher decimal numbers. Examples for application are: a) All cases where DNA-bar codes are being used; for example, stem cell lines, or any other cell line, may be unequivocal identified by introducing an artificial, genetically inert mini-chromosome carrying the DNA-bar code for this line; for example, the DNA-bar code may be contain such a high number of "STOP" codons that any translation into proteins is practically impossible even after a number of point mutations and other genetic aberrations induced in such minichromosomes; b) identification on the basis of other polymer sequences, such as in specific vivo-label of even very large number of animals by innocuous polymer labels supplied in an appropriate way;

In combination with appropriate Spatially modulated illumination/Structured Illumination (SMI-SI) registration devices, LIMON allows to measure the topology of appropriately labelled elements in a MMC as well as the size of the MMC or its elements in any spatial direction desired. This latter application allows to estimate important morphological parameters, such as e.g. volume and surface, the half axes of the minimum enveloping ellipsoid, the roundness described by the relation between $[volume]^2$ to the $[surface]^3$ etc. Thus, LIMON opens a way to determine the topology and morphology of subwavelength sized objects by means of far field light microscopy to an extent so far thought to be possible only by increasing the optical resolution correspondingly;

The possibility to measure topological and morphological parameters made possible by LIMON, allows new approaches also in modelling and simulation of subwavelength sized objects, such as MacroMolecular Complexes or in particular BioMolecular Machines or BioMolecular Modules. For example, methods for modelling & simulation of human nuclear genome structures as disclosed in DE 100 52 583 A1, included herein by reference, have shown that it is possible to derive from such simulation microscopically observable parameters, such as relative positions and mutual distances between given subunits; the half axes of minimum enveloping ellipsoids; the volume, surface and the roundness of given objects; the dependence on time applying for example models including Brownian motion, etc. On the basis of such predictions, it is possible to test assumptions in a rigorous way. The validated models of human nuclear genome structure can then be used to predict more precisely important biomedical consequences, such as the mobility of drugs for gene therapy or other therapeutic purposes; the induction of cancer related specific chromosome aberrations by ionising radiation; or the functional characteristics of artificial chromosomes and other vectors, e.g. for gene therapy. On the basis of LIMON-derived determinations of topological and morphological parameters of subwavelength sized objects, such principles of modelling & simulations can now be applied in a corresponding way to the establishment of experimentally validated models e.g. of BioMolecular Machines or BioMolecular Modules or other MacroMolecular Complexes, even in the interior of cells under physiological conditions.

Further, several Examples illustrating different embodiments of the invention are described.

Example 1 and FIG. 11A and FIG. 11B illustrate the principle of SMI/SI Virtual Microscopy (VIM) and VIM visualisation of the effects of photon noise on the Axial Intensity Distribution.

FIG. 11 A.) shows the case of a point like object. The axial Point Spread Function (PSF) is the axial intensity distribution of a "point like" object. In this example, a "point like" object is any object where the Full Width at Half Maximum ($FWHM_o$) of its fluorochrome distribution is one order of magnitude or more smaller than the $FWHM_f$ of the modulation fringe pattern. In the example the PSF detected is shown in an "ideal condition" by Spatially modulated illumination microscope. Such a PSF is the result of the product between the Epifluorescent intensity distribution and the Spatially modulated illumination fringe pattern; this PSF is computed by Virtual Microscopy (VIM) using the convolution between a Dirac delta function and the theoretical Spatially modulated illumination-PSF (see C.)). A Dirac delta function is well approximated by a high intensity pulse (peak value equal to 255 in grey scale) with a $FWHM_o$ that respects the following condition: $FWHM_o << FWHM_{SMI}$. B.) Simple scheme of an Spatially modulated illumination detection system and fringe pattern. In details: on the left are visualised the two microscopical objectives positioned along the optical (z) axis and the object plane orthogonal to them. On the right is visualised the Spatially modulated illumination fringe pattern. C.) Spatially modulated illumination-VIM microscopy: on the left site it is shown how Virtual Microscopy computes the Spatially modulated illumination-PSF. On the right site is an example regarding the effect of photon noise in Spatially modulated illumination-PSF analysis. Three different photon count condition are shown assuming that the photon noise respects a Poisson statistics. In other words, Virtual Microscopy considers each point of an ideal PSF as the average value of a Poisson statistics. Each point of the ideal PSF is considered independently with respect to the others, and for each of them a random value of the statistical distribution described above is chosen. As it is shown the higher the total number of photon ($N_{tot}$) detected by the acquisition system, the closer to the ideal detection condition shape is the PSF.

FIG. 11B shows the same example as in FIG. 11AC.) for the case of the AID of an extended object. On the left the is shown the Ideal AID, i.e. the AID in the absence of noise, on the right side the AIDs in case of noise, detected for the case of three different photon counts, i.e. for $N_{tot}$=2500 in the upper right side, $N_{tot}$=10 000 in the middle right side and $N_{tot}$=40 000 in the lower right side of FIG. 11B. One may note that in both cases, the excitation wavelength used was 488 nm and that all the images for a reason of clarity are not in scale.

Example 2 illustrates the SMI-VIM Extended Object Axial Intensity Distribution computation and relation between the modulation contrast R and the size S of such an object (see. FIGS. 12A and 12B).

In this Example with respect to FIG. 12A an extended fluorescent object is represented as the incoherent superposition of point-like fluorescent objects. The axial intensity distribution of an extended object is the sum of the axial intensity distributions (PSF) of each point like object. The PSF of each object has a $FWHM_o$=10 nm. In the lower part of the left side of FIG. 12A are shown respectively the SMI PSFs. On the right side in the upper part is shown a SMI Axial Intensity Distribution (AID) with the $FWHM_{SMI}$. Below a graph of detected AID and the adaptation function are shown, wherein the detected AID is shown as a continuous line and the Adaptation function as a dotted line. For a better visualisation the fringes and the point like PSFs are not represented in the same scale. The axial intensity distribution on the right side is shown together with the adaptation function used for evaluate size parameters.

FIG. 12B is a visualisation of an example of how the axial intensity distribution (AID) depends on the size of an extended object computed using an excitation wavelength equal to 488 nm. The extended object was realised either as an ensemble of several point like objects (5 and 11 in the example, shown in the upper part, respectively in the lower part of FIG. 12B) with a total extension of 50 nm and 110 nm, respectively, giving rise to 5 and 11 Spatially modulated illumination-Point Spread Functions SMI-PSFs being 10 nm apart from each other. FIG. 14 and in more detail on the right had side. To obtain the AID of the extended object, the individual Spatially modulated illumination-PSFs are summed up. The resulting AIDs are shown on the right. Note that the modulation contrast R=$M_g$/M strongly depends on the object size, wherein Mg is the minimum, respectively and M is a maximum of the axial intensity distribution and the modulation contrast R=$M_g$/M The same AID was obtained by convolution of an object represented by a Gaussian intensity distribution with an axial Full-Width-at-Half-Maximum $FWHM_{True}$. The $FWHM_{True}$ is equal to the maximum distance between the equivalent object constituted by several point like objects as in FIGS. 12A and 12B. In the following it is assumed that the "true size" value of an object is equal to $FWHM_{True}$. For example, the object in FIG. 12B with an indicated size of 50 nm was represented by a Gaussian with the $FWHM_{True}$=50 nm. Note that for a reason of visualisation the Spatially modulated illumination-PSFs are not printed in scale. On FIGS. 12A and 12B the detected AID is shown as a continuous line and the adaptation function as a dotted line.

Example 3, respectively FIG. 13 illustrate the relation between the modulation contrast R and the object size S.

In the graph shown on FIG. 13 the calibration function R=R(s, $\lambda^*_{ex}$) (where $\lambda^*_{ex}$ is the "effective" excitation wavelength) is shown; here: $\lambda^*_{ex}$=488 nm. For sizes smaller then 20 nm the modulation contrast R is close to zero; this means that the Axial Intensity Distribution AID, in such a condition, well approximates the theoretical PSF. Increasing the size the modulation contrast also increases and the degree in modulation in AID decreases. For (S≈160 nm) the modulation contrast starts to be close to one and it is not possible detect any clear information from the AID because it does not presents any modulation in its shape; in this case small changes in the modulation contrast correspond to large changes of the size starts to be close to one and it is not possible detect any clear information from the AID because it does not presents any modulation in its shape; in this case small changes in the modulation contrast correspond to large changes of the size.

Example 4, respectively FIG. 14 illustrate the dependence of the modulation contrast R from the excitation wavelength.

In the example, respectively the graph on FIG. 14 are shown several calibration functions obtained by virtual microscopy using $\lambda_{ex}$=360 nm, 488 nm, 568 nm, 647 nm.

The figure shows that, varying $\lambda_{ex}$, the calibration function $R=R(s, \lambda_{ex})$ changes. Changing $\lambda_{ex}$, it is possible to analyse in optimal condition different size ranges. Smaller the excitation wavelength smaller the size that is possible to determine e.g. with $\lambda_{ex}=360$ nm it is still possible to evaluate, in critical photon count conditions e.g. $N_{tot}=10000$, the size of object which diameter is close to 20 nm. Bigger the excitation wavelength bigger the axial object size that it is possible to determine. With $\lambda_{ex}=647$ nm object sizes up to 200 nm can be determined with a good precision. The $\lambda_{ex}$ are vacuum wavelengths; refraction index assumed: n=1.5; Numerical Aperture of the collimating objective lenses: NA=1.4. The tilting angle between the optical axis of the collimating objective lenses is $\alpha_{tilt}=0$. For $\alpha_{tilt}\neq 0$, the calculations shown are valid for the same effective wavelengths, $\lambda_{ex}^*$ where $\lambda_{ex}^*=\lambda_{ex}/\cos(\alpha_{tilt})$. Note: n=1.5 and NA=1.4 are used also in all others examples presented. The subscript $_{ex}$ here represents the excitation light.

Example 5 illustrates the determination of the linear approximation relation between the modulation contrast R and the object size.

Figure 15:
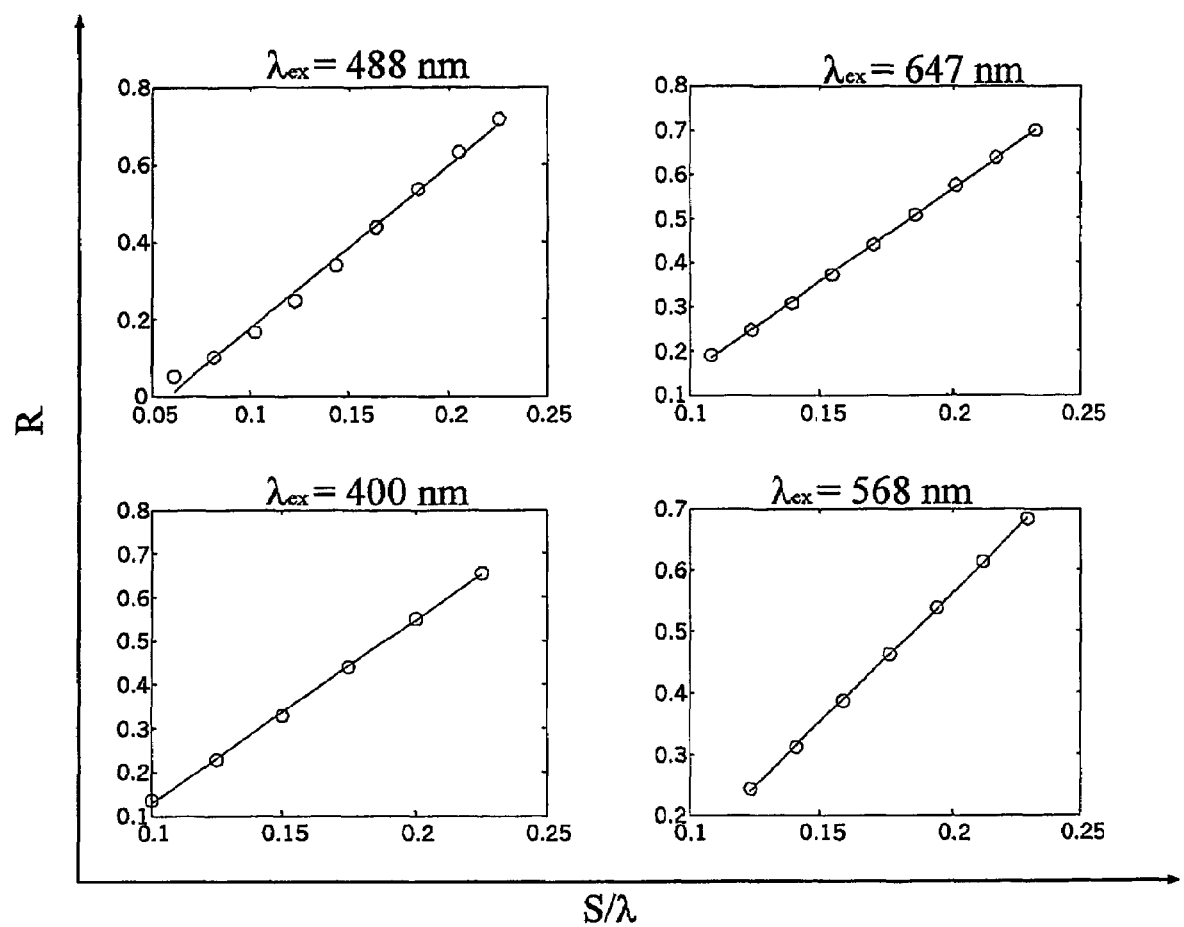
FIG. 15 illustrates the determination of the linear approximation relation between the modulation contrast R and the object size of Example 5.

Note that in the Example 5, respectively FIG. 15 the subscript "$_{ex}$" denotes the excitation wavelength. A linear relation between the modulation contrast R and the object size S can be, under appropriate conditions, determined. The linear coefficients $\alpha$, $\beta$ were calculated using all the calibration functions showed in Example 4. For each excitation wavelength $\lambda_{ex}$ the modulation contrast R was studied as a function of the ratio between the size S and $\lambda_{ex}$ varying S in a range in which the relation $R=R(s/\lambda_{ex}, \lambda_{ex})$ is well approximated by a linear function $R_L$: $R_L=R_L(s/\lambda_{ex}, \lambda_{ex})=(\alpha/\lambda_{ex})S+\beta$ ($\alpha=4.18\pm0.05$; $\beta=-0.27\pm0.02$). Using this procedure it is possible to determine independently four times (one for each $\lambda_{ex}$) the linear parameters $\alpha$, $\beta$. In the following examples it will be shown that the linear relation $R_L$ is valid (for each effective excitation wavelength) only for a limited range of values of S. The calculation shown are valid also for the same effective wavelengths $\lambda^*_{ex}$ (see Example 4).

Example 6 is a comparison of analytical adaptation function and virtual microscopy calibration function.

In this Example, it is shown one of the more important results of Spatially modulated illumination virtual microscopy: the determination, in an analytical way of the modulation contrast R:

$$R=R(s, \lambda^*_{ex})=1/\{1++B(\lambda^*_{ex})^2\exp[-(A(\lambda^*_{ex})S)^c]\}$$

where $A(\lambda^*_{ex})$, $B(\lambda^*_{ex})$ and $C=C(\lambda^*_{ex})$ are given by the following formulas:

$$A(\lambda^*_{ex})=11.19/\{(\lambda^*_{ex})^{0.74}-65.27\}$$

$$B(\lambda^*_{ex})=45.68/\{\lambda^*_{ex}-356.69\}^{0.23}$$

$$C(\lambda^*_{ex})=1/\{1.42+(11.61)\cdot\exp[-0.0081\cdot\lambda_{ex}]\}.$$

Figure 16:
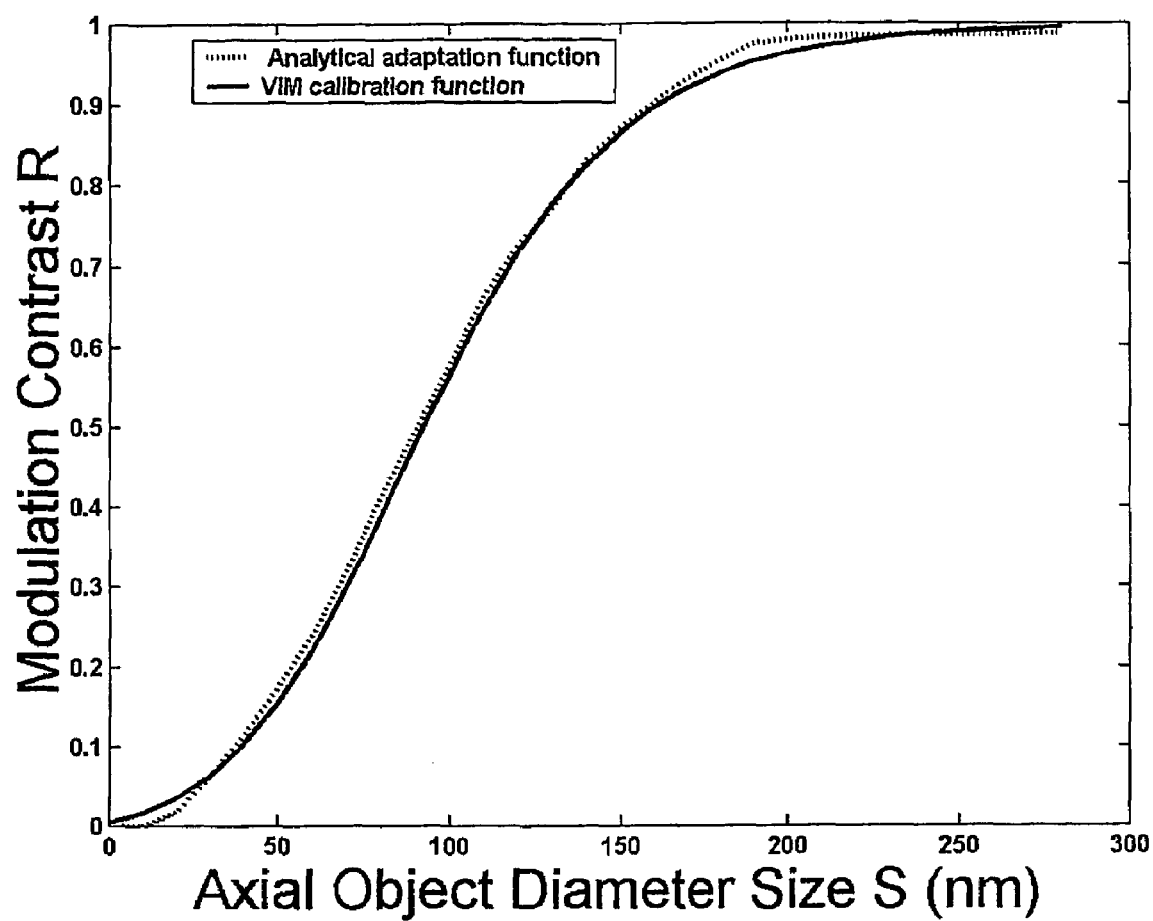
FIG. 16 shows a comparison of analytical adaptation function and virtual microscopy calibration function of Example 6.

In the FIG. 16 related with this Example it is visualised the comparison between the Virtual Microscopy calibration function computed (dotted line) by virtual microscopy, and $R(s, \lambda^*_{ex})$ (continuous line) both considering $\lambda^*_{ex}=488$ nm. The good agreement between the Virtual Microscopy's computed modulation contrast R (for definition of $\lambda^*_{ex}$ see Example 4,5) and $R(s, \lambda^*_{ex})$ shown in the Figure can be considered the prove that $R(s, \lambda^*_{ex})$ is a valid analytical expression of the modulation contrast R for other values of the effective excitation wavelength. As explained in the main text, $R(s, \lambda^*_{ex})$ was obtained fitting R evaluated by Virtual Microscopy for the following effective excitation wavelengths: $\lambda^*_{ex}=360$ nm, 568 nm, 647 nm; the calibration function relative to the case $\lambda^*_{ex}=488$ nm was not used for this purpose.

Example 7 illustrates the wavelength dependence of R as calculated by the analytical adaptation function:

In this Example several graphical representations of the calibration function realised are shown on FIG. 17 using the analytical expression of the modulation contrast R (for more details see text and Example 6). In the Figure are represented, (starting from left to right) the analytical expression of the modulation contrast R for the following effective wavelengths: $\lambda^*_{ex}=330$, 340, 350, 360, 400, 440, 488, 528, 568, 608, 647, 700 nm. The analytical expression for the calibration function described in Example 6 can be evaluated in real time regarding the special light excitation conditions in which the system is configured.

Figure 18:
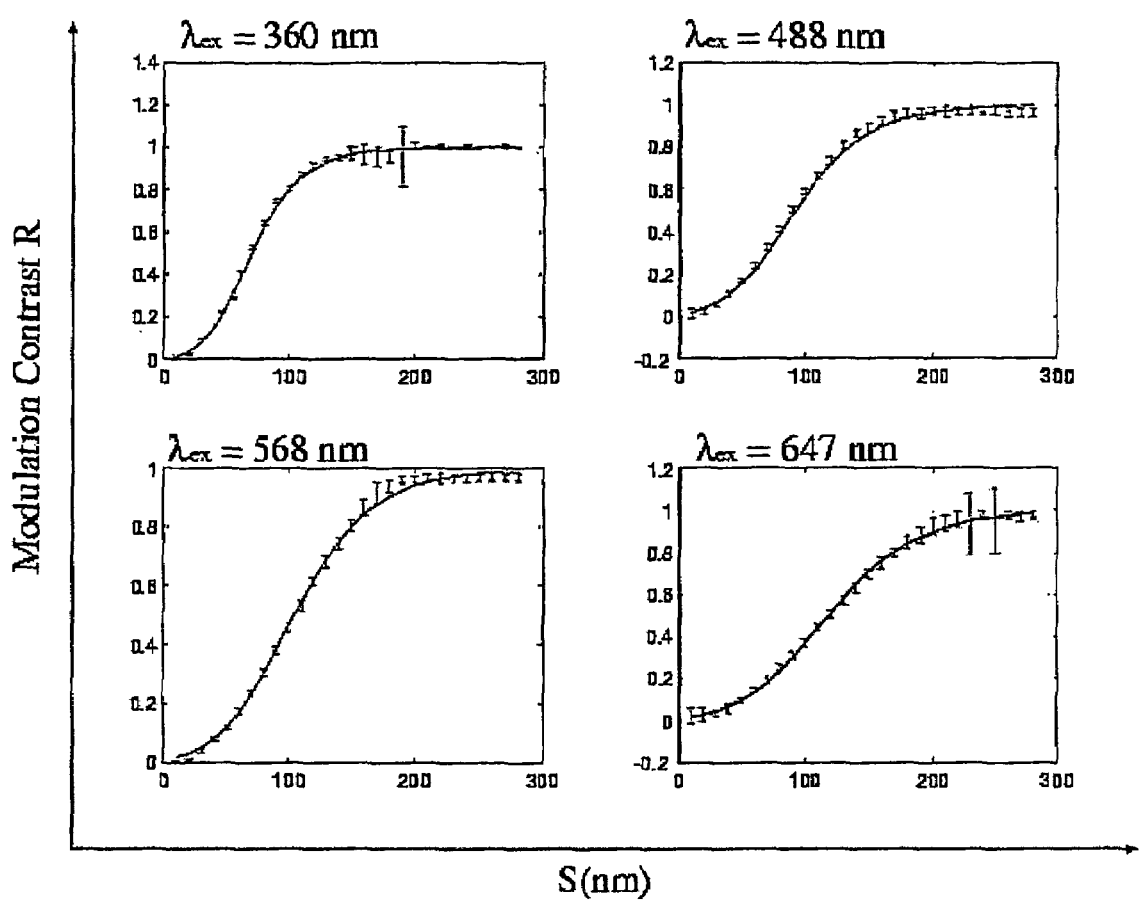
FIG. 18 illustrates the virtual microscopy determination of the modulation contrast R under photon noise condition of Example 8.

Example 8 and FIG. 18 illustrate a VIM determination of the modulation contrast R, under photon noise condition.

In this Example the effective wavelength coincides with the excitation wavelength: $\lambda^*_{ex}=\lambda_{ex}$. The curves, shown on FIG. 18 plotted with bars were evaluated assuming that the total number of photons ($N_{tot}$) registered was $N_{tot}=10000$ and that photon noise was added to the AIDs, (for more details see example 1). The abscissa of FIG. 18 shows an object diameter size S (nm) and the ordinate the Modulation contrast R. The continues lines are the calibration functions in "ideal" noiseless conditions evaluated by Virtual Microscopy.

Figure 19:
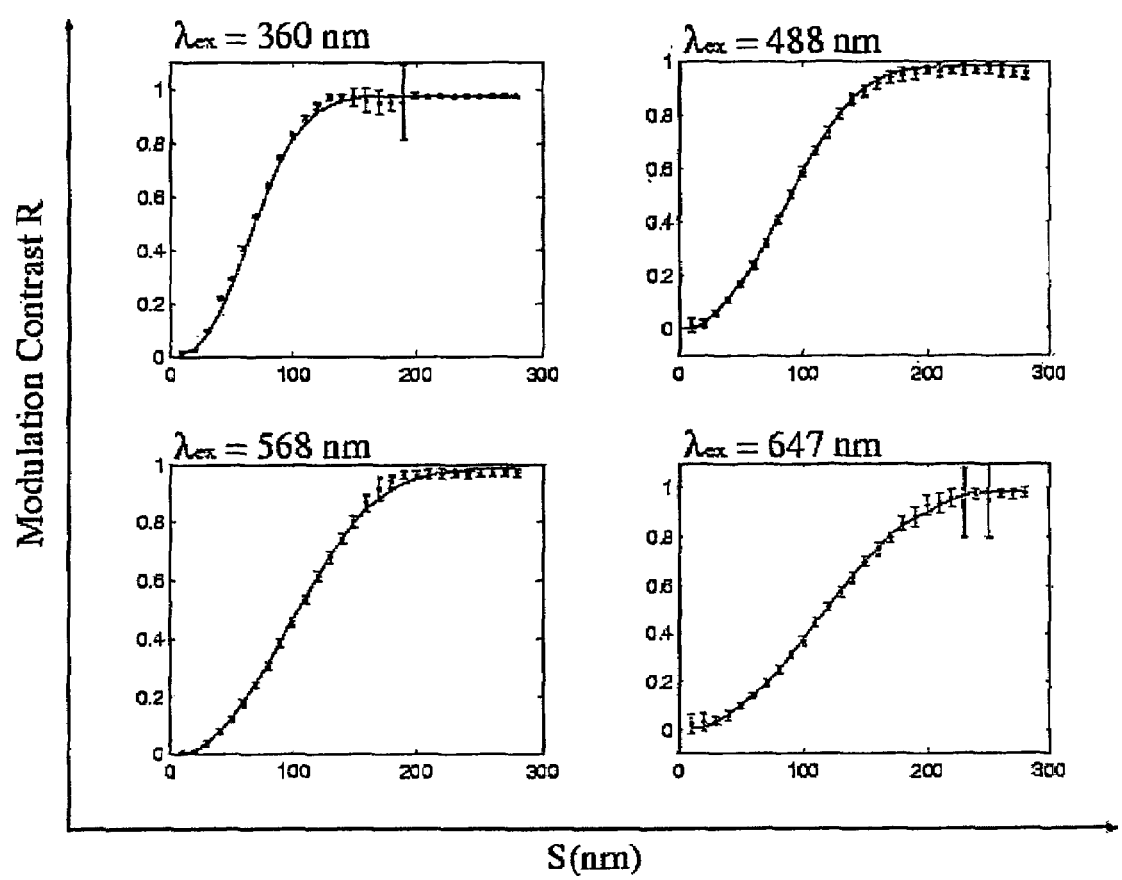
FIG. 19 illustrates the virtual microscopy determination of the modulation contrast R under photon noise condition of Example 9.

Example 9 and FIG. 19 illustrate a virtual microscopy (VIM) determination of the modulation contrast R, under photon noise condition.

In this Example the effective wavelength is assumed to coincide with the excitation wavelength: $\lambda^*_{ex}=\lambda_{ex}$ and $\lambda_{em}=\lambda_{ex}+100$ nm. The curves shown on FIG. 19 plotted with bars were evaluated assuming that the total number of photons ($N_{tot}$) registered was $N_{tot}=10000$ and that photon noise was added to the AIDs, (for more details see example 1). On FIG. 19 the abscissa shows the Object diameter size S (nm) and the ordinate: Modulation contrast R. The continuous lines are the calibration functions in "ideal" noiseless conditions evaluated by Virtual Microscopy.

Example 10, respectively Table 1 illustrate a virtual determination of object sizes using different VIM approaches.

In this Example also $\lambda^*_{ex}=\lambda_{em}$. Three different Virtual Microscopy approaches in order to determine the object size starting from the evaluation of the modulation contrast R are used. The evaluations are performed for the effective excitation wavelengths, indicated in the head row of the Table 1. Column T of Table 1 shows the "True size" values; i.e. the $FWHM_{True}$ of the objects fixed at the start of the Virtual Microscopy simulation process (see Example 2). Columns A of Table 1 show determination of the object sizes using the graphical visualisation of the modulation contrast R; for more details see Examples 3, 4 and the main text. Columns B of Table 1 show determination of the object size after inversion of the analytical expression of the calibration function $R=R(S, \lambda_{ex}^*)$, (for more details see Examples 6, 7 and the main text). Columns C of Table 1 show determination of the object size after inversion of the linear approximation of the calibration function $R_L=R_L(S, \lambda_{ex}^*)$, (for more details see Examples 5).

Example 11 is a graphical visualisation of the results shown in example 10 columns A.

In this example $\lambda_{ex}=\lambda_{em}$ and the data are visually shown on FIG. 20, wherein the abscissa shows a "True size" $S_t(nm)=FWHM_{True}$ and the ordinate the detected size S(nm).

The objects diameter size values S are evaluated using the graphical Virtual Microscopy calibration representation of the modulation contrast R shown in Examples 3, 4. The continuous lines show the "True size" $S_t(nm)=FWHM_{True}$, dotted lines and bars show detected sizes and their standard deviations respectively.

Example 12 is a graphical visualisation of the results shown in example 10 columns B.

In this example $\lambda_{ex}=\lambda_{em}$ and the data are visually shown on FIG. 21, wherein the abscissa shows "True size" $S_t(nm) = FWHM_{True}$ and the ordinate shows Detected size $S(nm)$. The objects diameter size values are evaluated using the analytical adaptation function the modulation contrast R; for more details see Examples 6, 7. The continues lines show the "True size" $S_t(nm)=FWHM_{True}$, dotted lines and bars detected sizes and their standard deviations respectively.

Example 13, respectively FIG. 22 is a graphical visualisation of the results shown in example 10 columns C.

In this example $\lambda_{ex}=\lambda_{em}$ and the data are visually shown on FIG. 22, wherein the abscissa shows the "True size" $S_t(nm)=FWHM_{True}$ and the ordinate the detected size $S(nm)$. The objects diameter size values are evaluated using the linear expression of the modulation contrast R for more details see Examples 5. The continuous lines show the "True size" $S_t(nm)=FWHM_{True}$, the dotted lines and bars detected sizes and their standard deviations respectively.

Example 14 illustrates the virtual determination of object sizes using different VIM approaches.

In this example $\lambda_{em}=\lambda_{ex}+100$ nm and the data are shown on Table 2. Three different Virtual Microscopy approaches in order to determine the object size starting from the evaluation of the modulation contrast R are used. The evaluations are performed for the effective excitation wavelengths, indicated in the head row of the Table 2. Column T of Table 2 shows the "True size" values; i.e. the $FWHM_{True}$ of the objects fixed at the start of the Virtual Microscopy simulation process (see Example 2). Columns A of table 2 show determination of the object sizes using the graphical visualisation of the modulation contrast R; for more details see Examples 3, 4 and the main text. Columns B of Table 2 show determination of the object size after inversion of the analytical expression of the case % $\lambda_{em}=\lambda^*_{ex}+100$ nm. Three different Virtual Microscopy approaches in order to determine the object size starting from calibration function $R=R(S, \lambda_{ex}^*)$ are used (for more details see Examples 6, 7 and the main text). Columns C of Table 2 show determination of the object size after inversion of the linear approximation of the calibration function $R_L=R_L(S, \lambda_{ex}^*)$, (for more details see Examples 5).

Example 15 shows a modulation contrast R and size S evaluation accuracy as function of the total number of detected photons.

In this Example: $\lambda_{ex}=\lambda_{em}$. FIG. 23 is a graphical representation of the results. The abscissa of FIG. 23 is the total number of detected photons $N_{tot}$ the Ordinate is Modulation contrast R. The continuous lines (1), (2), (3), (4) are the "ideal" noiseless evaluations of the modulation contrast R corresponding to the sizes S=40 nm, S=80 nm, S=100 nm and S=140 nm respectively. The bars represent the standard deviations of the mean of the modulation contrast R evaluated in different photon count conditions. The total number of detected photons ($N_{tot}$) assumed varied between $N_{tot}=125$ and $N_{tot}=60000$.

Example 16 shows a modulation contrast R and size S evaluation accuracy as function of the total number of detected photons.

In this Example: $\lambda_{em}=\lambda_{ex}+100$ nm. FIG. 24 is a graphical representation of the results. On FIG. 24, the abscissa is the total number of detected photons $N_{tot}$ and the ordinate the Modulation contrast R. The continuous lines (1), (2), (3), (4) are the "ideal" noiseless evaluations of the modulation contrast R corresponding to the sizes S=40 nm, S=80 nm, S=100 nm and S=140 nm respectively. The bars represent the standard deviations of the mean of the modulation contrast R evaluated in different photon count conditions. The total number of detected photons ($N_{tot}$) assumed varied between $N_{tot}=125$ and $N_{tot}=60000$.

Example 17 illustrates a virtual Microscopy (VIM) computation of the modulation contrast.

Figure 25:
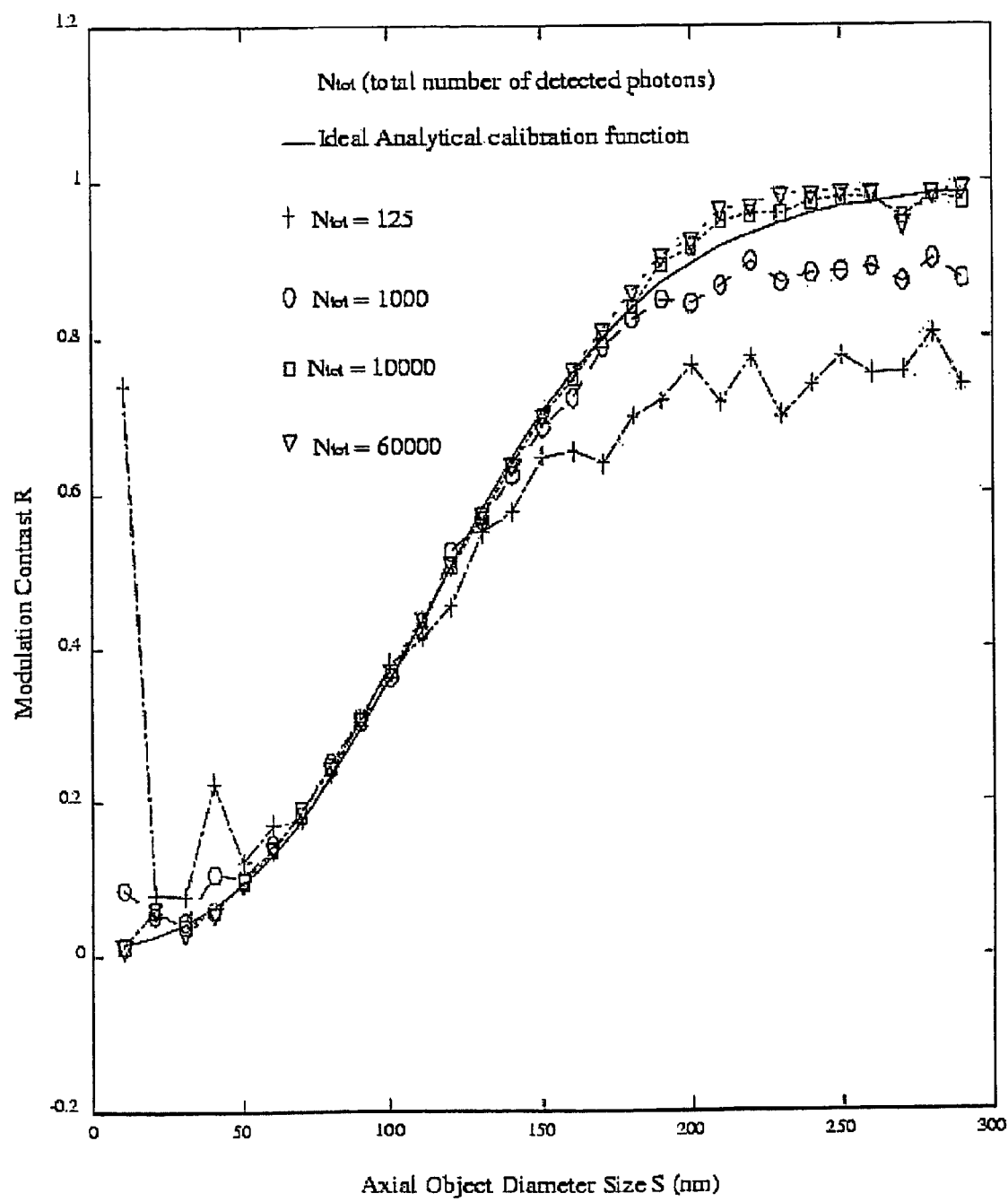
FIG. 25 shows a graph representing a virtual microscopy computation of the modulation contrast as function of different photon count conditions of Example 17.

In this Example: $\lambda_{ex}=\lambda_{em}$. FIG. 25 is a graphical representation of the results, wherein the abscissa is the Axial Object diameter size S (nm) and the ordinate the modulation contrast R. In the FIG. 25, the continuous line is refers to the case of noise less "ideal" computation of the analytical calibration function performed by Virtual Microscopy; the dotted lines represent the cases of different photon counts condition in which Poisson noise was added before starting the evaluations.

Figure 26:
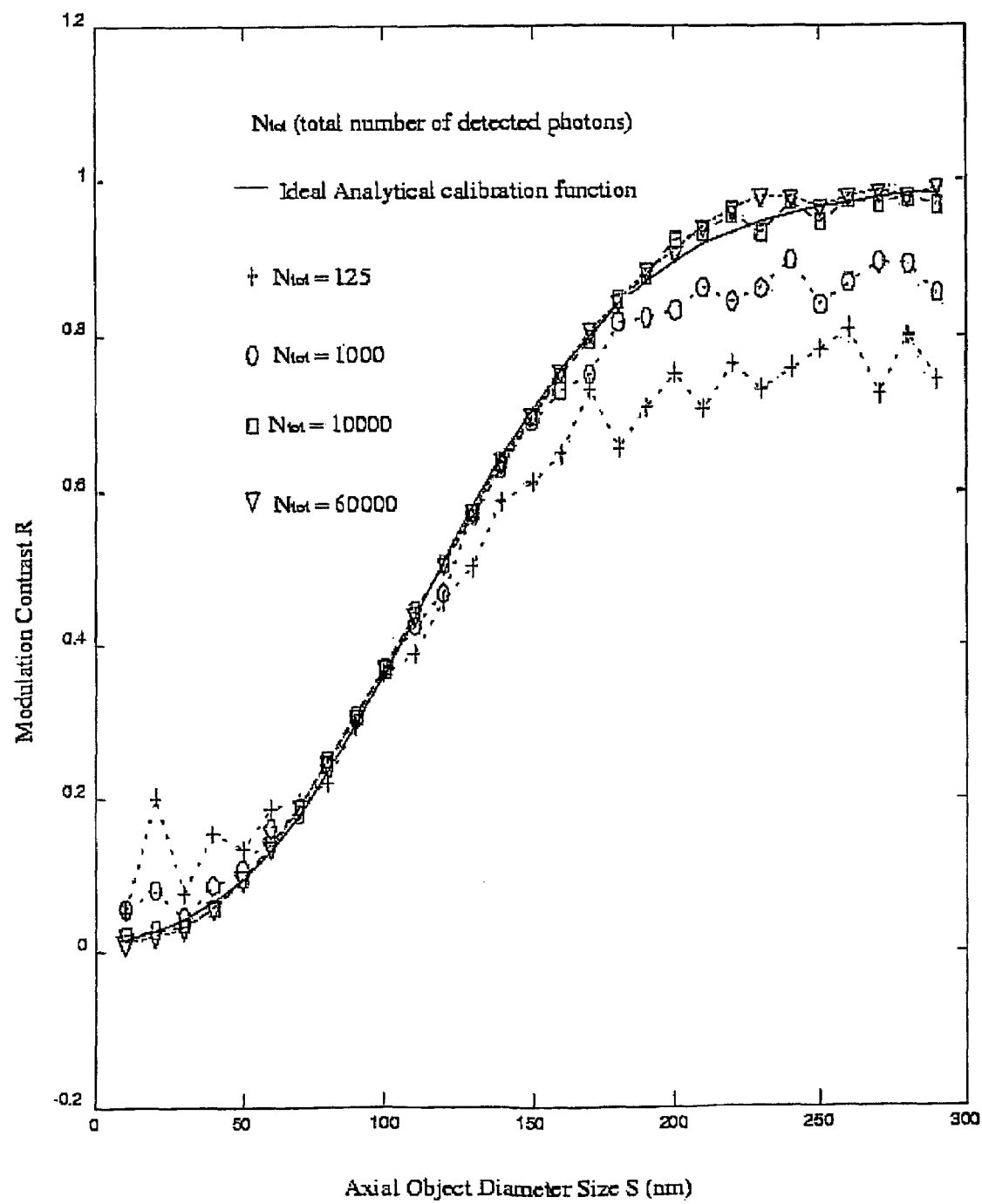
FIG. 26 shows a graph representing a virtual microscopy computation of the modulation contrast as function of different photon count conditions of Example 18.

Example 18 illustrates a virtual Microscopy (VIM) computation of the modulation contrast as function of different photon count conditions (see FIG. 26).

The data a graphically shown on FIG. 26, wherein the abscissa is Axial Object diameter size S (nm) and the ordinate: modulation contrast R. In the FIG. 26, the continuous line refers to the case of noiseless "ideal" computation of the analytical calibration function performed by Virtual Microscopy; the dotted lines represent the cases of different photon counts condition in which Poisson noise was added before starting the evaluations. Note that the differences to the conditions in Example 17 ($\lambda_{ex}=\lambda_{em}$) are very small.

Figure 27:
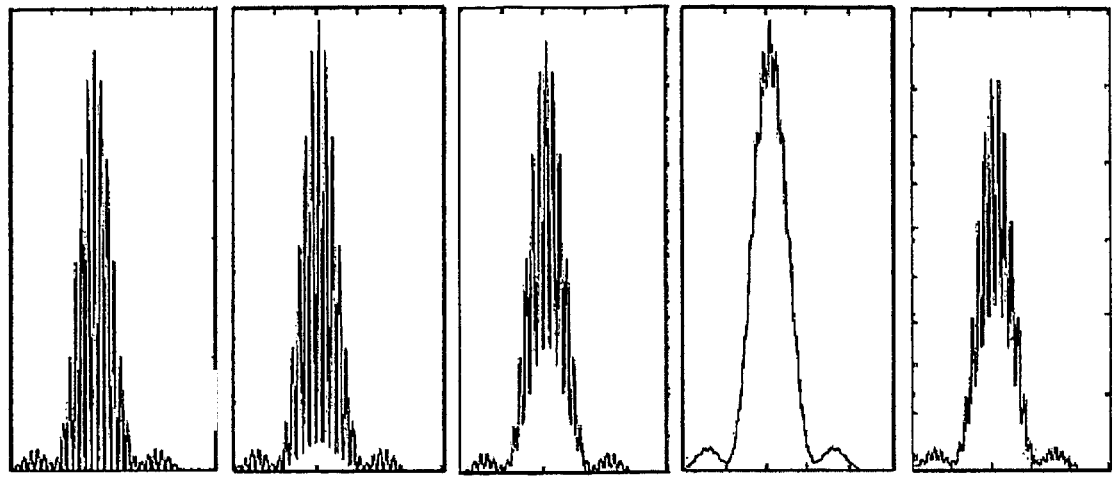
FIG. 27 shows a schematic example of the virtual microscopy evaluation of two point like axial intensity distributions of Example 19.
Figure 27:
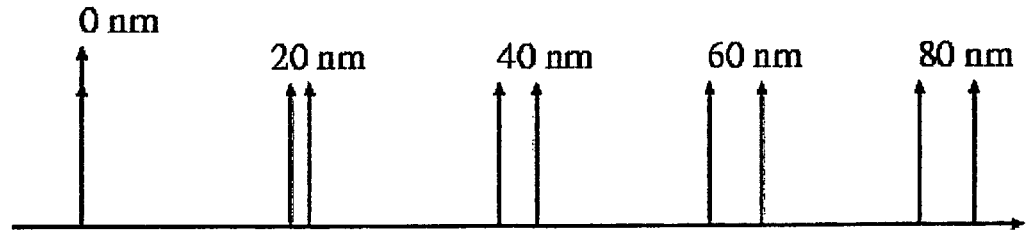
Figure 27:
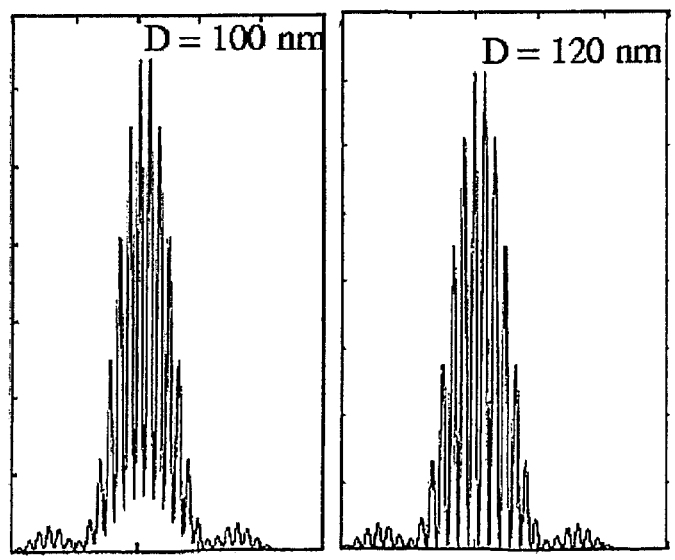

Example 19, illustrates a virtual microscopy (VIM) evaluation of "two-point-like" axial intensity distribution (see FIG. 27).

In the Example are represented the axial intensity distributions (AIDs) of two point like objects (with a diameter S=10 nm). The excitation wavelength was fixed to be $\lambda_{ex}=488$ nm. The computations were performed in "ideal" noiseless conditions using ensembles of "point like" objects (see Examples 1, 2). FIG. 27 shows that, it is possible realise calibrations functions in order to determine the relative distance of the two points using a minimum of one spectral signature. The intensity profiles are changing with the distance between the two "point-like" objects, as shown in the upper part of FIG. 27, wherein the first profile from left to right corresponds to distance D=0 nm, the second to D=20 nm, the third to D=40 nm, the fourth to D=60 nm and the fifth to D=80 nm. In the lower part of FIG. 27 are shown the intensity profiles corresponding to D=100 nm and D=120 nm respectively.

Example 20 illustrates a VIM evaluation of the object barycenter position respect to the fringes barycenter, shown graphically on FIG. 28.

In this example the wavelength of the excitation light is equal to the wavelength of the emitted light: $\lambda_{ex}=\lambda_{em}$. ($\lambda_{ex}=488$ nm). All the AIDs are produced by Virtual Microscopy in "ideal" noiseless conditions using an ensembles of 5 "point like" objects (S=50 nm) as in Examples 1,2. On FIG. 28 are shown respectively the object barycenter, the fringe barycenter position, and the SMI fringe, wherein in the right side of FIG. 28 the intensity profiles corresponding the cases: (from up to down) object barycenter coincides with fringe barycenter, respectively object barycenter on the right and on the left of the fringe barycenter, are shown in more detail.

Example 21 illustrates the results of experimental data analysis performed by the invention (see FIG. 29 and Table 3).

In the FIG. 29 are shown the results corresponding experiments performed with 100 nm (according with producer estimation) diameter spherical beads (I) emitting at $\lambda_{ex}$=647 nm and with 40 nm (according with producer estimation) beads (II) (for details of the experimental set up see for example [B. Albrecht, A. V. Failla, A. Schweitzer, C. Cremer, Spatially modulated illumination (SMI) microscopy allows axial distance resolution near the one nanometer range, Applied Optics, in press. 2001; B. Albrecht, A. V. Failla, A. Schweitzer, C. Cremer: Spatially modulated illumination microscopy: A new approach to biological nanostructure analysis, GIT-Microscopy, July 2001]). For the size determination the analytical calibration function was used (Example 6, 7).

The abscissa of FIG. 29 shows the number N of independent measurements repeated for each kind of beads and the Ordinate the object diameter size S (nm). The two independent experiments consist each of ten independent measurements of an ensemble of beads ($N_{bead}$=13). For each measurement the evaluated size ("o" for 40 nm beads, "+" for 100 nm beads) is the mean value computed from the beads ensemble; the estimated error, bars, is the standard deviation of the mean. Horizontal lines: The continuous (-) lines are the mean values of the size of the beads in the two experiments; the dashed ( - - - ) lines are the mean values of the sizes of the beads plus and minus the standard deviation respectively. To calculate the standard deviation (SD) all the 130 size measurements for each experiment were used.

In the Table 3 are shown the results of experimental objects sizes measurements. All the experiments, the results of which are shown in the Table 3, were performed in the way described above. For quite all the experiments, each one corresponding to a row of the table, four different evaluation modes of the size were computed. The first two of these evaluations were performed subtracting background from the raw data; the other two were performed without subtracting the background. Two different computations were performed, one inverting the linear relation between the modulation contrast and the object size (see text and Example 5); the other one inverting the analytical expression of the modulation contrast R as a function of the size S and the effective excitation wavelength $\lambda_{ex}^*$. In all the four cases the measured values of the size of the beads are the mean on all the beads of a given size in 10 different measurements; the evaluated errors are the standard deviations of the means.

TABLE 1

| True size (nm) | S (nm) $\lambda^*_{ex}$ = 360 nm | | | S (nm) $\lambda^*_{ex}$ = 488 nm | | |
|---|---|---|---|---|---|---|
| 10 | 9.8 ± 6.0 | 11.2 ± 5.3 | 24.0 ± 1 | 21 ± 11 | 20 ± 11 | 36 ± 8 |
| 20 | 19.2 ± 3.8 | 17.6 ± 4.9 | 26.1 ± 0.5 | 21.0 ± 8.7 | 18 ± 15 | 35 ± 3 |
| 30 | 28.8 ± 1.3 | 30.5 ± 1.5 | 31.1 ± 0.5 | 28.8 ± 1.9 | 27.6 ± 3.0 | 38 ± 1 |
| 40 | 40.3 ± 1.3 | 41.5 ± 1.3 | 38.2 ± 0.2 | 41.3 ± 1.5 | 40.8 ± 3.0 | 44 ± 1 |
| 50 | 50.0 ± 1.3 | 51.6 ± 1.6 | 47.4 ± 0.4 | 50.0 ± 1.4 | 52.2 ± 3.0 | 51 ± 1 |
| 60 | 59.8 ± 1.3 | 61.1 ± 1.3 | 57.4 ± 0.5 | 57.7 ± 2.8 | 62.1 ± 3.0 | 59 ± 2 |
| 70 | 71.1 ± 1.3 | 70.9 ± 1.3 | 68.0 ± 0.6 | 65.4 ± 4.6 | 71.9 ± 4.4 | 68 ± 2 |
| 80 | 78.8 ± 1.3 | 80.8 ± 5.1 | 77.8 ± 0.7 | 80.8 ± 2.0 | 82.4 ± 3.8 | 79 ± 2 |
| 90 | 90.3 ± 1.5 | 91.9 ± 7.7 | 87.0 ± 0.7 | 92.3 ± 2.0 | 92.4 ± 4.7 | 90 ± 2 |
| 100 | 100.0 ± 1.9 | 103.0 ± 8.6 | 95.4 ± 0.8 | 100.0 ± 2.4 | 102.1 ± 4.7 | 100 ± 2 |
| 110 | 111.5 ± 2.3 | 115.8 ± 8.1 | 99.3 ± 0.9 | 109.6 ± 2.4 | 113.9 ± 6.0 | 110 ± 3 |
| 120 | 121.0 ± 3.0 | 123.7 ± 8.1 | 102 ± 1 | 123.1 ± 3.8 | 123.9 ± 6.5 | 118 ± 3 |
| 130 | 128.8 ± 10 | 127.7 ± 9.7 | 106 ± 4 | 130.8 ± 3.8 | 134.9 ± 6.5 | 125 ± 3 |
| 140 | 140 ± 50 | 136 ± 22 | 104 ± 3 | 138.4 ± 6.7 | 140 ± 10 | 133 ± 3 |
| 150 | 140 ± 50 | 156 ± 39 | 107 ± 3 | 151.9 ± 9.6 | 151.9 ± 9.0 | 137 ± 5 |
| 160 | 179 ± 50 | 161 ± 10 | 107 ± 3 | 161.5 ± 9.6 | 163.3 ± 8.0 | 140 ± 5 |
| 170 | 179 ± 50 | 157 ± 10 | 107 ± 3 | 167 ± 13 | 175 ± 13 | 142 ± 5 |
| 180 | 179 ± 50 | 157 ± 30 | 106 ± 3 | 175.0 ± 9.6 | 185 ± 19 | 144 ± 5 |
| 190 | 179 ± 50 | 147 ± 30 | 106 ± 3 | 183 ± 35 | 191 ± 18 | 143 ± 5 |
| 200 | 140 ± 50 | 157 ± 30 | 107 ± 3 | 190 ± 45 | 193 ± 16 | 145 ± 5 |
| 210 | 179 ± 50 | 149 ± 30 | 106 ± 3 | 190 ± 45 | 198 ± 16 | 145 ± 5 |
| 220 | 179 ± 50 | 159 ± 30 | 107 ± 3 | 190 ± 45 | 201 ± 13 | 145 ± 5 |
| 230 | 179 ± 50 | 154 ± 30 | 107 ± 3 | 190 ± 45 | 173 ± 14 | 143 ± 5 |
| 240 | 179 ± 50 | 157 ± 30 | 107 ± 3 | 160 ± 45 | 203 ± 14 | 145 ± 5 |
| 250 | 179 ± 50 | 151 ± 30 | 106 ± 3 | 190 ± 45 | 192 ± 13 | 145 ± 5 |
| 260 | 179 ± 50 | 155 ± 30 | 107 ± 3 | 190 ± 45 | 210 ± 53 | 144 ± 5 |
| 270 | 179 ± 50 | 129 ± 30 | 103 ± 3 | 190 ± 45 | 201 ± 15 | 145 ± 5 |
| 280 | 179 ± 50 | 155 ± 30 | 107 ± 3 | 190 ± 45 | 205 ± 14 | 143 ± 5 |
| 290 | 179 ± 50 | 151 ± 30 | 106 ± 3 | 190 ± 45 | 191 ± 16 | 146 ± 5 |
| T | A | B | C | A | B | C |

| True size (nm) | S (nm) $\lambda^*_{ex}$ = 568 nm | | | S (nm) $\lambda^*_{ex}$ = 647 nm | | |
|---|---|---|---|---|---|---|
| 10 | 17 ± 10 | 18 ± 10 | 38 ± 9 | 25 ± 15 | 10 ± 15 | 45 ± 6 |
| 20 | 19.2 ± 6.7 | 21 ± 5.0 | 38 ± 1 | 32 ± 15 | 38.4 ± 14 | 52 ± 6 |
| 30 | 26.8 ± 4.6 | 29.0 ± 1.6 | 41 ± 1 | 30.7 ± 3.8 | 27.2 ± 4.4 | 48 ± 2 |
| 40 | 36.5 ± 3.8 | 36.8 ± 3.4 | 47 ± 1 | 36.5 ± 2.8 | 38.1 ± 2.7 | 52 ± 2 |
| 50 | 46.1 ± 3.8 | 50.0 ± 4.0 | 53 ± 1 | 50.0 ± 1.9 | 51.0 ± 3.1 | 57 ± 2 |
| 60 | 63.4 ± 1.9 | 61.2 ± 3.6 | 61 ± 1 | 57.7 ± 1.9 | 61.9 ± 2.0 | 64 ± 2 |

TABLE 1-continued

| T | A | B | C | A | B | C |
|---|---|---|---|---|---|---|
| 70 | 71.1 ± 1.9 | 70.9 ± 3.7 | 69 ± 2 | 69.2 ± 1.9 | 72.4 ± 3.3 | 72 ± 2 |
| 80 | 81.3 ± 1.9 | 80.4 ± 3.7 | 78 ± 2 | 80.8 ± 1.9 | 82.7 ± 2.0 | 81 ± 3 |
| 90 | 91.2 ± 1.9 | 90.0 ± 3.7 | 89 ± 2 | 90.3 ± 1.9 | 92.3 ± 3.5 | 90 ± 3 |
| 100 | 98.1 ± 3.0 | 99.5 ± 5.2 | 99 ± 2 | 100.0 ± 1.9 | 101.1 ± 4.1 | 100 ± 3 |
| 110 | 107.7 ± 3.0 | 108.9 ± 5.1 | 110 ± 2 | 109.6 ± 1.9 | 110.1 ± 4.1 | 110 ± 3 |
| 120 | 119.2 ± 3.0 | 118.4 ± 4.6 | 120 ± 2 | 121.1 ± 1.9 | 119.7 ± 4.3 | 121 ± 4 |
| 130 | 130.7 ± 3.0 | 128.4 ± 5.3 | 13β ± 3 | 128.8 ± 1.9 | 128.7 ± 4.7 | 130 ± 4 |
| 140 | 142.2 ± 3.0 | 140.3 ± 5.3 | 140 ± 3 | 140.3 ± 2.8 | 138.5 ± 5.6 | 141 ± 4 |
| 150 | 150.0 ± 3.0 | 151.5 ± 4.4 | 147 ± 3 | 150.3 ± 3.8 | 148.7 ± 6.2 | 151 ± 4 |
| 160 | 165.3 ± 8.6 | 166 ± 10 | 154 ± 4 | 161.5 ± 3.8 | 158.0 ± 6.8 | 158 ± 4 |
| 170 | 170 ± 12 | 175 ± 13 | 161 ± 6 | 171.7 ± 5.1 | 169.0 ± 7.4 | 166 ± 4 |
| 180 | 180.6 ± 7.7 | 181 ± 13 | 165 ± 6 | 180.8 ± 6.7 | 179.9 ± 8.2 | 172 ± 6 |
| 190 | 190.7 ± 7.7 | 193 ± 8.0 | 166 ± 6 | 196 ± 11 | 198.7 ± 9.9 | 180 ± 6 |
| 200 | 194.2 ± 5.7 | 203.0 ± 7.3 | 167 ± 6 | 207 ± 11 | 210 ± 14 | 184 ± 7 |
| 210 | 202.8 ± 8.3 | 208.2 ± 8.1 | 166 ± 6 | 215 ± 19 | 233 ± 21 | 190 ± 7 |
| 220 | 203 ± 19 | 213 ± 10 | 167 ± 6 | 225 ± 13 | 240 ± 21 | 190 ± 7 |
| 230 | 203 ± 38 | 216 ± 13 | 166 ± 6 | 225 ± 30 | 240 ± 21 | 193 ± 7 |
| 240 | 203 ± 38 | 191 ± 25 | 163 ± 6 | 261 ± 30 | 250 ± 21 | 189 ± 7 |
| 250 | 203 ± 38 | 214 ± 24 | 167 ± 6 | 261 ± 30 | 250 ± 24 | 193 ± 7 |
| 260 | 203 ± 38 | 213 ± 25 | 167 ± 6 | 261 ± 30 | 250 ± 21 | 193 ± 7 |
| 270 | 203 ± 38 | 217 ± 23 | 167 ± 6 | 261 ± 30 | 237 ± 25 | 185 ± 7 |
| 280 | 203 ± 38 | 215 ± 26 | 167 ± 6 | 261 ± 30 | 250 ± 23 | 193 ± 7 |
| 290 | 203 ± 38 | 186 ± 30 | 161 ± 6 | 261 ± 30 | 250 ± 30 | 193 ± 7 |
| T | A | B | C | A | B | C |

TABLE 2

| True size (nm) | S(nm) $\lambda^*_{ex} = 360$ nm | | | S(nm) $\lambda^*_{ex} = 488$ nm | | |
|---|---|---|---|---|---|---|
| 10 | 9.6 ± 6.0 | 9.8 ± 5.3 | 20 ± 1 | 19 ± 10 | 6.9 ± 8.8 | 13 ± 8 |
| 20 | 12.3 ± 3.8 | 14.7 ± 4.9 | 19.4 ± 0.3 | 19.2 ± 3.7 | 11 ± 10 | 25 ± 3 |
| 30 | 30.7 ± 1.9 | 31.9 ± 2.5 | 34.1 ± 0.3 | 28.8 ± 1.9 | 28.5 ± 3.5 | 40 ± 1 |
| 40 | 44.2 ± 1.3 | 44.5 ± 2.6 | 49.4 ± 0.3 | 41.3 ± 1.5 | 41.2 ± 3.6 | 45 ± 1 |
| 50 | 51.9 ± 1.3 | 52.7 ± 1.9 | 49.6 ± 0.4 | 50.0 ± 1.4 | 52.4 ± 2.8 | 52 ± 1 |
| 60 | 61.5 ± 1.3 | 62.1 ± 2.0 | 59.3 ± 0.5 | 57.7 ± 2.8 | 62.4 ± 3.0 | 60 ± 2 |
| 70 | 69.2 ± 1.3 | 71.7 ± 2.1 | 69.3 ± 0.6 | 67.4 ± 4.6 | 72.8 ± 5.2 | 70 ± 2 |
| 80 | 80.7 ± 1.3 | 81.8 ± 2.3 | 79.3 ± 0.6 | 80.7 ± 2.0 | 82.6 ± 3.0 | 80 ± 2 |
| 90 | 90.3 ± 1.3 | 92.5 ± 1.8 | 87.6 ± 0.9 | 92.3 ± 2.0 | 93.2 ± 3.4 | 90 ± 2 |
| 100 | 100.0 ± 1.5 | 99.5 ± 2.8 | 94.9 ± 0.7 | 100.0 ± 2.4 | 102.9 ± 3.4 | 100 ± 2 |
| 110 | 113.5 ± 1.9 | 113.6 ± 2.9 | 104.4 ± 0.9 | 109.6 ± 2.4 | 112.8 ± 3.6 | 110 ± 2 |
| 120 | 121.0 ± 2.3 | 124.4 ± 3.5 | 104 ± 1 | 121.1 ± 3.8 | 122.9 ± 4.5 | 119 ± 3 |
| 130 | 128.8 ± 3.0 | 134.9 ± 4.2 | 107 ± 4 | 130.8 ± 3.8 | 131.3 ± 5.5 | 126 ± 3 |
| 140 | 140 ± 10 | 160.5 ± 7.6 | 107 ± 3 | 138.4 ± 6.7 | 139.9 ± 8.5 | 132 ± 3 |
| 150 | 140 ± 50 | 156 ± 23 | 107 ± 3 | 150.0 ± 9.6 | 148.4 ± 8.8 | 135 ± 3 |
| 160 | 179 ± 50 | 148 ± 18 | 106 ± 3 | 154.4 ± 9.6 | 171 ± 12 | 139 ± 5 |
| 170 | 179 ± 50 | 142 ± 24 | 105 ± 3 | 167 ± 13 | 181 ± 15 | 141 ± 5 |
| 180 | 179 ± 50 | 143 ± 34 | 105 ± 3 | 171 ± 10 | 189 ± 18 | 142 ± 5 |
| 190 | 179 ± 50 | 143 ± 25 | 108 ± 3 | 183 ± 35 | 193 ± 18 | 143 ± 5 |
| 200 | 140 ± 50 | 168 ± 32 | 107 ± 3 | 190 ± 45 | 208 ± 26 | 145 ± 5 |
| 210 | 179 ± 50 | 160 ± 33 | 107 ± 3 | 190 ± 45 | 204 ± 23 | 145 ± 5 |
| 220 | 179 ± 50 | 161 ± 26 | 107 ± 3 | 190 ± 45 | 208 ± 23 | 145 ± 5 |
| 230 | 179 ± 50 | 161 ± 33 | 107 ± 3 | 190 ± 45 | 209 ± 26 | 143 ± 5 |
| 240 | 179 ± 50 | 163 ± 28 | 107 ± 3 | 160 ± 45 | 207 ± 22 | 145 ± 5 |
| 250 | 179 ± 50 | 161 ± 24 | 107 ± 3 | 190 ± 45 | 212 ± 21 | 145 ± 5 |
| 260 | 179 ± 50 | 161 ± 36 | 107 ± 3 | 190 ± 45 | 206 ± 25 | 144 ± 5 |
| 270 | 179 ± 50 | 162 ± 33 | 109 ± 3 | 190 ± 45 | 199 ± 24 | 147 ± 5 |
| 280 | 179 ± 50 | 160 ± 32 | 108 ± 3 | 190 ± 45 | 198 ± 26 | 143 ± 5 |
| 290 | 179 ± 50 | 165 ± 29 | 107 ± 3 | 190 ± 45 | 201 ± 30 | 146 ± 5 |
| T | A | B | C | A | B | C |

| True size (nm) | S(nm) $\lambda^*_{ex} = 568$ nm | | | S(nm) $\lambda^*_{ex} = 647$ nm | | |
|---|---|---|---|---|---|---|
| 10 | 17 ± 10 | 8.0 ± 4.0 | 31 ± 9 | 25 ± 15 | 17 ± 10 | 39 ± 6 |
| 20 | 17.3 ± 8.1 | 16.4 ± 6.4 | 29 ± 1 | 32 ± 15 | 21 ± 12 | 36 ± 6 |
| 30 | 30.8 ± 5.4 | 24.2 ± 5.2 | 46 ± 1 | 28.8 ± 5.8 | 25.0 ± 6.7 | 52 ± 2 |
| 40 | 38.5 ± 3.8 | 38.8 ± 5.5 | 54 ± 1 | 36.5 ± 5.8 | 36.5 ± 6.9 | 63 ± 2 |
| 50 | 48.5 ± 3.8 | 50.3 ± 4.7 | 55 ± 1 | 48.5 ± 1.9 | 50.3 ± 3.4 | 59 ± 2 |
| 60 | 63.4 ± 1.9 | 61.1 ± 3.4 | 62 ± 1 | 57.7 ± 1.9 | 62.4 ± 3.0 | 61 ± 2 |
| 70 | 71.1 ± 1.9 | 71.2 ± 3.6 | 70 ± 2 | 69.2 ± 1.9 | 72.3 ± 3.1 | 72 ± 2 |
| 80 | 81.3 ± 1.9 | 80.5 ± 3.3 | 79 ± 2 | 80.8 ± 1.9 | 82.9 ± 2.8 | 82 ± 3 |
| 90 | 91.2 ± 1.9 | 90.4 ± 3.6 | 89 ± 2 | 90.3 ± 1.9 | 92.2 ± 3.1 | 90 ± 3 |
| 100 | 98.1 ± 3.0 | 99.3 ± 5.0 | 99 ± 2 | 100.0 ± 1.9 | 100.7 ± 3.3 | 100 ± 3 |

TABLE 2-continued

| T | A | B | C | A | B | C |
|---|---|---|---|---|---|---|
| 110 | 107.7 ± 3.0 | 108.6 ± 4.4 | 110 ± 2 | 111.5 ± 1.9 | 111.2 ± 3.1 | 111 ± 3 |
| 120 | 117.3 ± 3.0 | 119.4 ± 4.6 | 121 ± 2 | 119.2 ± 1.9 | 119.4 ± 3.4 | 121 ± 4 |
| 130 | 128.8 ± 3.0 | 128.9 ± 4.6 | 130 ± 3 | 128.8 ± 1.9 | 128.2 ± 3.4 | 130 ± 4 |
| 140 | 140.3 ± 3.0 | 138.9 ± 3.8 | 139 ± 3 | 138.5 ± 2.8 | 137.4 ± 4.9 | 141 ± 4 |
| 150 | 151.9 ± 3.0 | 150.9 ± 4.3 | 146 ± 3 | 148.1 ± 3.8 | 148.2 ± 5.5 | 150 ± 4 |
| 160 | 165.3 ± 8.6 | 166.8 ± 8.5 | 154 ± 4 | 161.5 ± 3.8 | 158.1 ± 6.2 | 157 ± 4 |
| 170 | 170 ± 12 | 172.7 ± 8.6 | 161 ± 6 | 171.7 ± 5.1 | 168.0 ± 8.4 | 164 ± 4 |
| 180 | 180.6 ± 7.7 | 180.1 ± 9.6 | 165 ± 6 | 180.8 ± 6.7 | 182.1 ± 9.8 | 172 ± 6 |
| 190 | 190.7 ± 7.7 | 191.3 ± 9.9 | 167 ± 6 | 194 ± 11 | 193 ± 12 | 178 ± 6 |
| 200 | 194.2 ± 5.7 | 208.5 ± 9.6 | 168 ± 6 | 211 ± 11 | 213 ± 14 | 185 ± 7 |
| 210 | 202.8 ± 8.3 | 222.9 ± 9.1 | 169 ± 6 | 215 ± 19 | 221 ± 12 | 190 ± 7 |
| 220 | 203 ± 19 | 223 ± 14 | 169 ± 6 | 225 ± 13 | 238 ± 11 | 187 ± 7 |
| 230 | 203 ± 38 | 225 ± 16 | 169 ± 6 | 225 ± 30 | 220 ± 10 | 189 ± 7 |
| 240 | 203 ± 38 | 225 ± 18 | 170 ± 6 | 261 ± 30 | 250 ± 14 | 189 ± 7 |
| 250 | 203 ± 38 | 227 ± 16 | 169 ± 6 | 261 ± 30 | 231 ± 15 | 192 ± 7 |
| 260 | 203 ± 38 | 227 ± 16 | 167 ± 6 | 261 ± 30 | 250 ± 11 | 193 ± 7 |
| 270 | 203 ± 38 | 225 ± 15 | 170 ± 6 | 261 ± 30 | 250 ± 12 | 195 ± 7 |
| 280 | 203 ± 38 | 229 ± 17 | 169 ± 6 | 261 ± 30 | 250 ± 16 | 193 ± 7 |
| 290 | 203 ± 38 | 229 ± 22 | 169 ± 6 | 261 ± 30 | 250 ± 20 | 193 ± 7 |

TABLE 3

| | Computation without background | | Computation with background | |
|---|---|---|---|---|
| | Analytical function | Linear function | Analytical function | Linear function |
| 40 nm beads $\lambda_{ex}^*$ = 647 nm | (35.7 ± 3.6) nm | (51.9 ± 1.7) nm | (30.4 ± 5.0) nm | (50.2 ± 1.6) nm |
| 100 nm beads $\lambda_{ex}^*$ = 647 nm | (85.5 ± 8.3) nm | (83.2 ± 4.1) nm | (83.9 ± 6.2) nm | (82.1 ± 5.4) nm |
| 175 nm beads $\lambda_{ex}^*$ = 647 nm | (106.2 ± 1.7) nm | (104.2 ± 1.9) nm | (111.0 ± 2.9) nm | (109.1 ± 3.2) nm |
| 100 nm beads $\lambda_{ex}^*$ = 488 nm | (97.8 ± 4.6) nm | (95.6 ± 4.6) nm | (95.7 ± 4.1) nm | (93.4 ± 4.3) nm |
| 175 nm beads $\lambda_{ex}^*$ = 488 nm | (137.1 ± 2.7) nm | (126.9 ± 1.6) nm | | |
| 175 nm beads $\lambda_{ex}^*$ = 488 nm | (132.5 ± 8.2) nm | (124.1 ± 6.0) nm | | |

The invention claimed is:

1. Far field light microscopical method for analysing at least one object having a subwavelength size in at least one spatial direction to obtain spatial information of the object, in particular size and topology thereof, comprising the steps of:
    labelling the at least one object with one or more suitable optical markers;
    providing suitably structured illumination light to at least partially illuminate the at least one object;
    subjecting the at least one object to the structured illumination light;
    detecting an optical response of the at least one object;
    obtaining the spatial information of the at least one object by comparing the obtained response with simulation data of an optical response of at least one object having known spatial information, wherein the spatial information comprises at least one of the following information:
    size of the object in at least one spatial direction;
    topology of the object in at least one spatial direction;
    at least one distance between at least two obiects in at least one spatial direction.

2. Far field light microscopical method according to claim 1, wherein in the step of labelling the object with a plurality of markers the optical markers are all the same;
at least two of the optical markers are different;
pairs of different optical markers are used;
all of elements of the object are labelled with a first optical marker, and the elements within are labelled with at least one second optical marker, different from the first optical marker; and/or
the object is labelled with a linear sequence of optical markers.

3. Far field light microscopical method for analysing at least one object having a subwavelength size in at least one spatial direction to obtain spatial information of the object, in particular size and topology thereof, comprising the steps of:
    labelling the at least one object with one or more suitable optical markers:
    providing suitably structured illumination light to at least partially illuminate the at least one object;
    subjecting the at least one object to the structured illumination light;
    detecting an optical response of the at least one object;
    obtaining the spatial information of the at least one object by comparing the obtained response with simulation data of an optical response of at least one object having known spatial information, wherein a modulation contrast of an intensity distribution of the light returned from the object is detected and compared with simulated data of the modulation contrast of the intensity distribution.

4. Far field light microscopical method according to claim 1, wherein the optical markers comprise fluorescent markers and the optical response of the object is an intensity distribution of the emitted light from the fluorescent markers.

5. Far field light microscopical method for analysing at least one object having a subwavelength size in at least one spatial direction to obtain spatial information of the object, in particular size and topology thereof, comprising the steps of:
    labelling the at least one object with one or more suitable optical markers;
    providing suitably structured illumination light to at least partially illuminate the at least one object;
    subjecting the at least one object to the structured illumination light;
    detecting an optical response of the at least one object;

obtaining the spatial information of the at least one object by comparing the obtained response with simulation data of an optical response of at least one object having known spatial information, wherein the optical markers comprise fluorescent markers and the optical response of the object is an intensity distribution of the emitted light from the fluorescent markers and wherein the illumination light has such a wavelength that the optical markers are excited by a one-photon process.

6. Far field light microscopical method for analysing at least one object having a subwavelength size in at least one spatial direction to obtain spatial information of the object, in particular size and topology thereof, comprising the steps of:
labelling the at least one object with one or more suitable optical markers;
providing suitably structured illumination light to at least partially illuminate the at least one obiect;
subjecting the at least one object to the structured illumination light;
detecting an optical response of the at least one object;
obtaining the spatial information of the at least one object by comparing the obtained response with simulation data of an optical response of at least one object having known spatial information, wherein the optical markers comprise fluorescent markers and the optical response of the object is an intensity distribution of the emitted light from the fluorescent markers and wherein the illumination light has such a wavelength that the optical markers are excited by a two-photon or multiphoton process and wherein the step of labelling comprises labelling the object with more than three different optical markers simultaneously.

7. Far field light microscopical method claim 1, wherein the structured illumination is a spatially modulated illumination.

8. Far field light microscopical method for analysing at least one object having a subwavelength size in at least one spatial direction to obtain spatial information of the object, in particular size and topology thereof, comprising the steps of:
labelling the at least one object with one or more suitable optical markers;
providing suitably structured illumination light to at least partially illuminate the at least one object;
subjecting the at least one object to the structured illumination light;
detecting an optical response of the at least one object;
obtaining the spatial information of the at least one object by comparing the obtained response with simulation data of an optical response of at least one object having known spatial information, wherein the structured illumination is a spatially modulated illumination and wherein the structured illumination is realised in at least:
one or more directions in a plane containing the object and/or
direction substantially perpendicular to the object.

9. Far field light microscopical method according to claim 8, comprising the step of obtaining information about the sub-wavelength distance between two adjacent layers, wherein the layers may comprise thin extended elements in a given part of the layers equal or larger than the optical resolution, and the step of illuminating, such that the structured illumination is realised in the direction substantially perpendicular to the layers in this part and wherein the step of labelling comprises at least one of:
labelling the space between the adjacent layers with a minimum of one optical marker;
labelling the layers with a first optical marker, whereas the space between is labelled with another optical marker, or not labelled at all; and/or
labelling the layers with the same optical marker as used to label the space within, or additionally with other optical markers not related to the distance measurements.

10. Far field light microscopical method for analysing at least one object having a subwavelength size in at least one spatial direction to obtain spatial information of the object, in particular size and topology thereof, comprising the steps of:
labelling the at least one object with one or more suitable optical markers;
providing suitably structured illumination light to at least partially illuminate the at least one object;
subjecting the at least one object to the structured illumination light;
detecting an optical response of the at least one object;
obtaining the spatial information of the at least one object by comparing the obtained response with simulation data of an optical response of at least one object having known spatial information, wherein the step of labelling the object comprises labelling at least one pair of point like elements of the object with the same optical markers and further comprising the step of obtaining at least
the distances between the point like elements;
the distance between elements labelled with the same spectral signature using a-priory information that there are only two such elements labelled with the same spectral signature; and/or
the topology of the point like elements, especially in combination with Spectral Position Distance Microscopy, axial tomographic tools or other methods of spatially modulated or otherwise structured illumination.

11. Far field light microscopical method according to claim 10, wherein step of labelling comprises labelling the object so that a distance(s) between optical markers are smaller than the Full-Width-at-Half-Maximum of the intensity fringes ($FWHM_f$) of the spatially modulated illumination, and further comprising the step of obtaining the distance between the elements of each pair, the position of the fluorescence intensity barycenter of each pair, and/or the relative rotation angles between vectors given by the connecting lines between the centres of the elements of each pair labelled with the same spectral signature and the step of evaluation of this information using geometrical considerations.

12. Far field light microscopical method for analysing at least one object having a subwavelength size in at least one spatial direction to obtain spatial information of the object, in particular size and topology thereof, comprising the steps of:
labelling the at least one object with one or more suitable optical markers;
providing suitably structured illumination light to at least partially illuminate the at least one object;
subjecting the at least one object to the structured illumination light;
detecting an optical response of the at least one object;
obtaining the spatial information of the at least one object by comparing the obtained response with simulation data of an optical response of at least one object having known spatial information, wherein the step of labelling the object comprises labelling a plurality of elements (E1, E2, E3 . . . $E_N$), each element with a subwavelength size, such that the entire sequence being within the limits of conventional optical resolution and each element is labelled:

with all elements of the sequence labelled with different optical markers or with at least two elements of the sequence are labelled with the same optical markers or randomly, wherein all the optical markers are different or randomly, wherein the object is labelled with pairs of different optical markers.

13. Far field light microscopical method for analysing at least one object having a subwavelenath size in at least one spatial direction to obtain spatial information of the object, in particular size and topology thereof, comprising the steps of:

labelling the at least one object with one or more suitable optical markers;

providing suitably structured illumination light to at least partially illuminate the at least one object;

subjecting the at least one object to the structured illumination light;

detecting an optical response of the at least one object;

obtaining the spatial information of the at least one object by comparing the obtained response with simulation data of an optical response of at least one object having known spatial information, wherein the step of labelling comprises labelling in the object a plurality of linear sequence arrangements of elements L1s1s2s3 . . . sn; L2s1s2s3 . . . sn; L3s1s2s3 . . . sn; LNs1s2s3 . . . sn, such that si, i =1, 2, . . . , n, is realised either by an element $S^0$ representing the binary code 0, or by an element $S^1$, representing the binary code 1 and wherein the element $S^0$ binds to a first optical marker, the element $S^1$ binds to a second optical marker and the starting element L1 binds third optical marker, the starting element L2 binds to a fourth optical marker, etc.;

the individual sequence arrangements have a mean distance from each other larger than or equal to the optical resolution of the optical system used for analysis;

the far field light microscopical method further comprising the step of determining the at least one-dimensional sequence arrangement, the size and the topography of the linear sequences.

14. Far field light microscopical method for analysing at least one object having a subwavelength size in at least one spatial direction to obtain spatial information of the object, in particular size and topology thereof, comprising the steps of:

labelling the at least one object with one or more suitable optical markers;

providing suitably structured illumination light to at least partially illuminate the at least one object;

subjecting the at least one object to the structured illumination light;

detecting an optical response of the at least one object;

obtaining the spatial information of the at least one object by comparing the obtained response with simulation data of an optical response of at least one object having known spatial information, when determining the size of a fluorochrome object and comprising at least one of the steps of:

determining the fluorochrome density of objects by comparing the determined size with a size of the object determined by other means than far field light microscopical methods and/or determining the average time in which the fluorochrome objects lose their homogeneity properties by applying several statistical measurements of the objects after different time intervals.

15. Far field light microscopical method for analysing at least one object having a subwavelength size in at least one spatial direction to obtain spatial information of the object, in particular size and topology thereof, comprising the steps of:

labelling the at least one object with one or more suitable optical markers;

providing suitably structured illumination light to at least partially illuminate the at least one object;

subjecting the at least one object to the structured illumination light;

detecting an optical response of the at least one object;

obtaining the spatial information of the at least one object by comparing the obtained response with simulation data of an optical response of at least one object having known spatial information, wherein the object is an extended object comprising a plurality of point like elements symmetrically or not symmetrically distributed within the object with respect to the fringe barycenter and comprising at least one of the steps of:

determining the position of the barycenter of a fluorescent object with respect to the barycenter of the fringe pattern;

determining how the position of the barycenter of an extended homogeneous fluorescent object with respect to the fringe pattern barycenter changes in different time acquisitions; and determining the time and space stability of the laser illumination used in the step of providing suitably structured light by measuring how the position of the barycenter of an extended homogeneous fluorescent object changes with respect to the fringe pattern barycenter in different time acquisitions and in different illumination conditions.

16. Far field light microscopical method for analysing at least one object having a subwavelength size in at least one spatial direction to obtain spatial information of the object, in particular size and topology thereof, comprising the steps of:

labelling the at least one object with one or more suitable optical markers;

providing suitably structured illumination light to at least partially illuminate the at least one object;

subjecting the at least one object to the structured illumination light;

detecting an optical response of the at least one object;

obtaining the spatial information of the at least one object by comparing the obtained response with simulation data of an optical response of at least one object having known spatial information; and visualising online on a monitor the fluorescence intensity distribution wherein any region of interest can be preferably marked interactively by a computer pointer and displaying the axial and the lateral fluorescence intensity distribution registered in this region of interest.

17. Far field light microscopical system to obtain information of the spatial structure of the objects labelled with optical markers comprising:

an illumination optical system capable of providing suitably structured illumination light to at least partially illuminate the objects;

a detection system to detect the light returned from the object;

an evaluation system to evaluate the detected data using simulated data of the optical response of the object, wherein the optical markers are fluorescence markers and wherein the illumination system is capable of providing light with a wavelength so as to excite the fluorescence markers by a one-photon process and/or multi-photon process.

18. Far field light microscopical system according to claim 17, wherein the illumination system is capable of providing a spatially modulated light.

19. Far field light microscopical system to obtain information of the spatial structure of the object s labelled with optical markers comprising:

an illumination optical system capable of providing suitably structured illumination light to at least partially illuminate the object;

a detection system to detect the light returned from the objects;

an evaluation system to evaluate the detected data using simulated data of the optical response of the object, wherein the illumination system is capable of providing a structured light modulated in one or more directions in the object plane;

a structured light simultaneously and sequentially modulated in the lateral and axial directions; and/or providing structured light modulated in a direction perpendicular to the object plane.

20. Far field light microscopical system to obtain information of the spatial structure of the objects labelled with optical markers comprising:

an illumination optical system capable of providing suitably structured illumination light to at least partially illuminate the objects;

a detection system to detect the light returned from the object;

an evaluation system to evaluate the detected data using simulated data of the optical response of the object, wherein the evaluation system is capable of evaluating:

size of the object in at least one spatial direction;

topology of the object in at least one spatial direction;

distances between at least two objects in at least one spatial direction;

size and topology of the enveloping ellipsoid and/or the topology of the elements comprising the object and producing such ellipsoid;

position of an intensity barycenter in at least one spatial direction; and/or size, topology and arrangement of the sequence of elements comprising the object in at least one spatial direction.

21. Far field light microscopical system, according to claim 17, wherein the illumination and detection system are integrated and there are provided means to separate the illumination from detected light.

* * * * *